(12) United States Patent
Miki et al.

(10) Patent No.: US 9,750,827 B2
(45) Date of Patent: Sep. 5, 2017

(54) NEAR-INFRARED DYE-CONJUGATED HYALURONIC ACID DERIVATIVE AND CONTRAST AGENT FOR OPTICAL IMAGING INCLUDING THEM

(71) Applicant: CANON KABUSHIKI KAISHA, Tokyo (JP)

(72) Inventors: Koji Miki, Kyoto (JP); Tatsuhiro Inoue, Kyoto (JP); Yasuhito Kobayashi, Kyoto (JP); Katsuya Nakano, Kyoto (JP); Kouichi Ohe, Kyoto (JP); Fumio Yamauchi, Kyoto (JP); Tetsuya Yano, Kyoto (JP); Masato Minami, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/767,362

(22) PCT Filed: Feb. 21, 2014

(86) PCT No.: PCT/JP2014/054990
§ 371 (c)(1),
(2) Date: Aug. 12, 2015

(87) PCT Pub. No.: WO2014/129674
PCT Pub. Date: Aug. 28, 2014

(65) Prior Publication Data
US 2015/0374856 A1    Dec. 31, 2015

(30) Foreign Application Priority Data
Feb. 22, 2013    (JP) .................. 2013-033633

(51) Int. Cl.
A61K 8/00      (2006.01)
A61K 49/22     (2006.01)
C08B 37/08     (2006.01)
A61K 47/48     (2006.01)

(52) U.S. Cl.
CPC ........ *A61K 49/221* (2013.01); *C08B 37/0072* (2013.01); *A61K 47/48* (2013.01); *A61K 47/481* (2013.01); *A61K 47/48007* (2013.01); *A61K 47/4823* (2013.01); *A61K 47/48169* (2013.01)

(58) Field of Classification Search
None
See application file for complete search history.

(56) References Cited

U.S. PATENT DOCUMENTS

| | | |
|---|---|---|
| 5,747,475 A | 5/1998 | Nordquist et al. |
| 6,149,671 A | 11/2000 | Nordquist et al. |
| 6,290,712 B1 | 9/2001 | Nordquist et al. |
| 6,316,007 B1 | 11/2001 | Nordquist et al. |
| 8,512,752 B2 | 8/2013 | Crescenzi et al. |
| 9,056,131 B2 | 6/2015 | Teranishi et al. |
| 9,352,053 B2 | 5/2016 | Tabata et al. |
| 2002/0136729 A1 | 9/2002 | Nordquist et al. |
| 2005/0106153 A1 | 5/2005 | Nordouist et al. |
| 2008/0056999 A1 | 3/2008 | Sharma et al. |
| 2013/0323178 A1 | 12/2013 | Yamauchi et al. |
| 2015/0152267 A1 | 6/2015 | Teranishi et al. |
| 2015/0157741 A1 | 6/2015 | Yamauchi et al. |
| 2015/0165071 A1 | 6/2015 | Takahashi et al. |
| 2015/0290345 A1 | 10/2015 | Takahashi et al. |

FOREIGN PATENT DOCUMENTS

| | | |
|---|---|---|
| CN | 1186440 A | 7/1998 |
| CN | 101528780 A | 9/2009 |
| CN | 102770460 A | 11/2012 |
| JP | 2006-25625 A | 2/2006 |
| JP | 2009-155486 A | 7/2009 |
| WO | 02/087498 A2 | 11/2002 |
| WO | 2008/025000 A2 | 2/2008 |
| WO | 2011/053803 A2 | 5/2011 |

OTHER PUBLICATIONS

Hyejung Mok et al., "Indocyanine Green Encapsulated Nanogels for Hyaluronidase Activatable and Selective Near Infrared Imaging of Tumors and Lymph Nodes," 48(69) Chem. Commun. 8628-8630 (Jun. 2012) (XP55115499).

Ki Young Choi et al., "PEGylation of Hyaluronic Acid Nanoparticles Improves Tumor Targetability in vivo," 32(7) Biomaterials 1880-1889 (Mar. 2011).

Terukage Hirata et al., "Synthesis and Reactivities of 3-Indocyanine-Green-Acyl-1,3-Thiazolidine-2-Thione (ICG-ATT) as a New Near-Infrared Fluorescent-Labeling Reagent," 6(11) Bioorg. Med. Chem. 2179-2184 (Nov. 1998).

Fabio Salvatore Palumbo et al., "New Graft Copolymers of Hyaluronic Acid and Polylactic Acid: Synthesis and Characterization," 66 Carbohydrate Polym. 379-385 (May 2006).

Marion H.M. Oudshoorn et al., "Synthesis of Methacrylated Hyaluronic Acid with Tailored Degree of Substitution," 48(7) Polymer 1915-1920 (Mar. 2007).

Bertrand Carboni et al., "Aliphatic Amino Azides as Key Building Blocks for Efficient Polyamine Syntheses," 58(14) J. Org. Chem. 3736-3741 (Jul. 1993).

Koji Miki et al., "Ring-Opening Metathesis Polymerization-Based Synthesis of Polymeric Nanoparticles for Enhanced Tumor Imaging in vivo: Synergistic Effect of Folate-Receptor Targeting and PEGylation," 31(5) Biomaterials 934-942 (Feb. 2010) (XP026790423).

Mark A. Breidenbach et al., "Targeted Metabolic Labeling of Yeast N-glycans with Unnatural Sugars," 107(9) Proc. Natl. Acad. Sci. USA 3988-3993 (Mar. 2010). Natl.

(Continued)

*Primary Examiner* — James Rogers
(74) *Attorney, Agent, or Firm* — Fitzpatrick, Cella, Harper & Scinto

(57) ABSTRACT

Provided is a compound having a high ICG content that has high accumulation property in a tumor and has a large intensity of a photoacoustic signal emitted from the tumor even when a time period elapses after administration. Specifically, provided is a hyaluronic acid derivative to which polyethylene glycol and an ICG derivative are conjugated.

9 Claims, 24 Drawing Sheets

(56) References Cited

OTHER PUBLICATIONS

Gloria Huerta-Angeles et al., "Synthesis of Highly Substituted Amide Hyaluronan Derivatives with Tailored Degree of Substitution and Their Crosslinking via Click Chemistry," 84(4) Carbohydrate Polym. 1293-1300 (Apr. 2011).

Cabriella Testa et al., "Influence of Dialkyne Structure on the Properties of New Click-Gels Based on Hyaluronic Acid," 378(1-2) Int. J. Pharm. 86-92 (Aug. 2009).

First Office Action in Chinese Application No. 201480009911.9 (Jun. 28, 2016).

Koji Miki et al., "Ring-Opening Metathesis Polymerization-Based Synthesis of ICG-Containing Amphiphilic Triblock Copolymers for in Vivo Tumor Imaging," 20 (3) Bioconjugate Chem. 511-517 (Feb. 2009).

Second Office Action in Chinese Application No. 201480009911.9 (Mar. 2, 2017).

FIG. 2
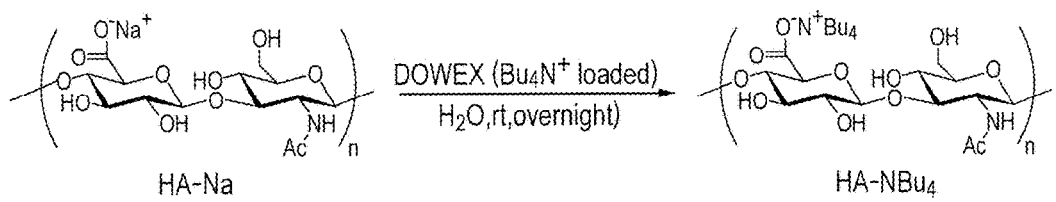
FIG. 3A
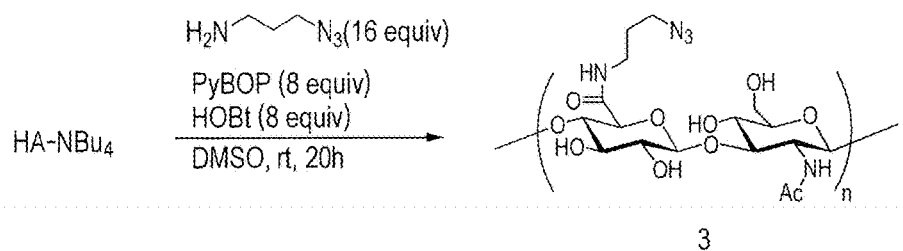
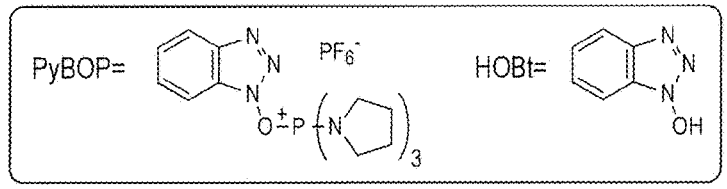
FIG. 3B
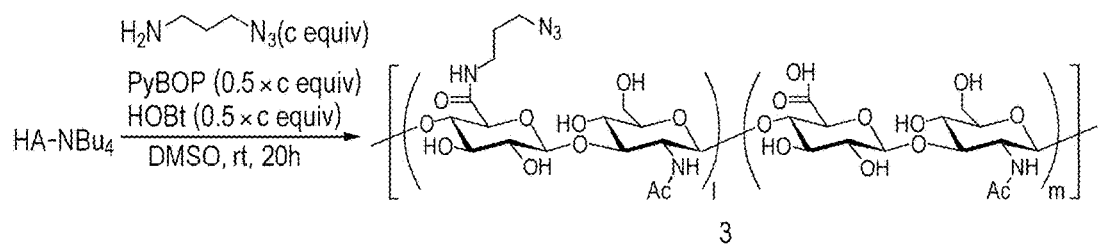

FIG. 18

| | APPARENT MOLECULAR WEIGHT OF HYALURONIC ACID UNIT | NUMBER OF ICG'S BOUND TO HYALURONIC ACID | MOLECULAR WEIGHT OF ENTIRE POLYMER | ABSORPTION COEFFICIENT OF HYALURONIC ACID DERIVATIVE AT 790 nm (/M·cm) |
|---|---|---|---|---|
| 1a | 2.3E+03 | 3.0 | 4.5E+04 | 5.4E+05 |
| 1b | 1.8E+03 | 10.6 | 3.5E+04 | 1.9E+06 |
| 1c | 1.6E+03 | 13.2 | 3.2E+04 | 2.4E+06 |
| 1f | 4.7E+02 | 0.1 | 5.8E+03 | 2.3E+04 |
| 1g | 2.4E+03 | 0.4 | 3.0E+04 | 6.8E+04 |
| 1h | 2.3E+03 | 1.5 | 2.9E+04 | 2.7E+05 |
| 1i | 2.0E+03 | 4.3 | 2.5E+04 | 7.7E+05 |
| 1j | 1.1E+03 | 1.8 | 1.3E+04 | 3.2E+05 |
| 1k | 1.4E+03 | 1.0 | 1.7E+04 | 1.8E+05 |
| 1l | 2.1E+03 | 1.5 | 2.6E+04 | 2.7E+05 |
| 1m | 1.4E+03 | 3.1 | 1.8E+04 | 5.6E+05 |
| 1n | 2.3E+03 | 6.9 | 1.4E+05 | 1.2E+06 |
| 2a (GA) | 1.8E+03 | 3.0 | 3.5E+04 | 5.4E+05 |
| 2as (GAs) | 1.8E+03 | 3.0 | 3.5E+04 | 5.4E+05 |
| 2b (GA2) | 2.2E+03 | 2.6 | 4.4E+04 | 4.7E+05 |
| 2d (GA3) | 1.8E+03 | 3.5 | 2.3E+04 | 6.3E+05 |
| 2c (GA4) | 1.5E+03 | 3.2 | 3.0E+04 | 5.8E+05 |
| 2e (GA5) | 1.6E+03 | 8.2 | 3.2E+04 | 1.5E+06 |
| 2f (GA6) | 1.7E+03 | 5.6 | 2.1E+04 | 1.0E+06 |
| 2g (GA7) | 1.7E+03 | 7.3 | 2.1E+04 | 1.3E+06 |

(INTRODUCTION RATIO OF AZIDE MOIETY: ~100%)

NEAR-INFRARED DYE-CONJUGATED HYALURONIC ACID DERIVATIVE AND CONTRAST AGENT FOR OPTICAL IMAGING INCLUDING THEM

TECHNICAL FIELD

The present invention relates to a near-infrared dye-conjugated hyaluronic acid derivatives and a contrast agent for optical imaging including the hyaluronic acid derivative.

BACKGROUND ART

A photoacoustic tomography (hereinafter sometimes abbreviated as "PAT") apparatus has been known as one apparatus for visualizing information on the inside of a living body. In measurement involving using the PAT apparatus, the intensity of a photoacoustic signal emitted from a substance (light absorber) that absorbs light in a body to be measured when the body to be measured is irradiated with light and the time point at which the signal occurs are measured, whereby an image in which a substance distribution in the body to be measured is subjected to an operation can be obtained.

Any light absorber can be used as the light absorber as long as the light absorber absorbs light in the living body to emit an acoustic wave. For example, a blood vessel or malignant tumor in a human body can be used as the light absorber. In addition, a molecule such as indocyanine green (hereinafter sometimes abbreviated as "ICG") can be administered to the body to be utilized as a contrast agent. ICG can be suitably used as a contrast agent in the PAT apparatus because ICG has a small influence when administered to the human body and absorbs light in a near-infrared wavelength region, which has high permeability for the living body, well. It should be noted that the term "ICG" as used herein refers to a compound represented by the following structure.

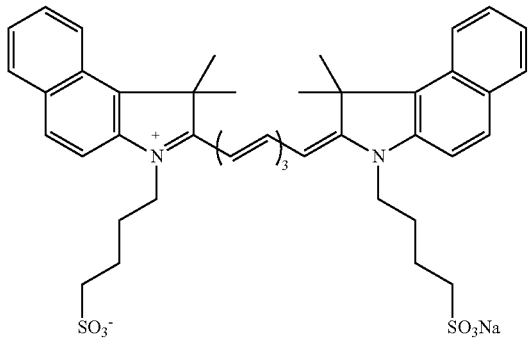

General formula (10)

It should be noted that a counter ion may not be $Na^+$ and an arbitrary counter ion such as $H^+$ or $K^+$ can be used.

In addition, ICG has been used in fluorescence imaging because the compound absorbs near-infrared light to emit near-infrared fluorescence. In other words, ICG is administered to a body to be measured, and after a certain time period, a fluorescence signal emitted from ICG that absorbs light in the body to be measured when the body is irradiated with light from the outside is measured, whereby an ICG distribution in the body to be measured can be imaged. For example, a sentinel lymph node can be visualized.

However, it has been known that the half-life of ICG in blood is about several minutes, which is extremely short.

In view of the foregoing, Non Patent Literature 1 reports an example in which the fluorescence in vivo imaging of a lymph node or a tumor is performed by conjugating a hydrophilic derivative of ICG described above (ICG-OSu) to hyaluronic acid having a molecular weight of 40,000 as a natural polysaccharide to form nanoparticles each having an average particle diameter of 188 nm. The report shows that the derivative remains in blood for a long time period as compared to ICG alone and accumulates in the lymph node or the tumor.

Patent Literature 1 reports an example in which the fluorescence in vivo imaging of a lymph node is performed by conjugating IR783 as a hydrophilic near-infrared dye to hyaluronic acid.

Patent Literature 2 reports a hyaluronic acid derivative to which fluorescein has been covalently conjugated, and the derivative has been used in a method of measuring the activity of a glycosaminoglycan degrading enzyme.

Non Patent Literature 2 reports a nanoparticle of a hyaluronic acid derivative obtained by conjugating polyethylene glycol (hereinafter sometimes abbreviated as "PEG") to hydrophobized hyaluronic acid having a molecular weight of 2,500,000. Further, the literature reports a nanoparticle of a hydrophobized hyaluronic acid derivative in which PEG and a hydrophilic near-infrared dye Cy5.5 are conjugated, the nanoparticle being obtained by covalently conjugating the near-infrared dye to the foregoing nanoparticle, and reports an example of fluorescence in vivo imaging.

CITATION LIST

Patent Literature

PTL 1: US Patent Application Publication 2008/0056999A
PTL 2: Japanese Patent Application Laid-Open No. 2006-25625
PTL 3: Japanese Patent Application Laid-Open No. 2009-155486

Non Patent Literature

NPL 1: H. Mok, et al., Chem. Commun., 48, pp. 8628-8630 (2012)
NPL 2: K. Y. Choi, et al., Biomaterials, 32, pp. 1880-1889 (2011)
NPL 3: T. Hirata, et al., Bioorg. Med. Chem., 6, pp. 2179 (1998)
NPL 4: F. Palumbo, et al., Carbohydrate Polym. 66, pp. 379 (2006)
NPL 5: M. H. Oudshoorn, et al., Polymer, 48, pp. 1915 (2007)
NPL 6: B. Carboni, et al., M. J. Org. Chem., 58, p.p. 3736 (1993)
NPL 7: K. Miki, et al. Biomaterials, 31, pp. 934 (2010)
NPL 8: M. Breidenbach, et al., Proc. Natl. Acad. Sci. USA, 107, pp. 3988 (2010)
NPL 9: G. Huerta-Angeles, et al. Carbohydrate Polym., 84, pp. 1293 (2011)
NPL 10: G. Testa, et al. Int. J. Pharm., 378, pp. 86 (2009)

SUMMARY OF INVENTION

Technical Problem

The ICG content of a compound needs to be high in order that the compound may be used as a contrast agent for optical imaging with high sensitivity. When the ICG content of the compound is low, the amount of ICG to be transported to a target tissue reduces and contrasting sensitivity becomes insufficient. As a result, there arises a need for administering a large amount of the ICG-containing compound. An ICG-containing compound having a high ICG content has been required so that a patient may not shoulder an excessive burden. In addition, it has been desired that the ICG-containing compound has moderate retentivity in blood and can efficiently reach a target tissue such as a tumor.

The ICG content of the compound containing the hydrophilic ICG derivative disclosed in Non Patent Literature 1 is as low as about 10%. In addition, the ratio at which the dye is introduced into the hydrophilic IR783-containing hyaluronic acid derivative disclosed in Patent Literature 1 is unknown and the derivative has not been subjected to any modification with polyethylene glycol for stabilizing the derivative in a living body. In the case of the hyaluronic acid derivative to which fluorescein has been conjugated disclosed in Patent Literature 2, it is difficult to efficiently detect the hyaluronic acid derivative present in the living body because fluorescein is not a near-infrared dye. In addition, 20 equivalents of the dye are loaded with respect to hyaluronic acid having a molecular weight of 40,000. Accordingly, even when a reaction proceeds at 100%, a dye content is at most 20%.

Further, the nanoparticle of the hyaluronic acid derivative disclosed in Non Patent Literature 2 has been modified with polyethylene glycol, but the ratio at which a dye is introduced is unknown and the literature discloses nothing about an optimal value therefor. The foregoing related art discloses nothing about a method and molecular design for the incorporation of a near-infrared dye, e.g., an ICG derivative into hyaluronic acid at a high content, and molecular design for improving its retentivity in blood and tumor accumulation property.

Solution to Problem

The present invention provides a hyaluronic acid derivative, including a polymer formed of units each represented by the following general formula (1), in which: $R^1$'s are independent of each other from unit to unit in the general formula (1); and the polymer contains at least one unit having one of the following general formula (2) and the following general formula (25) as $R^1$ in the general formula (1), and/or at least one unit having the following general formula (3) as $R^1$ in the general formula (1):

General formula (1)

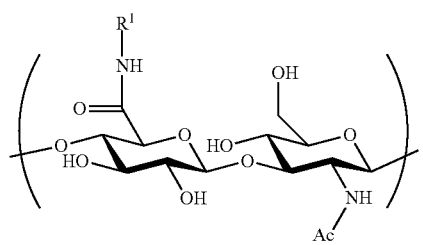

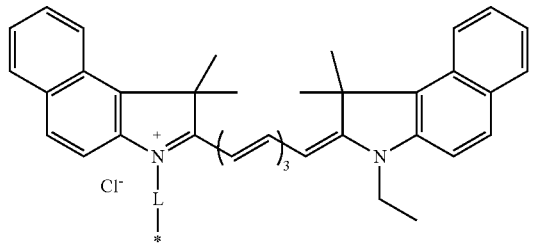

General formula (2)

General formula (25)

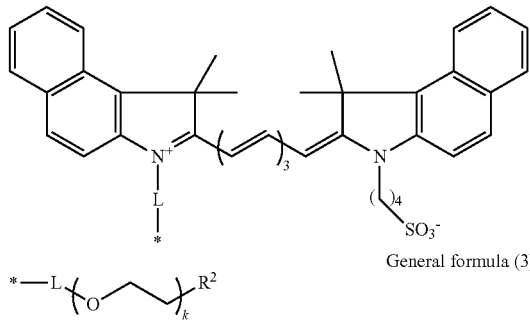

General formula (3)

provided that: in the general formula (2), the general formula (3), and the general formula (25), L's represent linkers independent of each other from unit to unit, and * represents a binding site with N in the general formula (1); and in the general formula (3), $R^2$ represents any one of H, OH, OMe, $NH_2$, and COOH, and k represents an integer of 20 or more and 200 or less.

Further features of the present invention will become apparent from the following description of exemplary embodiments with reference to the attached drawings.

BRIEF DESCRIPTION OF DRAWINGS

FIG. 2 illustrates a synthesis scheme for a hyaluronic acid tetrabutylammonium salt HA-NBu$_4$.

FIG. 3A illustrates a synthesis scheme for a hyaluronic acid derivative 3 having an azide group and FIG. 3B illustrates a scheme for the introduction of an amine having an azide group to hyaluronic acid.

FIG. 13 shows the $^1$H-NMR chart of the derivative 1a.

FIG. 18 shows a summary of the apparent molecular weight of a hyaluronic acid unit, the number of ICG derivatives conjugated to hyaluronic acid, the molecular weight of the entire polymer, and the absorption coefficient of a hyaluronic acid derivative at 790 nm for the compound of the present invention.

DESCRIPTION OF EMBODIMENTS

Figure 1A:
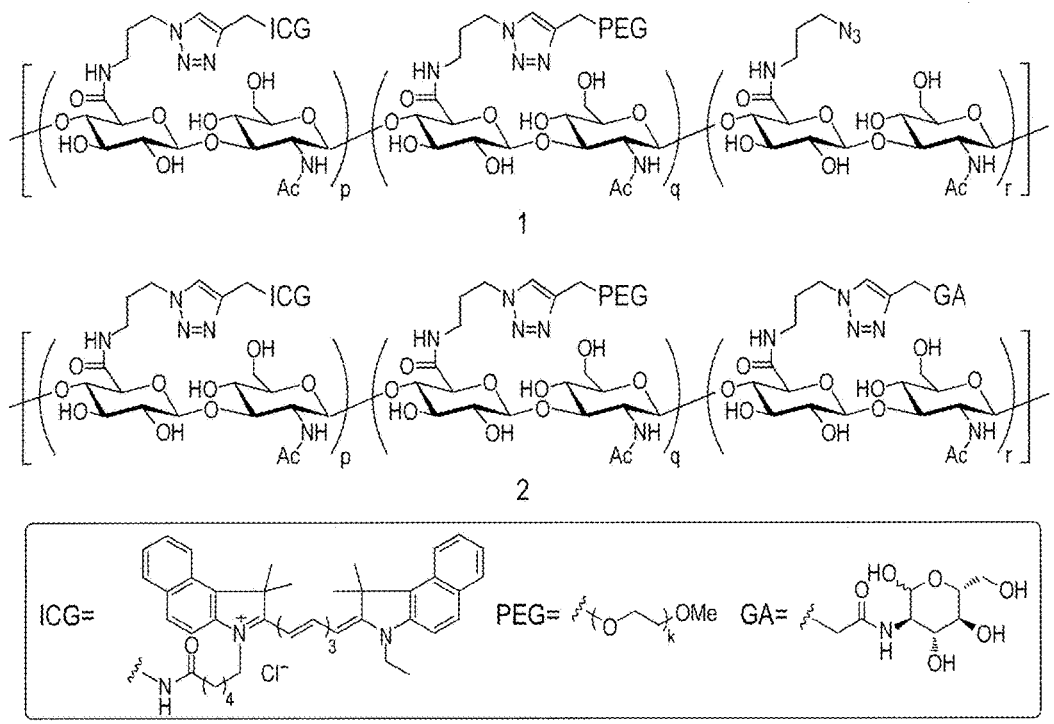
FIG. 1A illustrates a structural formula for a hyaluronic acid derivative containing a near-infrared dye.

An embodiment of the present invention is described. A compound according to this embodiment has a structure in which an ICG derivative is conjugated to hyaluronic acid having PEG, and PEG and the ICG derivative are each conjugated to a carboxyl group present in a glucuronic acid unit of the skeleton of the hyaluronic acid through a linker molecule.

According to one embodiment of the present invention, there is provided a hyaluronic acid derivative, including a polymer formed of units each represented by the following general formula (1), in which: $R^1$'s are independent of each other from unit to unit in the general formula (1); and the polymer contains at least one unit having the following general formula (2) or the following general formula (25) as $R^1$ in the general formula (1), and at least one unit having the following general formula (3) as $R^1$ in the general formula (1):

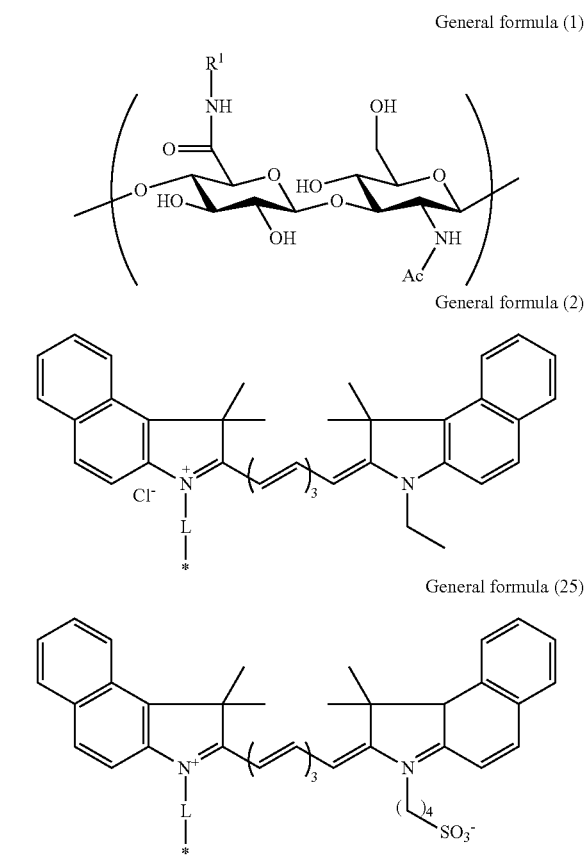

General formula (1)

General formula (2)

General formula (25)

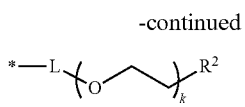

General formula (3)

provided that: in the general formula (2), the general formula (3), and the general formula (25), L's represent linkers independent of each other from unit to unit, and * represents a binding site with N in the general formula (1); and in the general formula (3), $R^2$ represents any one of H, OH, OMe, $NH_2$, and COOH, and k represents an integer of 20 or more and 200 or less.

In addition, the linkers L's in the general formulae (2), (3), and (25) may be identical to or different from each other. Examples of the linker L include a linear or branched alkyl group having 1 to 10 carbon atoms that may be substituted, and structures represented by the following general formulae (22) to (24). A substituent for the alkyl group is, for example, an alkyl group having 1 or more and 3 or less carbon atoms, a halogen atom, or an amino group.

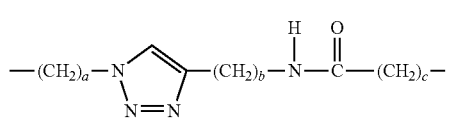

General formula (22)

In the general formula (22), a, b, and c each independently represent an integer of 1 to 10.

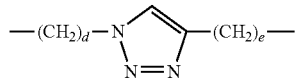

General formula (23)

In the general formula (23), d and e each independently represent an integer of 1 to 10.

General formula (24)

In the general formula (24), f and g each independently represent an integer of 1 to 10.

When the number of units each having the general formula (2) or (25) as $R^2$ is represented by x and the number of all units in the polymer is represented by N, x and N desirably satisfy a relationship represented by the following expression (i).

$0.13 < x/N \le 0.78$  Expression (i)

In addition, when the number of units each having the general formula (3) as $R^1$ is represented by y and the number of all units in the polymer is represented by N, y and N desirably satisfy the following expression (iii).

$0.22 < y/N \le 0.99$  Expression (iii)

According to another embodiment of the present invention, there is provided a hyaluronic acid derivative, including a polymer formed of units each represented by the general formula (1), in which: $R^1$'s are independent of each other from unit to unit in the general formula (1); $R^1$ is selected from the group consisting of the general formulae (2), (3), and (25) and the following general formulae (4), (5), and (29); and the polymer contains at least one unit having the general formula (2) or (25) as $R^1$, and at least one unit having the general formula (3) as $R^1$:

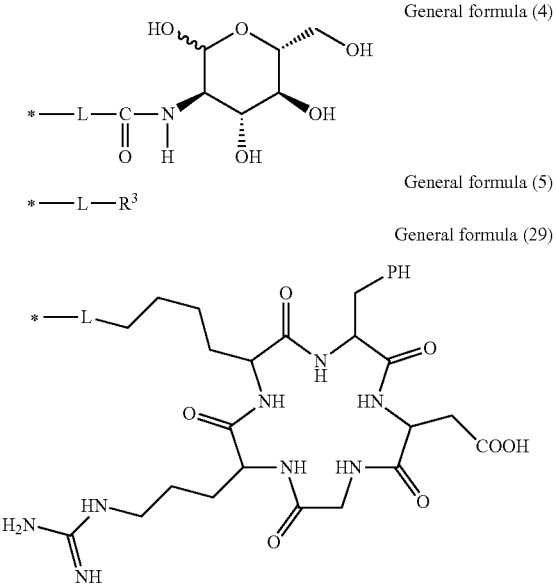

General formula (4)

General formula (5)

General formula (29)

provided that: in the general formulae (2) to (5), (25), and (29), L's represent linkers independent of each other from unit to unit, and * represents a binding site with N in the general formula (1); in the general formula (3), $R^2$ represents any one of H, OH, OMe, $NH_2$, and COOH, and k represents an integer of 20 or more and 200 or less; and in the general formula (5), $R^3$ represents any one of $N_3$, H, $CH_3$, $NH_2$, SH, and COOH. The linkers L's in the general formulae (2) to (5), (25), and (29) may be identical to or different from each other. Examples of the linker L include a linear or branched alkyl group having 1 to 10 carbon atoms that may be substituted, and structures represented by the general formulae (22) to (24). A substituent for the alkyl group is, for example, an alkyl group having 1 or more and 3 or less carbon atoms, a halogen atom, or an amino group.

Further, in the hyaluronic acid derivative according to this embodiment, when the number of units each having the general formula (2) or (25) as $R^1$ is represented by x, the number of units each having the general formula (3) as $R^1$ is represented by y, and the number of units each having the general formula (4) or (29) as $R^1$ is represented by z, x, y, and z desirably satisfy a relationship represented by the following expression (ii).

$0.13 < x/(x+y+z) \le 0.78$  Expression (ii)

In addition, x, y, and z desirably satisfy a relationship represented by the following expression (iii).

$0.22 < y/(x+y+z) \le 0.99$  Expression (iii)

In addition, the hyaluronic acid derivative according to this embodiment preferably contains at least one unit having the general formula (4) or (29) as $R^1$.

According to still another embodiment of the present invention, there is provided a hyaluronic acid derivative, including a polymer formed of units each represented by any one of the general formulae (6) to (9), (28), and (30), in which the polymer contains at least one unit represented by the general formula (6) or (28), and at least one unit represented by the general formula (7).

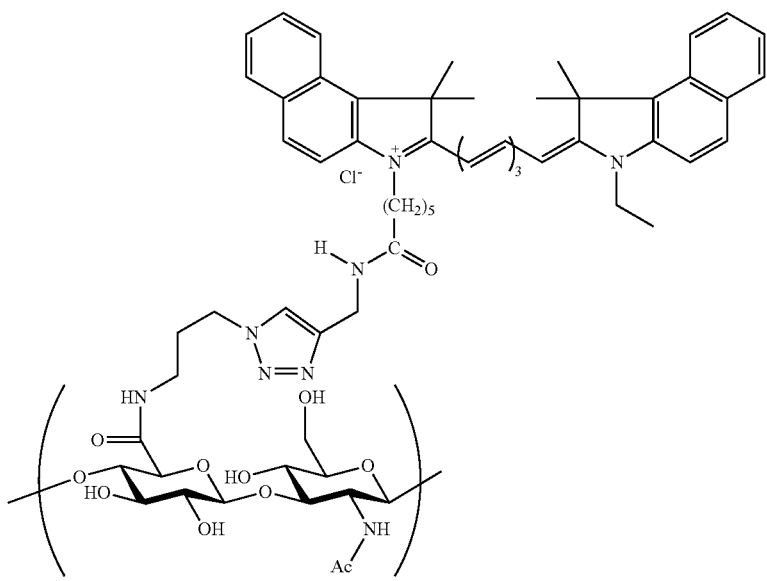
General formula (6)
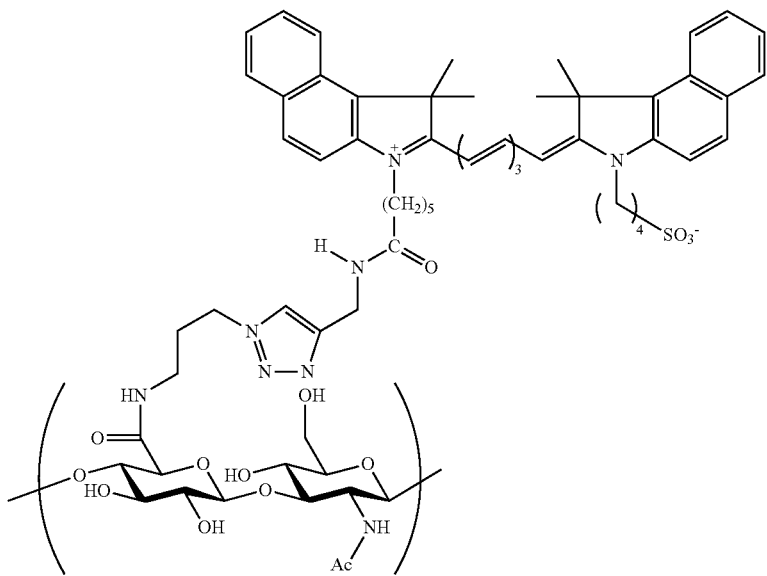
General formula (28)
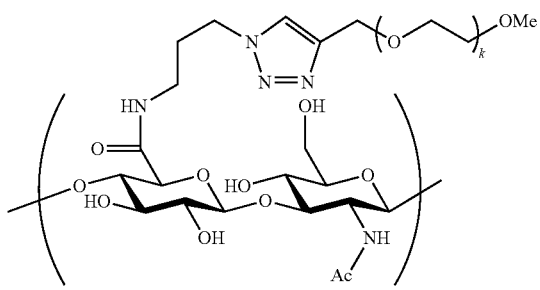
General formula (7)

-continued

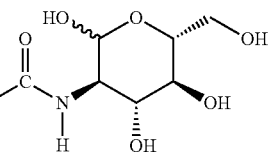
General formula (8)

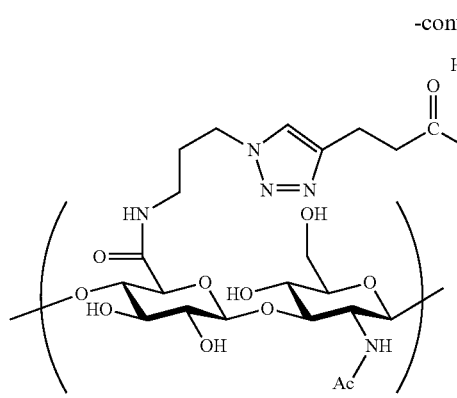

General formula (9)

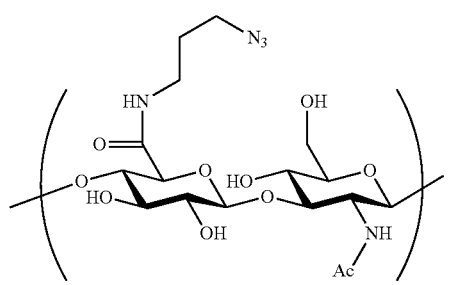

General formula (30)

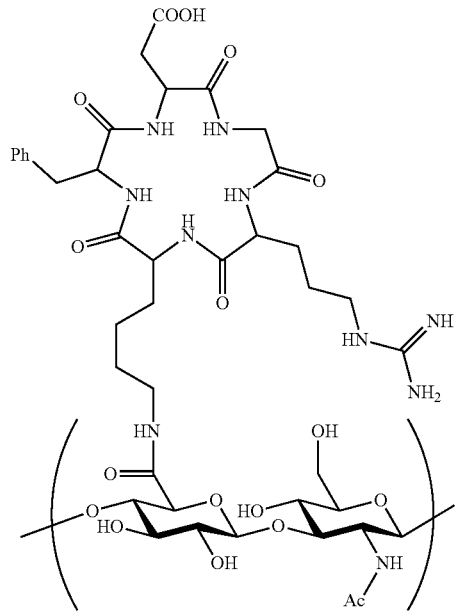

In addition, when the number of units each represented by the general formula (6) or (28) in the polymer is represented by x, the number of units each represented by the general formula (7) in the polymer is represented by y, and the number of units each represented by the general formula (8), (9), or (30) in the polymer is represented by z, x, y, and z preferably satisfy a relationship represented by the following expression (ii).

$$0.13 < x/(x+y+z) \le 0.78 \quad \text{Expression (ii)}$$

In addition, x, y, and z preferably satisfy a relationship represented by the following expression (iii).

$$0.22 < y/(x+y+z) \le 0.99 \quad \text{Expression (iii)}$$

According to still another embodiment of the present invention, there is provided a hyaluronic acid derivative, including a polymer formed of units each represented by the general formula (1) as a main chain, in which: $R^1$'s are independent of each other from unit to unit; and the hyaluronic acid derivative has conjugated thereto an ICG analog or an amphiphilic molecule as $R^1$.

It should be noted that when the number of units each having the ICG analog as $R^1$ is represented by x and the number of all units in the polymer is represented by N, x and N satisfy a relationship represented by the following expression (1).

$$0.13 < x/N \le 0.78 \quad \text{Expression (1)}$$

An embodiment of the present invention includes a particle including the compound of the present invention, a contrast agent for optical imaging including the compound of the present invention and a dispersion medium, and a light contrast agent including the particle and a dispersion medium. Although the size of the particle is not particularly limited, its average particle diameter is preferably 10 nm or more and 180 nm or less, more preferably 10 nm or more and 100 nm or less.

The particle according to the embodiment of the present invention may be of such a particulate shape that multiple molecules of the compound according to the embodiment of the present invention gather, and a dye moiety (ICG derivative) is positioned mainly inside the particle and a PEG moiety is positioned mainly outside the particle.

Hereinafter, details about the embodiment of the present invention are described by way of specific examples.

A compound represented by the general formula (11) or (12) can be given as an example of the hyaluronic acid derivative of the embodiment of the present invention.

In the general formulae (11), (12), and (31), ICG, PEG, and RGD have structures represented by the following general formula (13), the following general formula (14), and the following general formula (32), respectively. In the formula (14), k represents an integer of 20 to 200.

In the formula (11), p represents a fraction of a hyaluronic acid unit having ICG and is a value of more than 0 and less than 100, q represents a fraction of a hyaluronic acid unit having PEG and is a value of more than 0 and less than 100, and r represents a fraction of a hyaluronic acid unit having an azide group and is 0 or a value of more than 0 and less than 100. The total of p, q, and r is 100.

That is, values for x, y, and z in the expression (ii) when the sum of x, y, and z is set to 100 are p, q, and r.

In the general formula (12), GA is the following general formula (15).

In the general formula (31), RGD is the following general formula (32).

In the general formula (12), p represents a fraction of a hyaluronic acid unit having ICG, q represents a fraction of a hyaluronic acid unit having PEG, and r represents a General formula (11)

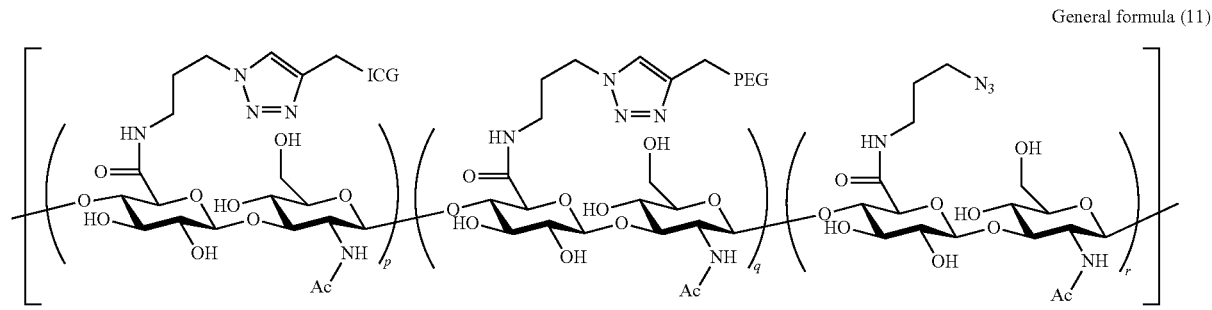

General formula (12)

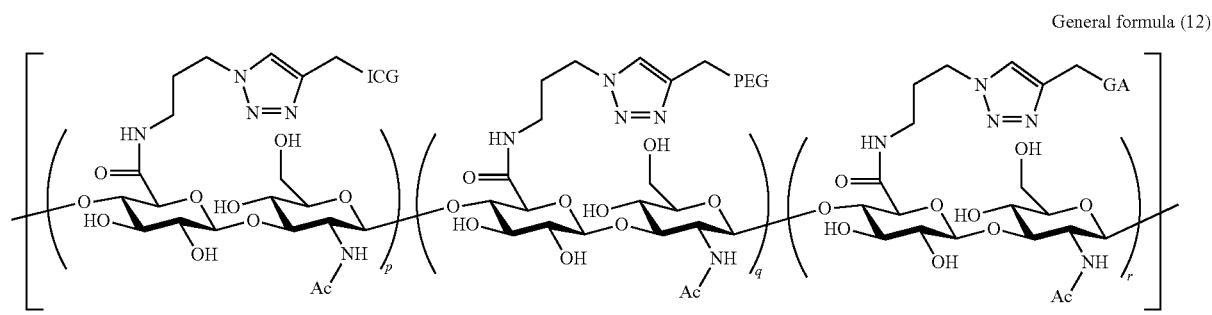

General formula (31)

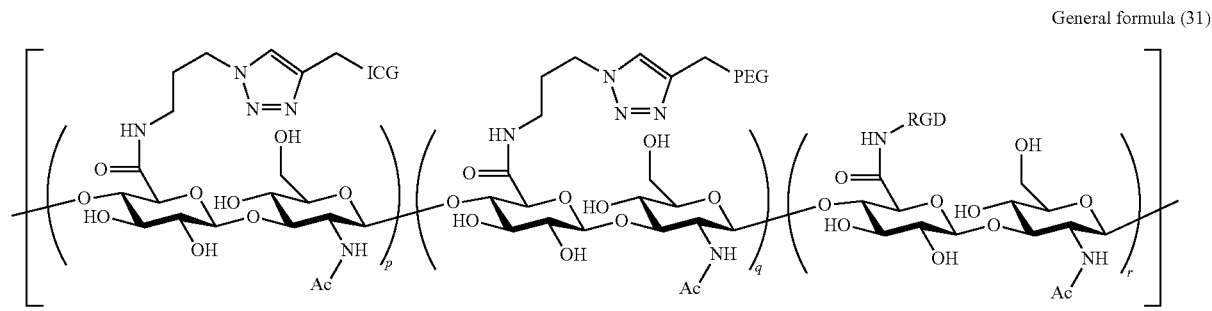

fraction of a hyaluronic acid unit having a glucosamine (hereinafter sometimes abbreviated as "GA") group or the arginine-glycine-aspartic acid (RGD)-peptide (RGD-peptide), p, q, and r are each a value of more than 0 and less than 100, and the total of p, q, and r is 100.

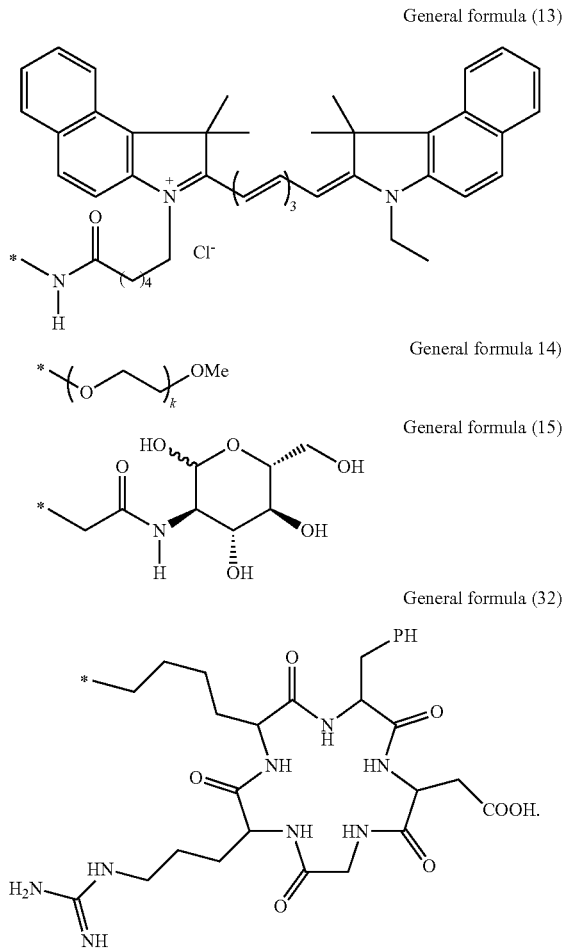

General formula (13)

General formula (14)

General formula (15)

General formula (32)

In the compound according to this embodiment, p in each of the general formulae (11), (12), and (31) is preferably a value of 3 or more and 78 or less, is more preferably 10 or more and 40 or less, and is particularly preferably more than 13.

In the compound according to this embodiment, q in each of the formulae (11), (12), and (31) is 0 or more and 97 or less, and is more preferably 20 or more and 90 or less. As described in Examples, the following tendency was observed: retentivity in blood improved as a PEG content increased. That is, the hyaluronic acid derivative according to the present invention having arbitrary retentivity in blood can be obtained by controlling an ICG content and a PEG content.

(Hyaluronic Acid)

The compound according to this embodiment uses hyaluronic acid as its skeleton. Hyaluronic acids having various molecular weights can be utilized, and the molecular weight preferably falls within the range of 2,500 to 110,000, particularly 5,000 to 25,000. A molecular weight of 50,000 or more results in high viscosity or a reduction in solubility in a solvent, and hence hyaluronic acid obtained by reducing the molecular weight of hyaluronic acid having such molecular weight is suitably used. Hyaluronic acid having a molecular weight of 5,000 to 8,000 is particularly suitable to be used from the viewpoint of the reproducibility of its synthesis.

In the present invention, hyaluronic acid is modified in order that ICG or PEG may be introduced. A hyaluronic acid derivative having an azide group represented by the following general formula (16) can be obtained by conjugating a linker molecule having an azide group to a carboxyl group including glucuronic acid part of hyaluronic acid.

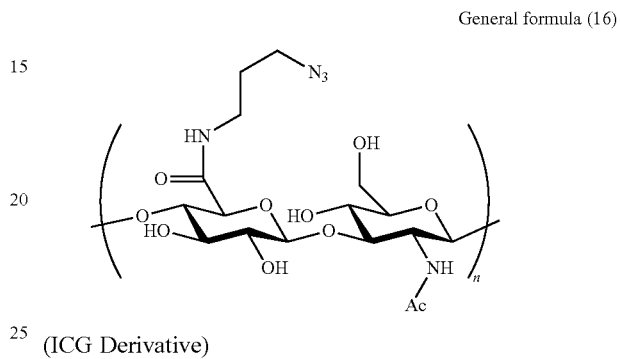

General formula (16)

(ICG Derivative)

In the compound according to this embodiment, an ICG derivative is conjugated to hyaluronic acid. In the description, the ICG derivative as a near-infrared dye refers to a tricarbocyanine-based compound. In this embodiment, the structure of the tricarbocyanine-based compound is represented by, for example, the general formula (17).

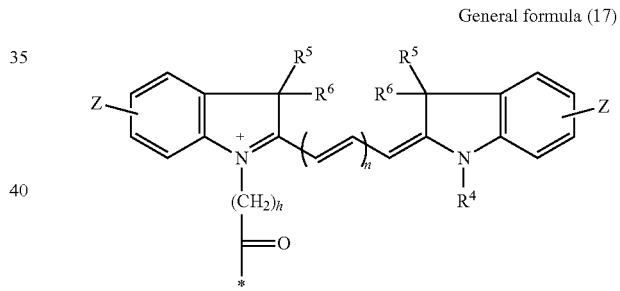

General formula (17)

In the general formula (17), Z represents a hydrogen atom or a sulfo group, or forms a cyclic aromatic ring formed of a benzo[e]indole ring, a benzo[f]indole ring, or a benzo[g]indole ring together with an indole ring bound to Z, and a hydrogen atom of the cyclic aromatic ring may be substituted with an alkyl group having 1 to 10 carbon atoms, an alkoxy group having 1 to 10 carbon atoms, or a sulfo group. Although a structure to which * in the general formula (17) is bound is not particularly limited, an example thereof is a structure bound to nitrogen at the same position of the structure represented by the following general formula (18) or the following general formula (19).

In the general formula (17), $R^4$ represents any one of an alkyl group having 1 to 10 carbon atoms and $-(CH_2)_i-SO_3^-$ (i represents any one of integers of 1 to 10). When $R^4$ represents an alkyl group, a halogen ion or an organic acid ion may be contained as a counter ion. $R^5$ and $R^6$ each independently represent any one of a hydrogen atom, an alkyl group having 1 to 10 carbon atoms, an alkoxy group having 1 to 10 carbon atoms, $-(CH_2)_i-SO_3^-$ (i represents any one of integers of 1 to 10), and $-(CH_2)_i-SO_3X$ (i represents any one of integers of 1 to 10, and X represents any one of sodium, potassium, ammonium, triethylammonium, lysine, and arginine). In the general formula (13), h represents any one of integers of 1 to 10. In the general formula (17), n represents 3.

Preferred examples of the general formula (17) include an ICG derivative (ICG-ATT) represented by the following general formula (18) and an ICG derivative (ICG-S-OSu) represented by the following general formula (26).

General formula (18)

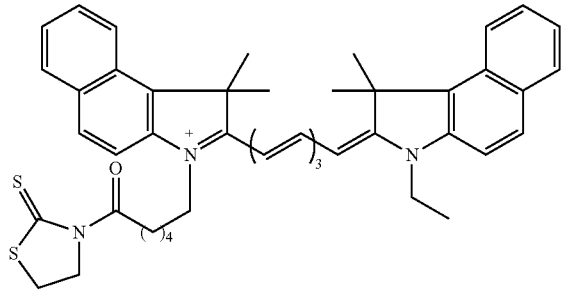

General formula (26)

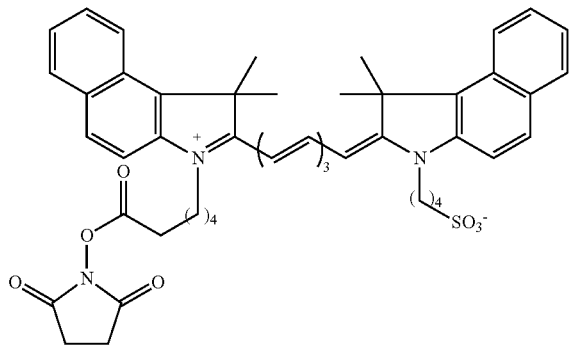

An ICG derivative having an alkyne can be utilized for conjugation of the ICG derivative to hyaluronic acid having an azide group. For example, a compound represented by the following formula (19) or the following formula (27) can be used.

General formula (19)

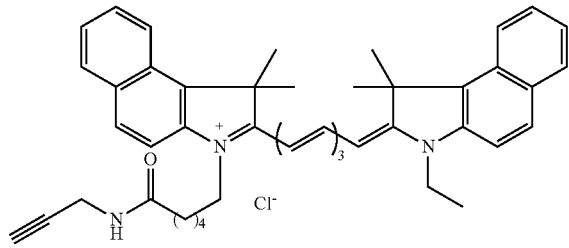

General formula (27)

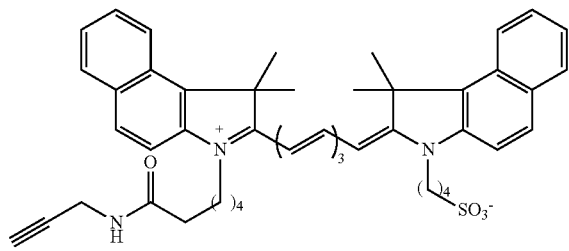

(PEG)

In the compound according to this embodiment, PEG is conjugated to hyaluronic acid. PEG to be used for the preparation of the compound according to this embodiment is a water-soluble polymer and exhibits an effect such as an increase in serum half-life of a protein or a reduction in immunogenicity. In this embodiment, a PEG derivative having an alkyne can be utilized for conjugation of PEG to the hyaluronic acid derivative having an azide group. For example, a compound represented by the following general formula (20) can be used. Although k in the general formula (20) represents the number of repeating units of PEG and is not particularly limited, a compound whose k falls within the range of 20 to 1,000 can be used. k is particularly preferably about 50 to 125. In other words, PEG having a molecular weight in the range of about 1,000 to 40,000, in particular, 2,000 to 5,000 is preferred.

General formula (20)

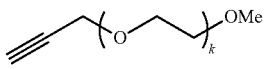

(Targeting Molecule)

In addition, the compound according to this embodiment may contain a targeting molecule that specifically binds to a target site. The targeting molecule in this embodiment is, for example, a substance that specifically binds to a target site such as a tumor or a substance that specifically binds to a substance present around the target site, and can be arbitrarily selected from, for example, a biomolecule and a chemical substance such as a drug. Specific examples thereof include an antibody, an antibody fragment, an enzyme, a bioactive peptide, a glycopeptide, a sugar chain, a lipid, a nucleic acid, and a molecular recognition compound. One kind of those substances can be used alone, or two or more kinds thereof can be used in combination. The use of the compound according to this embodiment to which the targeting molecule has been chemically conjugated enables specific detection of the target site, and the tracking of the dynamics, localization, drug effect, metabolism, and the like of a target substance.

In this embodiment, a targeting molecule having an alkyne can be utilized for conjugation of the targeting molecule to the hyaluronic acid derivative having an azide group. For example, a glucosamine derivative represented by the following general formula (21) can be used. The glucosamine derivative has an affinity for a transporter for glucosamine or a transporter for glucose, and an ability to target a cell expressing any such transporter can be imparted to the compound according to the present invention.

General formula (21)

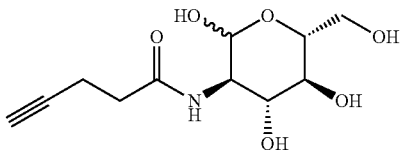

(Method of Preparing Compound)

The compound in this embodiment can be prepared by conjugation of PEG and the ICG derivative to functional groups of the hyaluronic acid derivative by a known coupling reaction. For example, the compound can be prepared by conjugation of PEG and the ICG derivative to azide groups of the hyaluronic acid derivative by a click reaction.

Specifically, an alkynated ICG derivative and an alkynated PEG derivative are subjected to a click reaction with azide groups with which hyaluronic acid has been modified in advance. The alkynated ICG derivative and the alkynated PEG derivative are preferably subjected to the reaction at the same time in order that an ICG content may be increased. When an alkynated targeting molecule is subjected to the reaction in addition to the alkynated ICG derivative and the alkynated PEG derivative, a hyaluronic acid derivative to which ICG and PEG have been conjugated, and to which the targeting molecule has been conjugated can be obtained. The hyaluronic acid derivative to which ICG and PEG have been conjugated can be washed and purified by a known purification method such as a dialysis method, an ultrafiltration method, or a size exclusion column chromatography method. The ICG derivative, PEG, and the targeting molecule may be conjugated to hyaluronic acid through various crosslinkers. For example, the targeting molecule can be conjugated to the hyaluronic acid through a PEG molecule.

(Contrast Agent for Optical Imaging)

The contrast agent for optical imaging according to this embodiment includes the compound according to this embodiment and a dispersion medium. In addition, the contrast agent for optical imaging according to this embodiment may include a pharmacologically acceptable additive such as a vasodilator in addition to the compound according to this embodiment as required.

The dispersion medium is a liquid substance for dispersing the compound according to this embodiment, and examples thereof include physiological saline, distilled water for injection, phosphate-buffered physiological saline, and an aqueous solution of glucose. In the contrast agent for optical imaging according to this embodiment, the compound according to this embodiment may be dispersed in the dispersion medium in advance, or the following may be adopted: the particle according to this embodiment and the dispersion medium are turned into a kit, and then the particle is dispersed in the dispersion medium and used before administration to a living body.

Optical imaging in this embodiment means imaging through irradiation with light. That is, the contrast agent for optical imaging according to this embodiment emits an acoustic wave, fluorescence, or the like when irradiated with light. Photoacoustic imaging can be performed by detecting the emitted acoustic wave and fluorescence imaging can be performed by detecting the emitted fluorescence. It should be noted that the photoacoustic imaging is a concept comprehending photoacoustic tomography. When the contrast agent for optical imaging according to this embodiment is used in the fluorescence imaging, the contrast agent may be called a contrast agent for fluorescence imaging, and when the contrast agent is used in the photoacoustic imaging, the contrast agent may be called a contrast agent for photoacoustic imaging.

When the contrast agent for optical imaging according to this embodiment is administered to a living body, the contrast agent can be accumulated in a larger amount in a tumor site than in a normal site in the living body by utilizing the EPR effect. As a result, when the living body is irradiated with light and an acoustic wave from the living body is detected after the contrast agent for optical imaging according to this embodiment has been administered to the living body, an acoustic wave emitted from the tumor site can be enlarged as compared to an acoustic wave emitted from the normal site.

In addition, the contrast agent for optical imaging according to this embodiment can be used in the contrasting of a blood vessel, a lymph duct, a lymph node, or the like. Further, the contrast agent is particularly preferably used in a contrast agent for a sentinel lymph node. This is because of the following reason: the contrast agent is of a large size as compared to ICG alone, and hence the contrast agent accumulates in the sentinel lymph node with additional ease and an improvement in accumulation property is expected.

(Photoacoustic Imaging Method)

A method of detecting the compound according to this embodiment, which has been administered to a living body, with a photoacoustic imaging apparatus is described. The method of detecting the compound according to this embodiment includes the following steps (a) and (b). It should be noted that the photoacoustic imaging method according to this embodiment may include a step except the following steps:

(a) the step of irradiating a specimen to which the compound according to this embodiment has been administered with light in a wavelength region of 600 nm to 1,300 nm; and (b) the step of detecting an acoustic wave generated from the compound present in the specimen.

In addition, the method of detecting the compound according to this embodiment may include the step of reconstructing a spatial photoacoustic signal intensity distribution from, for example, the wavelength, phase, and time information of the acoustic wave obtained in the step (b). It should be noted that three-dimensional image reconstruction can be performed based on the wavelength, phase, and time information of a photoacoustic signal obtained in the step (b). Data obtained by the image reconstruction may adopt any form as long as the positional information of the intensity distribution of the photoacoustic signal can be grasped from the data. For example, the form may be such that a photoacoustic signal intensity is represented on a three-dimensional space, or may be such that the photoacoustic signal intensity is represented on a two-dimensional plane. Alternatively, the following can be adopted: information on the same object to be observed is acquired by different imaging methods, and then positional correspondence between these pieces of information and the intensity distribution of the photoacoustic signal is acquired.

In the step (a), a specimen to which the compound according to this embodiment has been administered by a method such as oral administration or injection can be used.

In addition, in the step (b), an apparatus for generating light with which the specimen is irradiated and an apparatus for detecting a photoacoustic signal emitted from the compound according to this embodiment are not particularly limited.

A light source for irradiating the specimen with light in the step (b) is not limited as long as the light source can irradiate the specimen with laser pulse light having at least one wavelength selected from the range of 600 nm to 1,300 nm. As an apparatus for irradiating the specimen with laser pulse light, there are given, for example, a titanium sapphire laser (LT-2211-PC, manufactured by LOTIS TII), an OPO laser (LT-2214 OPO, manufactured by LOTIS TII), and an alexandrite laser.

The apparatus for detecting an acoustic wave is not particularly limited and various apparatus can each be used. For example, the detection can be performed with a commercial photoacoustic imaging apparatus (Nexus 128 manufactured by Endra Inc.).

The imaging method involving using the compound according to this embodiment enables the contrasting of a target site such as a tumor, a lymph node, or a blood vessel through the steps (a) and (b).

(Method of Producing Hyaluronic Acid Derivative)

A method of producing a hyaluronic acid derivative in this embodiment is characterized by including causing an ICG derivative and hyaluronic acid to react with each other in the presence of an amphiphilic molecule. The amphiphilic molecule is preferably polyethylene glycol.

When an ICG analog is conjugated to hyaluronic acid, the presence of the amphiphilic molecule suppresses the aggregation of hyaluronic acid. As a result, a large amount of the ICG derivative is conjugated to hyaluronic acid.

Hereinafter, the present invention is described by way of Examples in order that the features of the present invention may be additionally elucidated. However, the present invention is not limited by Examples. It should be noted that carbon atoms and hydrogen atoms are omitted from chemical structural formulae represented in the description and drawings in some cases according to a conventional representation method.

Example 1: Synthesis of Hyaluronic Acid Derivative Containing Near-Infrared Dye

Hyaluronic acid derivatives 1 and 2 were synthesized according to the following scheme (FIG. 1A). Six kinds of low-molecular weight hyaluronic acid sodium salts (HA-Na) having different molecular weights were used as starting materials (molecular weight MW(HA-Na)=2.5K, 5K, 8K, 25K, 50K, and 110K). It should be noted that a Micro Hyaluronic Acid FCH manufactured by Kikkoman Biochemifa Company and a Hyaluronic Acid FCH manufactured by Kikkoman Biochemifa Company were utilized as HA-Na having molecular weights of 2.5K and 110K. In addition, the Hyaluronic Acid FCH (having a molecular weight of 110K) reduced in molecular weight by employing a known approach (Patent Literature 3) was used as each of the other starting materials, i.e., the HA-Na having molecular weights of 5K, 8K, 25K, and 50K.

HA-Na having molecular weights of 5K, 8K, 25K, and 50K were obtained through a molecular weight reduction based on the following approach. 5.2 Grams (13 mmol) of an HA-Na were dissolved in pure water (150 mL). A 6.6 N aqueous solution of HCl (15 ml) was added to the solution and then the mixture was stirred at 70° C. After a predetermined time period, the mixture was neutralized with a 10% aqueous solution of NaOH and then the solvent was removed by evaporation. The resultant white solid was dissolved in water and then the solution was dialyzed for 24 hours with a dialysis membrane having a molecular weight cut-off of 1K (Spectra/Por 6 manufactured by Spectrum Laboratories, Inc.). Subsequently, the resultant was freeze-dried to provide 2.9 g (55%) of the HA-Na as a white solid. HA-Na having molecular weights of 5K, 8K, 25K, and 50K are obtained by performing acid treatment for the HA-Na for reaction times of 6 hours, 4 hours, 3 hours, and 2 hours, respectively.

The molecular weight of hyaluronic acid was determined by size exclusion chromatography. Measurement conditions are as follows: eluent: a 0.2 M aqueous solution of NaCl, flow rate: 0.5 ml/min, column: a Shodex SB-803 HQ (manufactured by Showa Denko K.K.), standard substance: pullulan (STD-P Series manufactured by Showa Denko K.K.). It should be noted that low-molecular weight hyaluronic acid (FCH-SU, molecular weight: 110K) and Micro Hyaluronic Acid FCH (molecular weight: 2.5K) purchased from Kikkoman Biochemifa Company each showed the corresponding number-average molecular weight under the conditions.

Example 1(1): Synthesis of Near-Infrared Light-Emitting Compound ICG-Alkyne

Figure 1B:
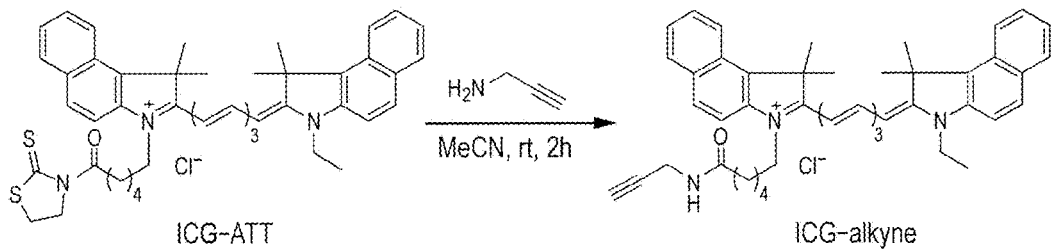
FIG. 1B illustrates a synthesis scheme for a near-infrared light-emitting compound ICG-alkyne.
Figure 1C:
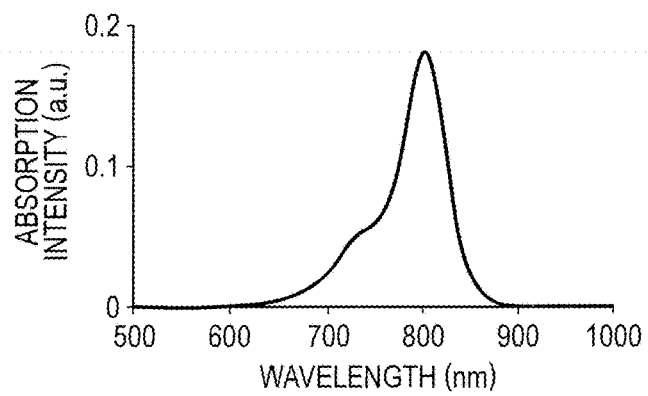
FIG. 1C shows the UV-visible-near-infrared absorption spectrum of ICG-alkyne.

FIG. 1B illustrates a synthetic scheme for a near-infrared light-emitting compound ICG-alkyne. Details are as described below. 0.10 Gram (0.32 mmol) of a known indocyanine green derivative ICG-ATT (Non Patent Literature 3) was loaded into a 50-ml one-necked round-bottom flask and then dissolved in 2 ml of acetonitrile. Propargylamine (25 µL, 0.39 mmol) was added to the solution at 0° C. and then the mixture was stirred for 2 hours. 10 Milliliters of a 0.1 N hydrochloric acid were added to the solution and then an aqueous layer was extracted with $CH_2Cl_2$. The organic layer was washed with a saturated saline solution and then dried with magnesium sulfate. The solvent was removed by evaporation under reduced pressure and then the resultant dark green solid was purified by centrifugal sedimentation ($CH_2Cl_2/Et_2O$). The dark green solid was washed with a small amount of ethyl acetate and then dried under reduced pressure. After that, 82 mg (82%) of ICG-alkyne were obtained as a dark green solid. Its identification was performed by $^1$H-NMR and FAB-MS. The results were as follows: $^1$H-NMR (400 MHz, $CDCl_3$, 25° C., TMS) δ/ppm; 1.47 (t, J=6.9 Hz, 3H), 1.57-1.70 (m, 2H), 1.78-1.86 (m, 2H), 1.86-1.96 (m, 2H), 1.96 (s, 6H), 2.00 (s, 6H), 2.15 (t, J=2.4 Hz, 1H), 2.42 (t, J=7.3 Hz, 2H), 4.04 (dd, J=2.4, 5.4 Hz, 2H), 4.10-4.28 (m, 4H), 6.11-6.20 (m, 1H), 6.40-6.58 (m, 1H), 6.62-6.76 (m, 1H), 6.85-6.96 (m, 1H), 7.04-7.13 (m, 1H), 7.31 (d, J=8.8 Hz, 2H), 7.39 (d, J=8.8 Hz, 1H), 7.43-7.49 (m, 2H), 7.56-7.63 (m, 2H), 7.88-7.97 (m, 6H), 8.06-8.14 (m, 2H); FAB-HRMS m/e 660.3964 [M]$^+$. It should be noted that the light absorption spectrum of ICG-alkyne in a near-infrared region is as shown in FIG. 1C (solvent: chloroform ($1.0 \times 10^{-6}$ M)). The compound has an absorption maximum at 802 nm. The compound had a molar absorption coefficient of $1.8 \times 10^5$ ($M^{-1}cm^{-1}$).

Example 1(2): Synthesis of Hyaluronic Acid Tetrabutylammonium Salt HA-NBu$_4$

A high-molecular weight HA-Na has a low solubility in an organic solvent and is hence transformed into the corresponding ammonium salt to be subjected to various transformation reactions (Non Patent Literature 4 and Non Patent Literature 5). A low-molecular weight hyaluronic acid sodium salt HA-Na utilized in the present invention was also hardly soluble in an organic solvent, and hence the HA-Na was similarly transformed into an ammonium salt and then utilized in a condensation reaction. The outline of the synthesis of a hyaluronic acid tetrabutylammonium salt HA-NBu$_4$ is described below (FIG. 2). 0.80 Gram of the low-molecular weight hyaluronic acid sodium salt HA-Na (MW(HA-Na)=8K, 2.0 mmol in terms of minimum unit) was loaded into a 100-ml one-necked round-bottom flask and then dissolved in 5 ml of water. A cation exchange resin DOWEX (1.9 g, corresponding to 4.0 mmol) subjected to cation exchange with tetrabutylammonium hydroxide was added to the solution, and then the mixture was stirred at room temperature overnight. After the DOWEX had been removed with a glass filter, the filtrate was freeze-dried to provide 1.1 g (85%) of the hyaluronic acid tetrabutylammonium salt HA-NBu$_4$ as a white solid. Its identification was performed by $^1$H-NMR ($^1$H-NMR (400 MHz, $D_2O$, 25° C.)

δ/ppm; 0.81-0.85 (br m, 12H), 1.22-1.27 (br m, 8H), 1.53-1.54 (br m, 8H), 1.88 (s, 3H), 3.06-3.10 (br m, 8H), 3.31-3.92 (m, 10H), 4.45 (br s, 2H)).

Similar reactions were performed with HA-Na having molecular weights of 2.5K and 5K to provide their corresponding products. Their yields were 83% and 99%, respectively. However, HA-Na having molecular weights of 25K, 50K, and 110K each have poor water solubility, and hence the amount of water to be used needs to be increased in order that their corresponding ammonium salts may be obtained. Their yields were 62%, 68%, and 64%, respectively.

Example 1(3): Synthesis of Hyaluronic Acid Derivative 3 Having Azide Group

Figure 12:
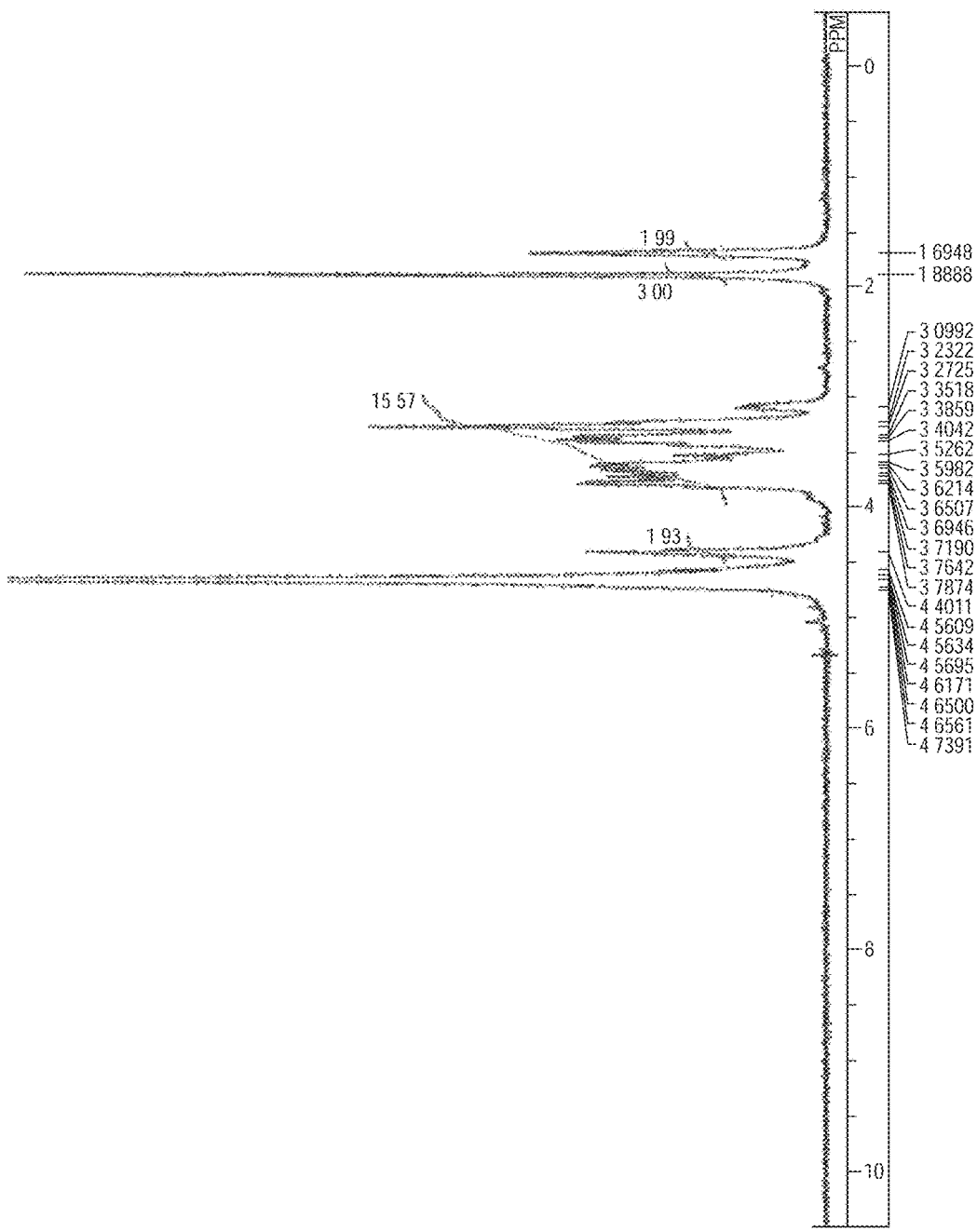
FIG. 12 shows the $^1$H-NMR chart of the derivative 3 (the transformation ratio of carboxyl groups is more than 99%).

The synthesis of a hyaluronic acid derivative 3 having an azide group serving as a scaffold for modification with a near-infrared dye, PEG, GA, or the like is described below (FIG. 3A). Under $N_2$ atmosphere, 0.25 g of the HA-NBu$_4$ (MW(HA-Na)=8K, 0.40 mmol in terms of minimum unit) was loaded into a 50-ml Schlenk flask and then dissolved in 4.0 ml of anhydrous DMSO. 1.7 Grams (3.2 mmol) of (benzotriazol-1-yloxy)tripyrrolidinophosphonium hexafluorophosphate (PyBOP) and 0.43 g (3.2 mmol) of 1-hydroxybenzotriazole (HOBt) were added to the solution. After that, 0.64 g (6.4 mmol) of 3-azido-1-propylamine (Non Patent Literature 6) was added and the mixture was stirred at room temperature for 20 hours. Water was added to the solution, the aqueous layer was washed with $CH_2Cl_2$, and the aqueous layer was dialyzed with a dialysis membrane having a molecular weight cut-off of 3.5K for 24 hours. Subsequently, the resultant was freeze-dried to provide 0.13 g (70%) of the hyaluronic acid derivative 3 having an azide group as a white solid. Its identification was performed by $^1$H-NMR ($^1$H-NMR (400 MHz, $D_2O$, 25° C.) δ/ppm; 1.67 (s, 2H), 1.87 (s, 3H), 3.05-3.80 (m, 14H), 4.37 (m, 2H)). FIG. 12 shows the NMR chart of the derivative 3 as a typical example.

Similar reactions were performed with the HA-Na having molecular weights of 2.5K, 5K, 25K, 50K, and 110K to provide their corresponding products. Their yields were 85%, 66%, 99%, 99%, and 99%, respectively (the transformation ratio of carboxyl groups was more than 99%). However, in the reaction of an HA-NBu$_4$ having a molecular weight of 2.5K or 110K under the same conditions, the reproducibility of the transformation ratio of carboxyl groups is poor. In addition, the reaction of the HA-NBu$_4$ having a molecular weight of 110K requires the use of 15 ml of DMSO and its reactivity to a condensation reaction is low as compared to any other salt. It was found from those results that a molecular weight of 5K to 50K was preferred in the synthesis of the hyaluronic acid derivative containing a near-infrared dye of the present invention.

Example 1(4): Regulation of Ratio at which Amine Having Azide Group is Introduced into Hyaluronic Acid As described in Example 1(3), carboxyl groups in hyaluronic acid can be transformed in a substantially complete manner by setting the numbers of equivalents of 3-azido-1-propylamine and a condensation agent to be used to 16 equivalents and 8 equivalents, respectively. Meanwhile, the introduction efficiency of 3-azido-1-propylamine can be regulated by reducing the numbers of equivalents of 3-azido-1-propylamine and the condensation agent to be used (FIG. 3B and Table 1). It should be noted that braces in FIG. 3B show that 3-azido-1-propylamine is introduced at random. The introduction efficiency of 3-azido-1-propylamine was calculated from a ratio between 3H (1.87 ppm) of an N-acetyl group in hyaluronic acid and 2H (1.67 ppm) at the 2-position of 3-azido-1-propylamine to be introduced. In addition, a yield was determined with a molecular weight calculated based on the introduction efficiency determined by $^1$H-NMR.

TABLE 1

Synthesis of hyaluronic acid derivative 3 having azide group

| Entry No. | Number of equivalents | Yield (%) | l:m$^a$ |
|---|---|---|---|
| 1 | 12 | 50 | >99:<1 |
| 2 | 8 | 56 | 97:3 |
| 3 | 6 | 52 | 90:10 |
| 4$^b$ | 6 | 64 | 93:7 |
| 5 | 4 | 65 | 79:21 |
| 6 | 2 | 50 | 75:25 |
| 7 | 1.5 | 47 | 66:34 |
| 8$^c$ | 1.5 | 49 | 65:35 |
| 9 | 1.25 | 52 | 53:47 |
| 10 | 1 | 58 | 42:58 |
| 11 | 0.75 | 59 | 20:80 |
| 12 | 0.5 | 55 | 16:84 |

$^a$Calculated from the integrated value of $^1$H-NMR.
$^b$HOBt•H$_2$O was used instead of HOBt.
$^c$The same conditions as those of the entry 7. Confirmation of reproducibility.

Figure 4A:
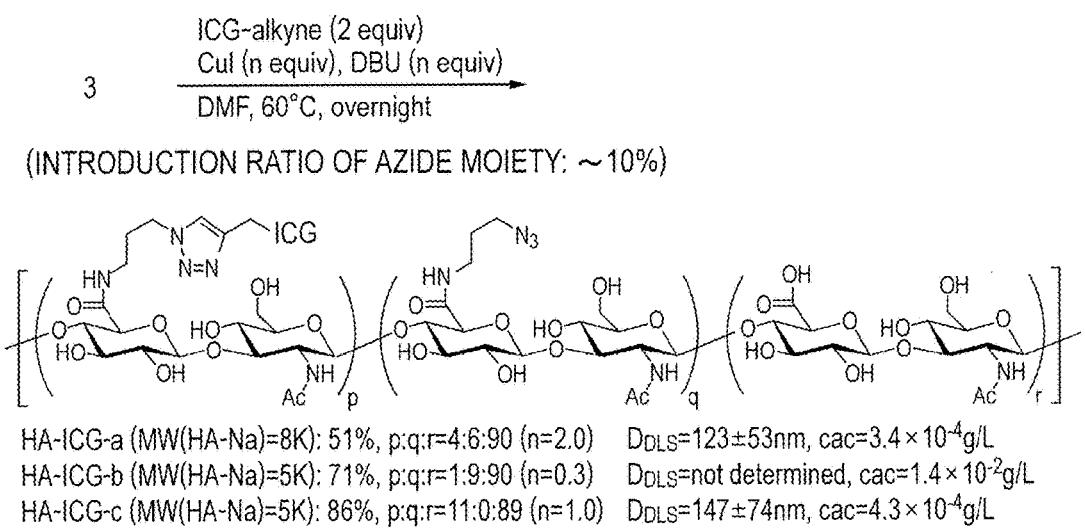
FIG. 4A illustrates a synthesis scheme for a hyaluronic acid derivative HA-ICG having only ICG.

Comparative Example 1: Synthesis of Hyaluronic Acid Derivative HA-ICG Having ICG The synthesis of a hyaluronic acid derivative HA-ICG having only ICG as Comparative Example is described below (FIG. 4A). Under $N_2$ atmosphere, 41 mg of the derivative 3 (MW(HA-Na)=8K, 0.10 mmol in terms of minimum unit, azidation efficiency: ~10%) were loaded into a 25-ml Schlenk flask and then dissolved in 2 ml of anhydrous DMF. After 14 mg (20 μmol) of ICG-alkyne had been added to the solution, 3.8 mg (20 μmol) of CuI and 3.0 mg (20 μmol) of 1,8-diazabicyclo[5.4.0]undec-7-ene (DBU) were added to the mixture, and then the whole was stirred at 60° C. overnight. 2 Milliliters of water were added to the solution and then the mixture was dialyzed with a dialysis membrane having a molecular weight cut-off of 1K for 24 hours against water. The resultant aqueous solution was filtered with a filter (pore diameter: 0.45 μm) and then freeze-dried to provide 22 mg (51%) of a hyaluronic acid derivative HA-ICG-a having ICG as a pale green solid. The identification of the derivative HA-ICG-a was performed by $^1$H-NMR ($^1$H-NMR (400 MHz, $D_2O$, 25° C.) δ/ppm; 1.60-1.70 (m, 0.23H), 1.89 (br s, 3H), 3.20-3.85 (m, 11H), 4.30-4.50 (m, 2H)).

It should be noted that the introduction ratio of an ICG moiety was determined as follows: the UV spectrum of a DMF-H$_2$O (1:1) mixed solution of the hyaluronic acid derivative having ICG was measured and then the ratio was determined based on an absorbance at its maximum absorption wavelength (around 790 nm) by using ICG-alkyne as a standard substance. In addition, a yield was determined with a molecular weight calculated based on the introduction ratio of an ICG moiety. An HA-ICG-b had a low introduction ratio of an ICG moiety (the introduction ratio per molecule was 1%), and hence no particle formation was observed (nearly no scattering light was observed in dynamic light scattering (DLS)).

Figure 15:
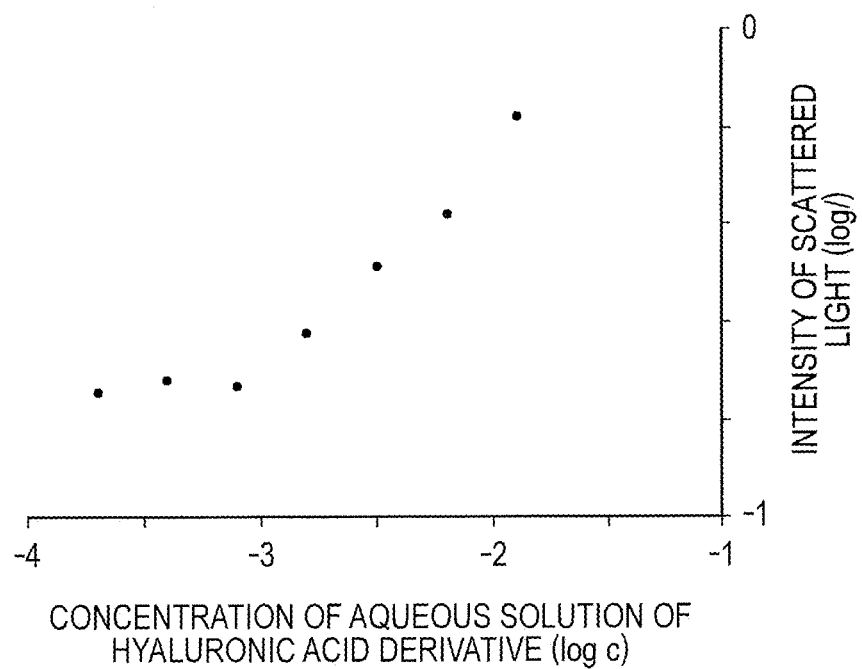
FIG. 15 shows a relationship between the concentration of an aqueous solution of the hyaluronic acid derivative 1a and the intensity of scattered light.

When the amounts of the copper compound and DBU are each set to 1 equivalent or less, nearly no ICG moiety is introduced. In addition, the reaction is poor in reproducibility and no ICG moiety is introduced in many cases. Although a similar reaction proceeds by using the derivative 3 having a molecular weight of 5K, the reaction is similarly poor in reproducibility. The measurement of the particle diameter of a self-assembly formed by a hyaluronic acid derivative by DLS was performed with an FPAR-1000 manufactured by Otsuka Electronics Co., Ltd. The sample was dissolved in Milli-Q water and the solution was filtered with a PVDF filter (pore diameter: 0.45 μm) before the measurement (sample concentration: 1 to 2 g/L). Scattering light measurement at a scattering angle of 90° was performed at 25° C. for 3 minutes. Reproducibility was confirmed by performing the measurement three times. The determination of the critical aggregation concentration (cac) of the self-assembly formed by the hyaluronic acid derivative by static light scattering (SLS) was performed with an SLS-6000 manufactured by Otsuka Electronics Co., Ltd. The sample was dissolved in Milli-Q water and the solution was filtered with a PVDF filter (pore diameter: 0.45 μm) before the measurement. The scattering light measurement at a scattering angle of 90° of each of aqueous solutions of the hyaluronic acid derivative having various concentrations was performed at 25° C. for 3 minutes. Reproducibility was confirmed by performing each measurement three times. FIG. 15 shows typical results of the SLS measurement.

The particle diameter of the hyaluronic acid derivative measured by DLS was about 120 to 150 nm. The particle diameter of the HA-ICG-b having a low ICG introduction ratio could not be measured. The cac values of the HA-ICG-a and an HA-ICG-c were extremely small and hence the derivatives were found to form stable particles even in a dilute environment.

Example 1(5): Synthesis of Hyaluronic Acid Derivative 1 Having ICG and PEG

Figure 4B:
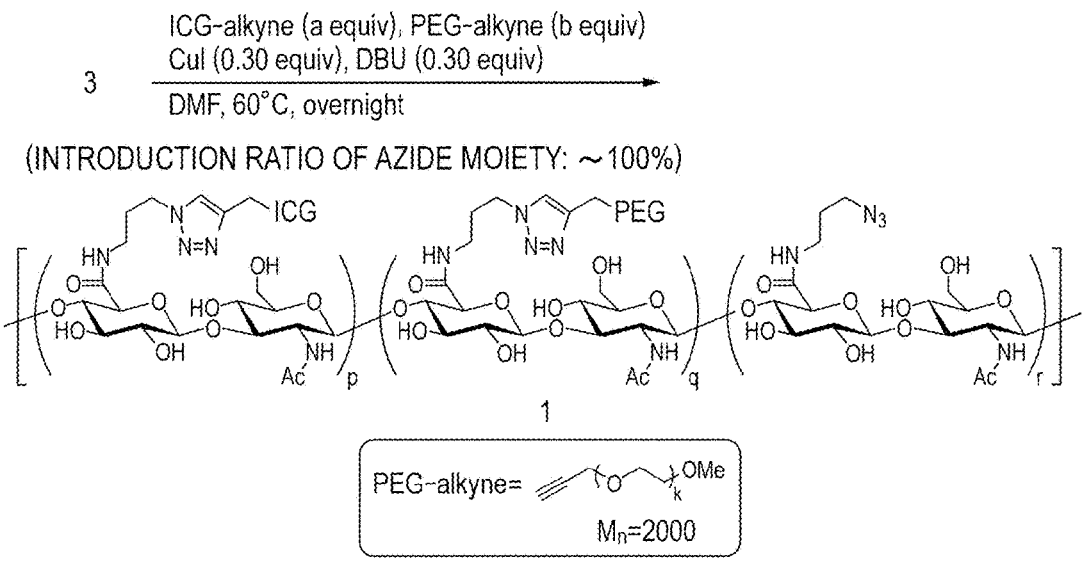
FIG. 4B illustrates a synthesis scheme for a hyaluronic acid derivative 1 having ICG and PEG.
Figure 13:
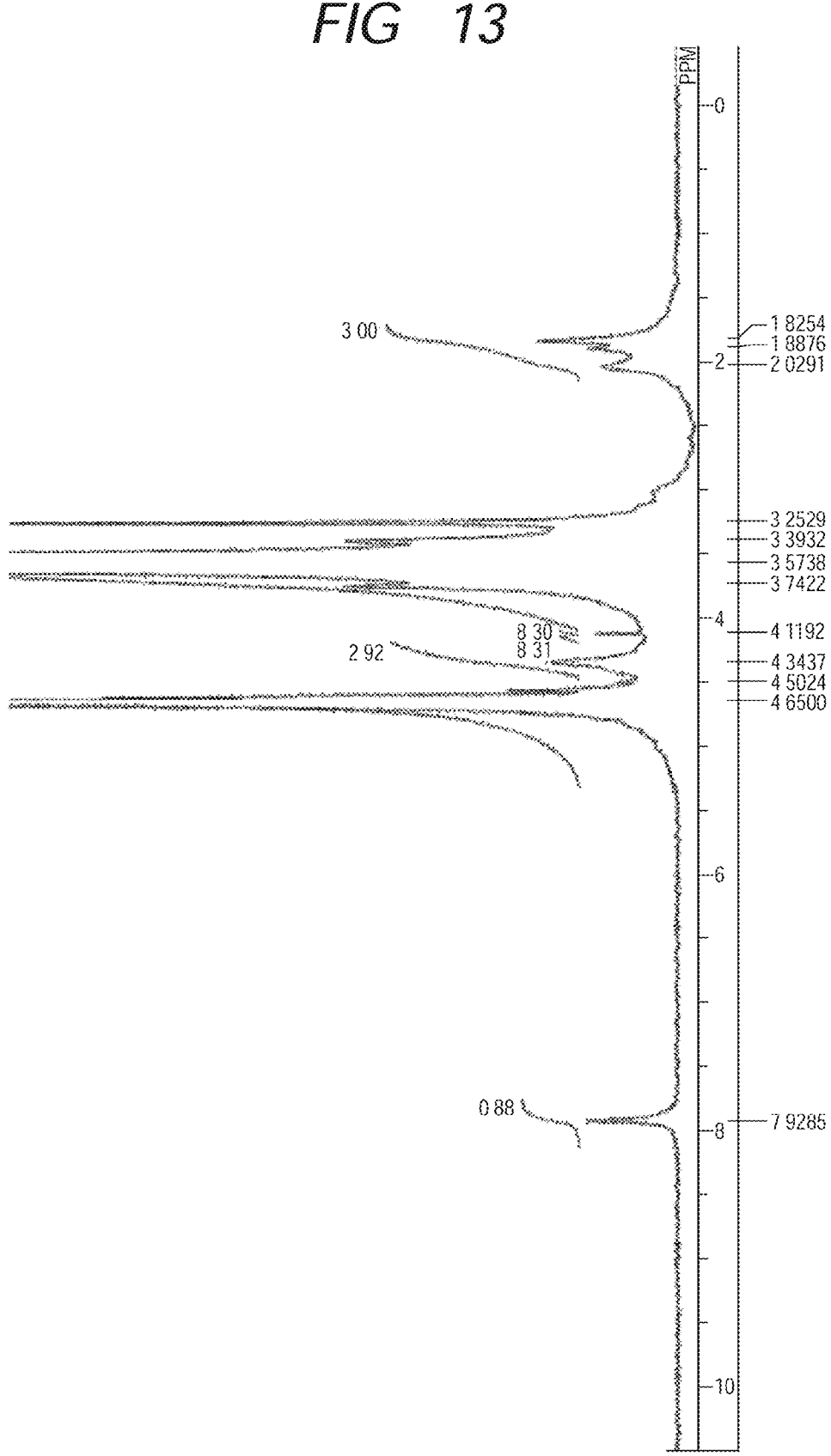

Various hyaluronic acid derivatives 1 each having ICG and PEG can each be obtained by simultaneously conjugating ICG-alkyne and PEG-alkyne (Non Patent Literature 7) to the hyaluronic acid derivative 3 having an azide group (FIG. 4B and Table 2). A typical synthetic example is described below. Under $N_2$ atmosphere, 23 mg of the derivative 3 (MW(HA-Na)=8K, 50 μmol in terms of minimum unit, azidation efficiency: >99%) were loaded into a 25-ml Schlenk flask and then dissolved in 2 ml of anhydrous DMF. After 8.8 mg (13 μmol) of ICG-alkyne and 0.18 g (88 μmol) of PEG-alkyne had been added to the solution, 2.9 mg (15 μmol) of CuI and 2.3 mg (15 μmol) of DBU were added to the mixture, and then the whole was stirred at 60° C. overnight. 2 Milliliters of water were added to the solution and then the mixture was dialyzed with a dialysis membrane having a molecular weight cut-off of 25K for 24 hours against water. The resultant aqueous solution was filtered with a filter (pore diameter: 0.45 μm) and then freeze-dried to provide 48 mg (60%) of a hyaluronic acid derivative 1 having ICG and PEG as a deep green solid. Its identification was performed by $^1$H-NMR ($^1$H-NMR (400 MHz, $D_2O$, 25° C.) δ/ppm; 1.80-2.15 (m, 3H), 3.10-3.90 (m, 183H), 4.30-4.50 (m, 2H), 7.93 (br s, 0.96H)). FIG. 13 shows the $^1$H-NMR chart of the derivative 1 as a typical example.

It should be noted that the conversion ratio of a cyclization reaction was calculated based on the reduction ratio of 2H (1.67 ppm) at the 2-position of 3-azido-1-propylamine by $^1$H-NMR. The introduction ratio of an ICG moiety was determined as follows: the UV spectrum of a DMF solution of a hyaluronic acid derivative having ICG and PEG was measured and then the ratio was determined based on an absorbance at its maximum absorption wavelength (around 790 nm) by using ICG-alkyne as a standard substance. The introduction ratio of a PEG moiety was calculated from the conversion ratio of azide groups and the introduction ratio of an ICG moiety. In addition, a yield was determined with a molecular weight calculated based on the introduction ratios of ICG and PEG moieties.

As shown in Table 2, a hyaluronic acid derivative having a high ICG introduction ratio was obtained. On the other hand, as described in Comparative Example 1 (synthesis of the hyaluronic acid derivative HA-ICG having ICG) described above, an attempt was made to synthesize a hyaluronic acid derivative having only ICG by conjugating ICG-alkyne to the hyaluronic acid derivative 3 having an azide group without using PEG-alkyne, but it was difficult to synthesize a hyaluronic acid derivative having a high ICG introduction ratio and the introduction ratio was limited to at most about 10%. In other words, it was found that: the introduction of PEG to hyaluronic acid was essential for the acquisition of a hyaluronic acid derivative having a high ICG introduction ratio; and it was important to react ICG-alkyne and PEG-alkyne with 3 at the same time. In addition, the derivative had a particle diameter measured by DLS of about 100 to 200 nm and was found to satisfy a condition as a tumor-targeting agent based on the EPR effect.

It should be noted that hyaluronic acid derivatives 1b, 1c, and 1d having ICG introduction ratios of 53%, 66%, and 78% are hardly water-soluble. It was possible to form a particle of the derivatives 1b and 1c by dispersing a DMF solution of them in water. However, even when the derivative 1d was prepared by the same approach, a water-insoluble solid precipitated and hence it was difficult to uniformly dissolve the entire sample. The polymer in the aqueous solution after the removal of the insoluble solid corresponded to a yield of 66% (an ICG content of 57%), and hence it is assumed that the hyaluronic acid derivative having a high ICG content became water-insoluble and precipitated. Meanwhile, no particle formation in water could be observed in the case of a hyaluronic acid derivative 1e having an ICG introduction ratio of 0%, i.e., modified only with PEG, but the formation of a particle having a diameter of 157 nm was able to be observed in the case of a hyaluronic acid derivative 1f having an ICG introduction ratio of 1%. In view of the foregoing, it can be said that an ICG introduction ratio required for a hyaluronic acid derivative modified with ICG and PEG to form a nanoparticle in water is about 1% to 65%.

It was found that the cac of a derivative having a molecular weight of 5K was entirely smaller than that of a derivative having a molecular weight of 8K and hence the former derivative formed a stable particle more easily. It was also found that a hyaluronic acid derivative having a larger PEG introduction ratio formed a more stable particle.

A particle shape was observed with a transmission electron microscope (TEM) JEM-1400 manufactured by JEOL Ltd. A sample was prepared by: mounting an aqueous solution (1 mg/ml) of the hyaluronic acid derivative 1 on a collodion membrane-attached mesh (200 mesh) manufactured by Nisshin EM Corporation; and air-drying the solution. The sample was observed under an acceleration voltage of 120 kV by a TEM mode. A particle diameter distribution was obtained by: observing 100 or more particle images per sample; and calculating an average particle diameter and a standard deviation based on their particle diameters. The average particle diameters±standard deviations of hyaluronic acid derivatives 1a, 1h, and 1n based on transmission electron microscope observation were 41±18 nm, 117±28 nm, and 26±10 nm, respectively.

Figure 5A:
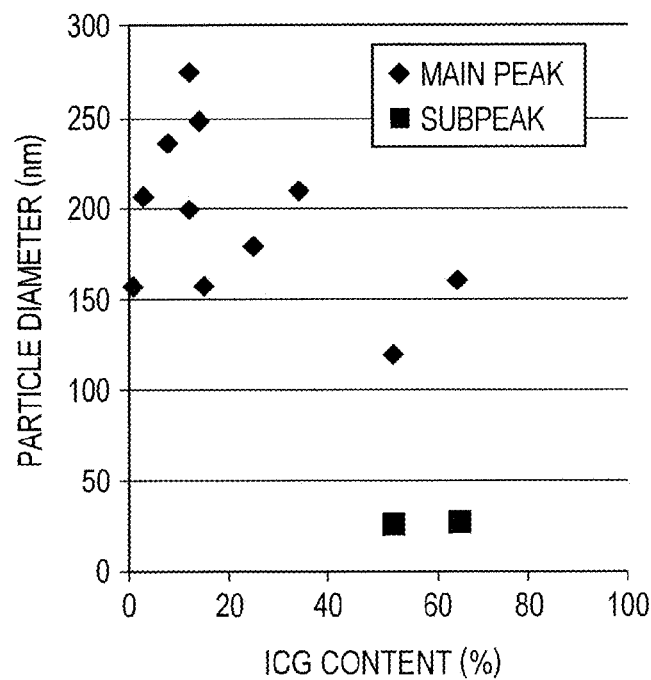
FIG. 5A is a graph showing a relationship between a particle diameter and an ICG content.

FIG. 5A shows a relationship between a particle diameter and an ICG content (data from Table 2). It was found from FIG. 5A that the particle diameter tended to reduce as the ICG content increased. This is probably caused by an improvement in association ability in water, or a variation in shape of an association such as a micelle or a vesicle, resulting from hydrophobicity enhanced by an increase in ICG content. It was found from the results that to increase the ICG content contributed not only to an improvement in sensitivity of a contrast agent but also to a reduction in particle size and, as described in Examples to be described later, was important for the exhibition of good dynamics in a body.

The hyaluronic acid derivative 1 stored in a solid state for a while after the freeze-drying shows an extreme reduction in water solubility. An aqueous solution of the derivative 1 is desirably prepared after the freeze-drying. A hyaluronic acid derivative having high water solubility can be obtained again by: dissolving the derivative 1 having a low water solubility in DMF; dialyzing a solution obtained by dispersing the DMF solution in the same volume of water against water; and freeze-drying the resultant.

As shown in Table 2, a similar reaction is performed with the derivative 3 having a molecular weight of 5K, whereby the corresponding product can be obtained. However, a reaction involving the derivative 3 having a molecular weight of 25K under the same conditions shows a low yield and low reproducibility, though the reaction proceeds well in some cases (the hyaluronic acid derivative 1n). In addition, a reaction involving the derivative 3 having a molecular weight of 50K hardly proceeded.

Figure 5B:
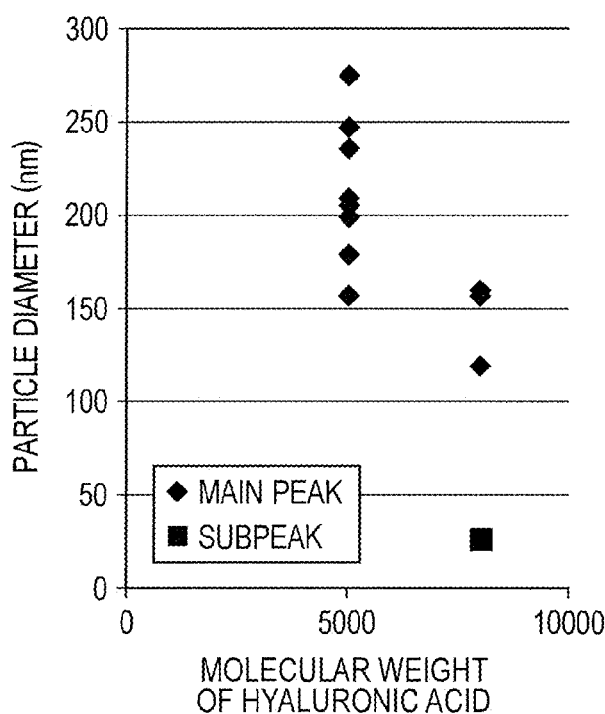
FIG. 5B is a graph showing a relationship between a particle diameter and the molecular weight of hyaluronic acid.

Table 3 summarizes the yield and reproducibility of a hyaluronic acid derivative based on the results of Comparative Example 1 and Example 1(5). As can be seen from Table 3, in order that a hyaluronic acid derivative having ICG and PEG may be efficiently synthesized by employing the synthetic method, the molecular weight of hyaluronic acid to be used is desirably about 5K to 25K, more desirably 5K to 8K. FIG. 5B shows a relationship between a particle diameter and the molecular weight of hyaluronic acid, and it was found from the figure that a molecular weight of 8K tended to result in a smaller particle diameter than a molecular weight of 5K did.

TABLE 2

| Hyaluronic acid derivative No. | MW (HA-Na) | a/b | Yield (%)[a] | p:q:r[b] | $D_{DLS}$ (nm)[c] | cac (×10$^{-4}$ g/L) |
|---|---|---|---|---|---|---|
| 1a | 8K | 0.25/1.75 | 60 | 15:85:0 | 157 ± 38 | 7.9 |
| 1b | 8K | 0.75/1.25 | 68 | 53:47:0 | 26 ± 6[d] 120 ± 59[d] | 8.4 |
| 1c | 8K | 1.00/1.00 | 81 | 66:34:0 | 27 ± 8[d] 160 ± 76[d] | 9.2 |
| 1d | 8K | 1.20/0.80 | 79 | 78:22:0 | | |
| 1e | 5K | 0.00/2.00 | 93 | 0:100:0 | — | |
| 1f | 5K | 0.05/1.95 | 84 | 1:99:0 | 157 ± 38 | 13 |
| 1g | 5K | 0.10/1.90 | 60 | 3:97:0 | 206 ± 61 | 2.2 |
| 1h | 5K | 0.25/1.75 | 68 | 12:88:0 | 275 ± 73 | 2.3 |
| 1i | 5K | 0.50/1.50 | 81 | 34:66:0 | 209 ± 56 | 3 |
| 1j | 5K | 0.20/0.20 | 70 | 14:26:60 | 248 ± 72 | 6.3 |
| 1k | 5K | 0.20/0.40 | 78 | 8:44:48 | 236 ± 84 | 4 |
| 1l | 5K | 0.20/0.80 | 76 | 12:77:11 | 199 ± 62 | 2.1 |
| 1m | 5K | 0.40/0.40 | 74 | 25:39:36 | 179 ± 46 | 5 |
| 1n | 25K | 0.20/0.80 | 32 | 11:89:0 | 29 ± 7 | 21 |

[a]Calculated from a molecular weight based on the introduction ratios of ICG and PEG moieties
[b]Calculated from the integrated value of $^1$H-NMR and an absorbance in UV-vis measurement
[c]A nanoparticle was prepared by dissolving a hyaluronic acid derivative in water. Its particle diameter was measured by dynamic light scattering.
[d]The two kinds of particles were substantially identical in scattering intensity to each other.
The symbol "—" shown in the table means that measurement could not be performed owing to a low scattering light intensity.

TABLE 3

Synthetic yield and reproducibility of hyaluronic acid derivative

| Hyaluronic acid (starting material) Molecular weight | Hyaluronic acid tetrabutylammonium salt | Hyaluronic acid derivative having azide group | | Comparative Example: Synthesis of hyaluronic acid derivative containing ICG (synthesized from hyaluronic acid derivative having azide group) | | Compound of the present invention Hyaluronic acid derivative containing ICG and PEG (synthesized from hyaluronic acid derivative having azide group) | |
|---|---|---|---|---|---|---|---|
| | Yield % | Yield % | Reproducibility | Yield % | Reproducibility | Yield % | Reproducibility |
| 2.5K | 83 | 85 | low | Unexamined | | Unexamined | |
| 5K | 99 | 66 | high | 78.5 | high | 72.4 | high |
| 8K | 85 | 70 | high | 51 | low | 69.7 | high |
| 25K | 62 | 99 | high | Unexamined | | 32 | low |
| 50K | 68 | 99 | high | Unexamined | | 0 (No reaction) | — |
| 110K | 64 | 99 | low | Unexamined | | Unexamined | |

Figure 6:
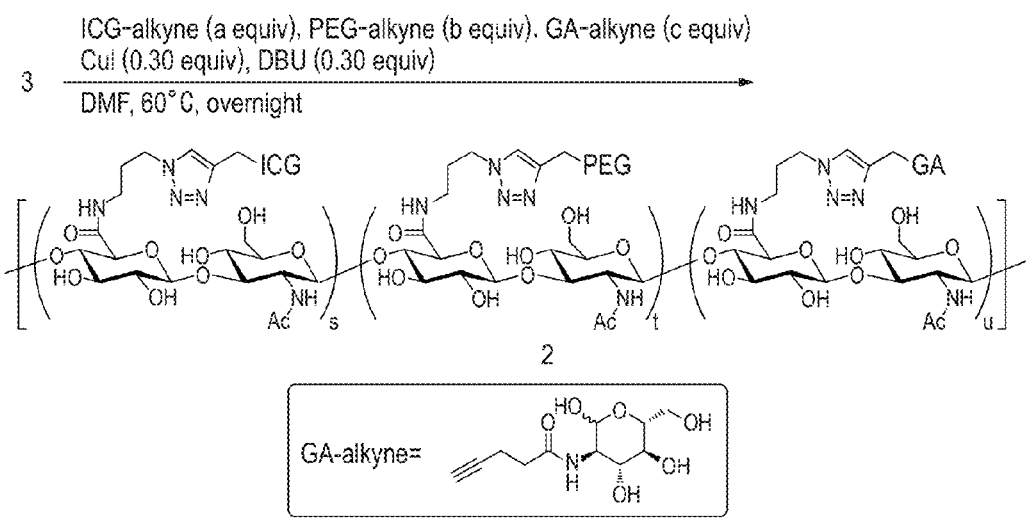
FIG. 6 illustrates a synthesis scheme for a hyaluronic acid derivative 2 having ICG, PEG, and GA.
Figure 14:
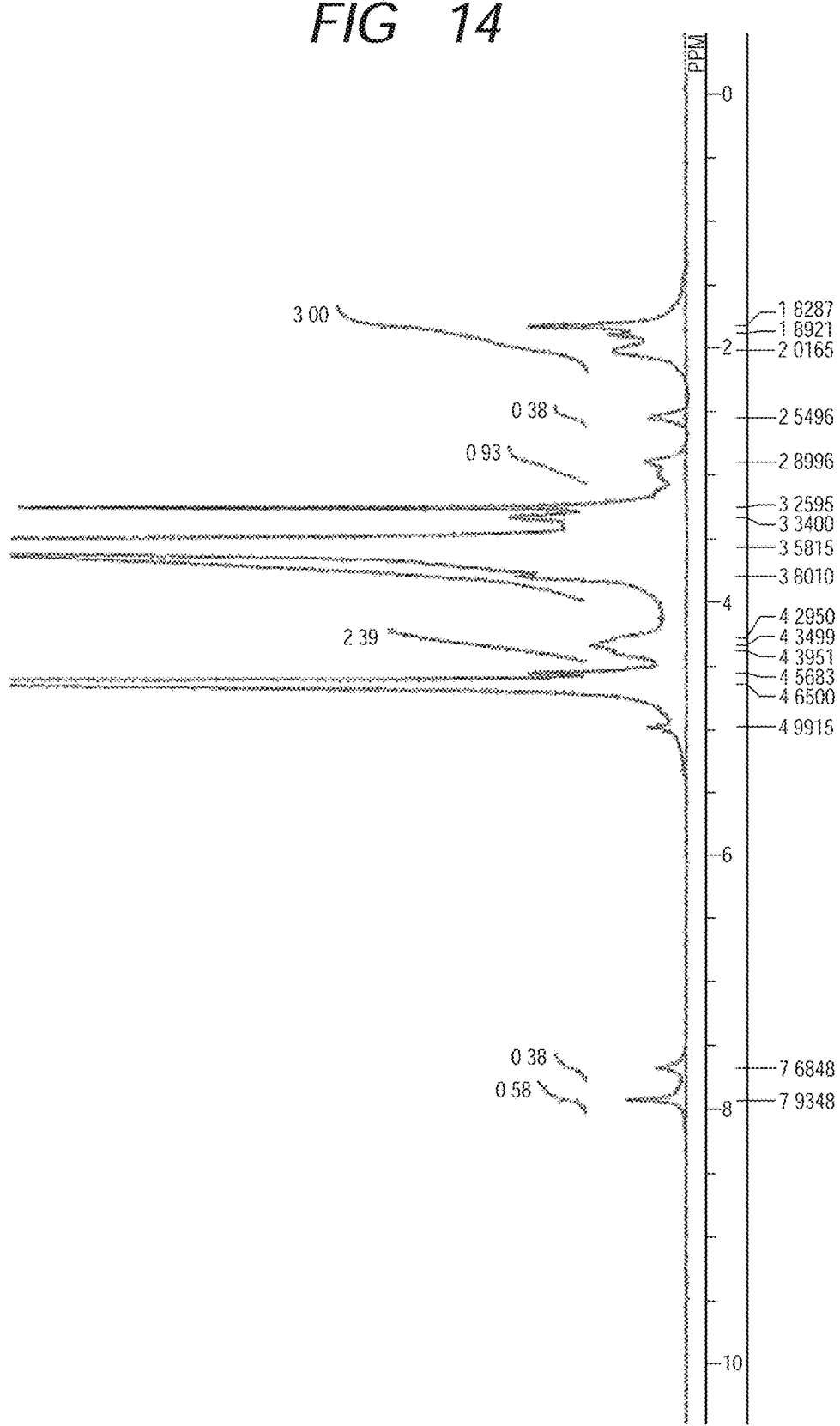
FIG. 14 shows the $^1$H-NMR chart of the derivative 2a(GA).

Example 1(6): Synthesis of Hyaluronic Acid Derivative 2 Containing ICG, PEG, and GA Various hyaluronic acid derivatives 2 each containing ICG, PEG, and GA can each be obtained by simultaneously conjugating ICG-alkyne, PEG-alkyne, and GA-alkyne (Non Patent Literature 8) to the hyaluronic acid derivative 3 having an azide group (FIG. 6 and Table 4). A typical synthetic example is described below. Under $N_2$ atmosphere, 23 mg of the derivative 3 (50 µmol in terms of minimum unit, azidation efficiency: >99%) were loaded into a 25-ml Schlenk flask and then dissolved in 2 ml of anhydrous DMF. After 14 mg (20 µmol) of ICG-alkyne, 40 mg (20 µmol) of PEG-alkyne, and 5.2 mg (20 µmol) of GA-alkyne had been added to the solution, 2.9 mg (15 µmol) of CuI and 2.3 mg (15 µmol) of DBU were added to the mixture, and then the whole was stirred at 60° C. overnight. 2 Milliliters of water were added to the solution and then the mixture was dialyzed with a dialysis membrane having a molecular weight cut-off of 25K for 24 hours against water. The resultant aqueous solution was filtered with a filter (pore diameter: 0.45 µm) and then freeze-dried to provide 72 mg (87%) of a hyaluronic acid derivative 2 having ICG, PEG, and GA as a deep green solid. Its identification was performed by $^1$H-NMR ($^1$H-NMR (300 MHz, $D_2O$, 25° C.) δ/ppm; 1.75-2.15 (m, 3H), 2.55 (br s, 0.38H), 2.80-3.10 (m, 0.93H), 3.10-4.00 (m, 102H), 4.25-4.50 (m, 2.4H), 7.68 (s, 0.38H), 7.93 (br s, 0.58H)). FIG. 14 shows the $^1$H-NMR chart of the derivative 2a(GA).

It should be noted that the conversion ratio of a cyclization reaction was calculated based on the reduction ratio of 2H (1.67 ppm) at the 2-position of 3-azido-1-propylamine by $^1$H-NMR. The chemical shift (7.68 ppm) of a proton of a triazole ring to which GA had been conjugated was observed to differ from the chemical shift (7.93 ppm) of a proton of a triazole ring having ICG or PEG. The introduction ratio of a GA moiety was calculated based on the ratio of an azide group transformed into a triazole ring having GA to the reacted azide groups and the conversion ratio of the azide groups by utilizing the foregoing. The introduction ratio of an ICG moiety was determined as follows: the UV spectrum of a DMF solution of a hyaluronic acid derivative having ICG, PEG, and GA was measured and then the ratio was determined based on an absorbance at its maximum absorption wavelength (around 790 nm) by using ICG-alkyne as a standard substance. The introduction ratio of a PEG moiety was calculated from the conversion ratio of azide groups and the introduction ratios of GA and ICG moieties. In addition, a yield was determined with a molecular weight calculated based on the introduction ratios of ICG, PEG, and GA moieties.

TABLE 4

| Derivative No. | MW (HA-Na) | a/b/c | Yield (%)[a] | p:q:r[b] | $D_{DLS}$ (nm)[c] | $D_{DLS}$ (nm)[d] | $D_{DLS}$ (nm)[e] | cac ($\times 10^{-4}$ g/L) |
|---|---|---|---|---|---|---|---|---|
| 2a(GA) | 8K | 0.40/0.40/0.40 | 87 | 15:47:38 | 35 ± 9 | 158 ± 38 | 190 ± 105 | 6.9 |
| 2b(GA2) | 8K | 0.50/0.70/0.20 | 65 | 13:79:8 | 24 ± 5[f] | 88 ± 21 | 122 ± 36 | 4.6 |
|  |  |  |  |  | 90 ± 19[f] |  |  |  |
| 2c(GA4) | 8K | 0.50/0.30/0.70 | 67 | 16:26:58 | — | 146 ± 38 | 132 ± 40 | 11 |
| 2e(GA5) | 8K | 0.80/0.60/0.60 | 59 | 41:32:27 | 155 ± 37 | 108 ± 37 | 313 ± 109 | 8.8 |
| 2d(GA3) | 5K | 0.60/0.80/0.30 | 52 | 28:52:20 | — | — | 155 ± 38 | 3.6 |
| 2f(GA6) | 5K | 0.80/0.60/0.30 | 79 | 45:42:13 | — | — | 193 ± 46 | 2.1 |
| 2g(GA7) | 5K | 1.00/0.60/0.40 | 66 | 58:23:19 | 122 ± 31 | 64 ± 23 | 162 ± 71 | 5.2 |

[a] Calculated from a molecular weight based on the introduction ratios of ICG, PEG, and GA moieties
[b] Calculated from the integrated value of $^1$H-NMR and an absorbance in UV-vis measurement
[c] A nanoparticle was prepared by dissolving a hyaluronic acid derivative in water. Its particle diameter was measured by dynamic light scattering.
[d] A nanoparticle was prepared by: dissolving a hyaluronic acid derivative in DMF; mixing the solution with the same amount of water; and removing DMF by dialysis. Its particle diameter was measured by dynamic light scattering.
[e] A nanoparticle was prepared by: dispersing, in water, a hyaluronic acid derivative dissolved in $CHCl_3$; and removing $CHCl_3$ by evaporation under reduced pressure. Its particle diameter was measured by dynamic light scattering after the resultant aqueous solution had been irradiated with an ultrasonic wave for 30 minutes.
[f] The two kinds of particles were substantially identical in scattering intensity to each other. The symbol "—" shown in the table means that measurement could not be performed owing to a low scattering light intensity.

It was found from Table 4 that many hyaluronic acid derivatives each having ICG, PEG, and GA formed smaller particles than a hyaluronic acid derivative having ICG and PEG did. The dissolution of a hyaluronic acid derivative 2a(GA) in water was able to provide a particle having a diameter of about 35 nm. Hereinafter, the sample is referred to as "2as(GAs)". The redispersion of the derivative 2a(GA), which had been sufficiently dispersed in DMF, in water resulted in the formation of a particle having a diameter of about 158 nm. Hereinafter, the particle having a diameter of 158 nm is referred to as "2a(GA)". The foregoing suggests that a particle diameter can be controlled by a method of forming a nanoparticle. In each of hyaluronic acid derivatives 2b(GA2) and 2g(GA7), a particle having a diameter of 100 nm or less was obtained by a particle-forming method involving using DMF. Although there existed such samples like hyaluronic acid derivatives 2d(GA3) and 2f(GA6) that no particle formation could be observed in a particle-forming method involving using water or DMF owing to a low scattering intensity, an approach involving dispersing a $CHCl_3$ solution of a hyaluronic acid derivative in water and then removing $CHCl_3$ by evaporation was applicable to any sample and particle formation was observed. In any case, however, a formed particle was limited to a particle having a particle diameter of 120 nm or more, which was relatively large. It was found from the foregoing results that a particle having a relatively small diameter was obtained by increasing an ICG introduction ratio or increasing a PEG introduction ratio when the ICG introduction ratio was as low as about 15%.

Figure 19A:
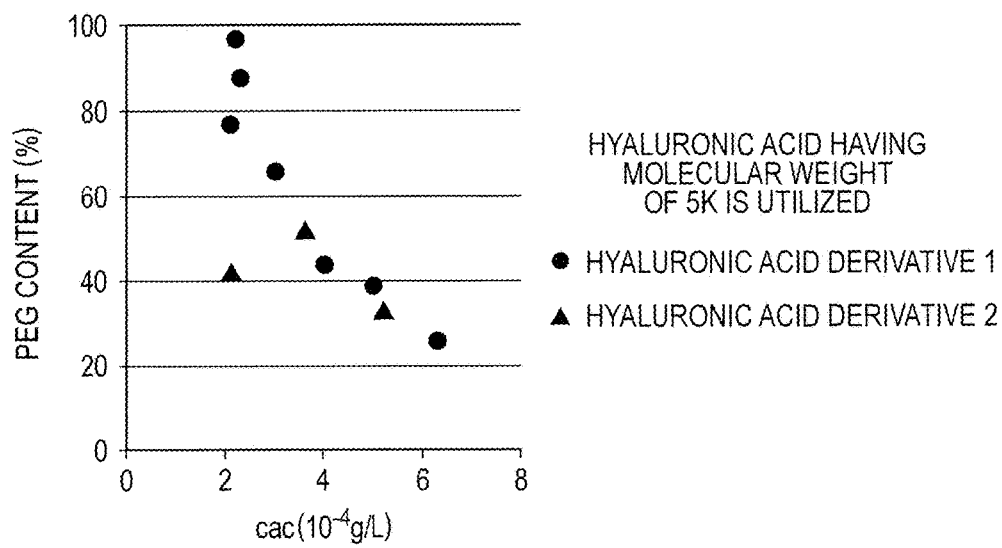
FIG. 19A shows a relationship between a cac and PEG content in each of the hyaluronic acid derivatives 1 and 2 synthesized by using hyaluronic acid having a molecular weight of 5K.
Figure 19B:
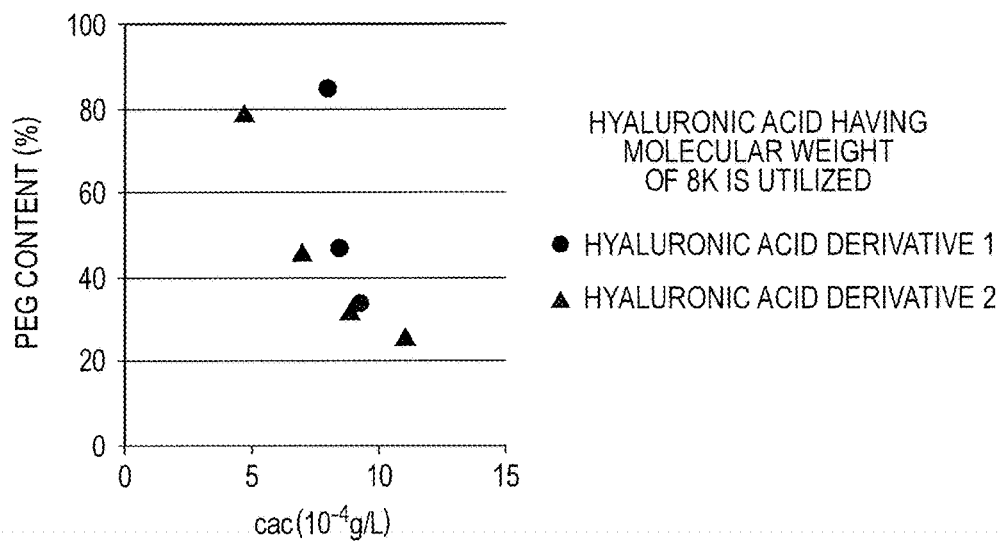
FIG. 19B shows a relationship between a cac and PEG content in each of the hyaluronic acid derivatives 1 and 2 synthesized by using hyaluronic acid having a molecular weight of 8K.

FIG. 19A and FIG. 19B show relationships between cac values and PEG contents in hyaluronic acid derivatives synthesized by using hyaluronic acids having molecular weights of 5K and 8K as starting materials (data from Table 2 and Table 4). It was found from each of the results that the cac tended to reduce as the PEG content increased.

Figure 20A:
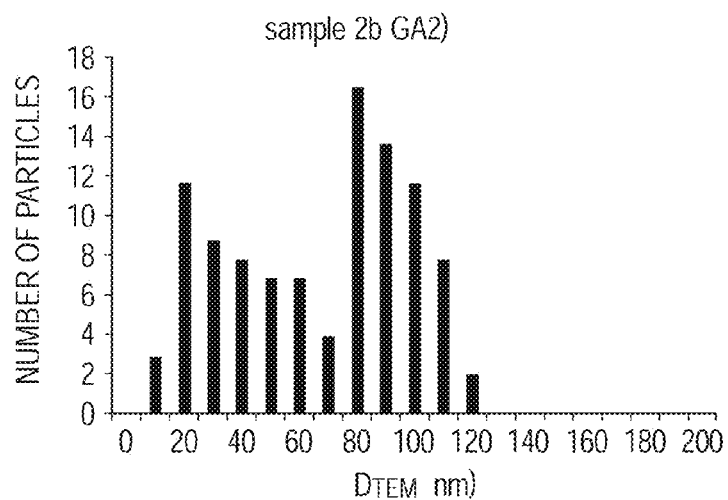
FIG. 20A shows the particle diameter distribution of the hyaluronic acid derivative 2b(GA2) based on TEM observation.
Figure 20B:
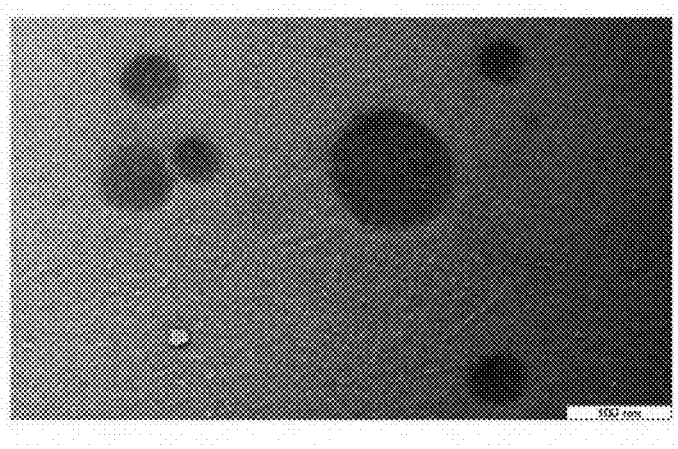
FIG. 20B shows a TEM observation image of the hyaluronic acid derivative 2b(GA2)
Figure 20C:
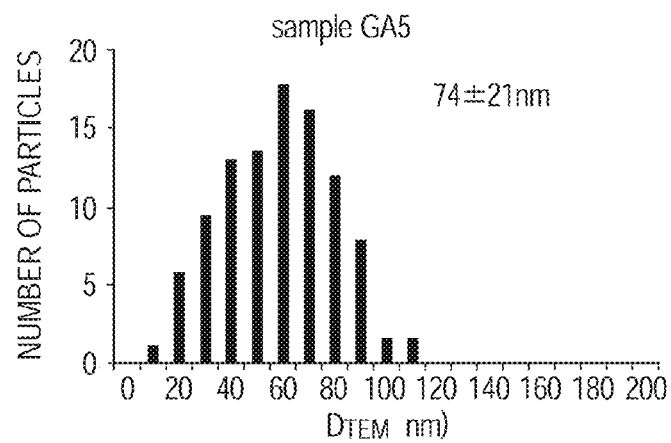
FIG. 20C shows the particle diameter distribution of a hyaluronic acid derivative 2e(GA5) based on TEM observation.

A particle shape was observed with a transmission electron microscope JEM-1400 manufactured by JEOL Ltd. A sample was prepared by: mounting an aqueous solution (1 mg/ml) of the hyaluronic acid derivative 2 on a collodion membrane-attached mesh (200 mesh) manufactured by Nisshin EM Corporation; and air-drying the solution. The sample was observed under an acceleration voltage of 120 kV by a TEM mode. A particle diameter distribution was obtained by: observing 100 or more particle images per sample; and calculating an average particle diameter and a standard deviation based on their particle diameters. As shown in FIG. 20A and FIG. 20B, two kinds of particle diameter distributions, i.e., large and small distributions, were obtained in the derivative 2b(GA2), which coincided with the results of DLS measurement involving using a sample prepared by dissolution in water. On the other hand, in any other sample, one kind of particle diameter distribution as typified by FIG. 20C was obtained. The average particle diameters±standard deviations of hyaluronic acid derivatives 2a(GA), 2b(GA2), 2c(GA4), 2d(GA3), 2e(GA5), 2f(GA6), and 2g(GA7) based on transmission electron microscope observation were 28±23 nm, 24±12 nm and 85±15 nm (bimodal), 75±22 nm, 64±19 nm, 74±21 nm, 35±8 nm, and 66±24 nm, respectively.

Comparative Example 2: Synthesis of Hyaluronic Acid Derivative 1 Having ICG and PEG in Water It has been reported that a cyclization reaction between hyaluronic acid having an azide group and a derivative having a terminal alkyne proceeds by utilizing a catalyst system in water in which copper sulfate and sodium ascorbate are combined (Non Patent Literature 9 and Non Patent Literature 10). In view of the foregoing, an attempt was made to cause ICG-alkyne and PEG-alkyne to react with the hyaluronic acid derivative 3 having an azide group under a catalyst condition in which copper sulfate and sodium ascorbate were combined.

An experimental example concerning the introduction of PEG is described below. After PEG-alkyne (3 equiv) had been added to an aqueous solution (5 ml) of the derivative 3 (MW(HA-Na)=8K, azidation efficiency: 100%), a DMF solution (5 ml) of sodium ascorbate (20 mol %) and copper sulfate pentahydrate (40 mol %) was added to the mixture, and then the whole was stirred at 27° C. overnight. The solution was dialyzed with a dialysis membrane having a molecular weight cut-off of 3.5K for 24 hours against water. The resultant was freeze-dried and purified by resedimentation with hexane/CHCl$_3$ (7:10) to provide a hyaluronic acid derivative having PEG (58%) as a pale brown solid. As described above, PEG was able to be introduced.

On the other hand, ICG-alkyne underwent no reaction. An experimental example is described below. PEG-alkyne (1.5 equiv), ICG-alkyne (1.5 equiv), and a DMF solution (3 ml) of sodium ascorbate (20 mol %) and copper sulfate pentahydrate (40 mol %) were added to an aqueous solution (3 ml) of the derivative 3 (MW(HA-Na)=8K, azidation efficiency: 100%), and then the mixture was stirred at 27° C. overnight. The solution was dialyzed with a dialysis membrane having a molecular weight cut-off of 3.5K for 24 hours against water. The resultant aqueous solution was filtered with a filter (pore diameter: 0.45 µm) and then freeze-dried to provide a hyaluronic acid derivative as a pale brown solid. Although PEG was introduced to 83% of the azide groups in the hyaluronic acid derivative 3, the remaining 17% remained unreacted and ICG was not introduced.

In conclusion, in the synthesis of the hyaluronic acid derivative 1 having ICG and PEG in water, the introduction of PEG was observed but no ICG was introduced. This is probably caused by the low water solubility of ICG-alkyne. In other words, it is difficult to synthesize the hyaluronic acid derivative having ICG and PEG of the present invention by a conventionally known underwater synthetic method, and a novel synthetic method involving using CuI/DMF according to the present invention has not been reported heretofore and its effectiveness has been shown. As described above, the synthetic method involving using CuI/DMF enables not only the introduction of an ICG derivative to hyaluronic acid but also simultaneous, efficient, quantitative introduction of the ICG derivative and PEG thereto.

Example 2: Evaluation for Retentivity in Blood

Figure 7:
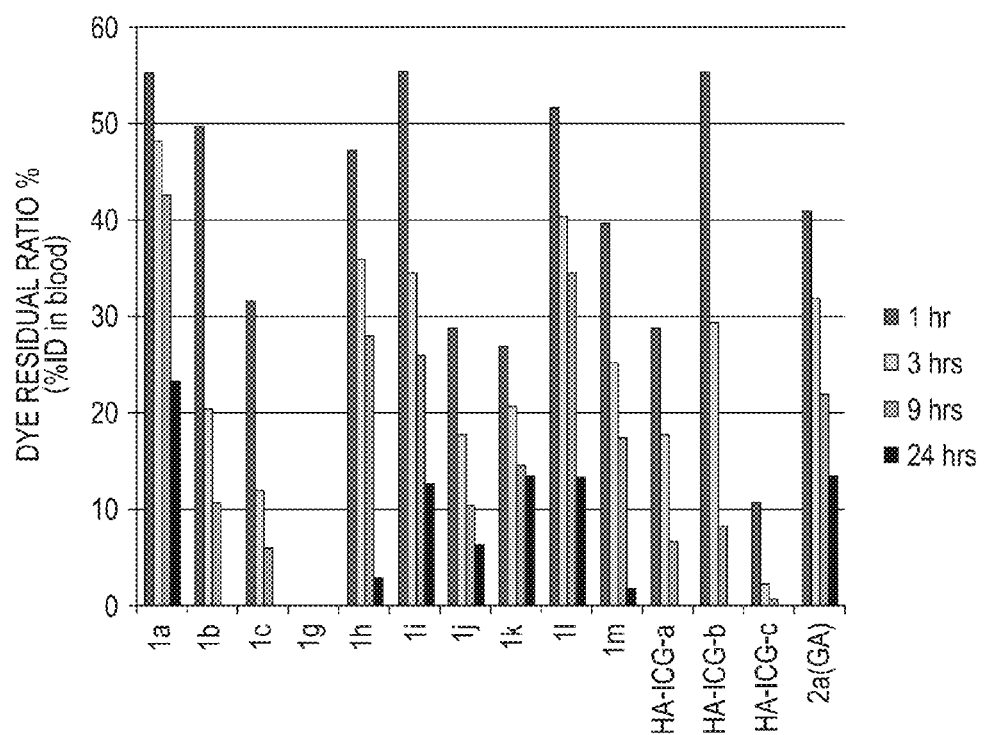
FIG. 7 is a graph showing the residual ratio of a dye with respect to its injected dose to a mouse.

In order for each of the compounds prepared in the foregoing to be evaluated for its retentivity in blood, each of the compounds was administered to the tail vein of a female outbred BALB/c Slc-nu/nu mouse (7- to 9-week old, Japan SLC, Inc.) and then a dye residual ratio in blood at each time was measured. Blood was collected from the tail vein of the mouse 1, 3, 9, and 24 hours after the administration, and then the blood, 1% Triton, and DMF were mixed at 2:9:9 in a 96-well plastic plate. The dye residual ratio in blood was measured by measuring the fluorescence intensity of the blood solution in the 96-well plastic plate with an IVIS (trademark) Imaging System 200 Series (manufactured by XENOGEN). FIG. 7 shows a dye residual ratio (% injected dose: abbreviated as "% ID") with respect to an injected dose at each time. The derivative 1g could not be evaluated because a sufficient fluorescence intensity could not be obtained. It was revealed from the measurement of the dye residual ratio that the derivatives 1a, 1h to 1m, and 2a(GA) were each excellent in retentivity in blood because the sample remained in the blood even after a lapse of 24 hours. On the other hand, the hyaluronic acid derivatives HA-ICG-a, HA-ICG-b, and HA-ICG-c (comparative example samples) each of which was free of PEG and had only ICG were each found to have low retentivity in blood because none of the samples remained in the blood after a lapse of 24 hours. The results have shown that in a hyaluronic acid derivative having ICG, the incorporation of PEG is essential for an increase in ICG content and an improvement in retentivity in blood, and the retentivity in blood can be controlled by the PEG content.

Figure 8A:
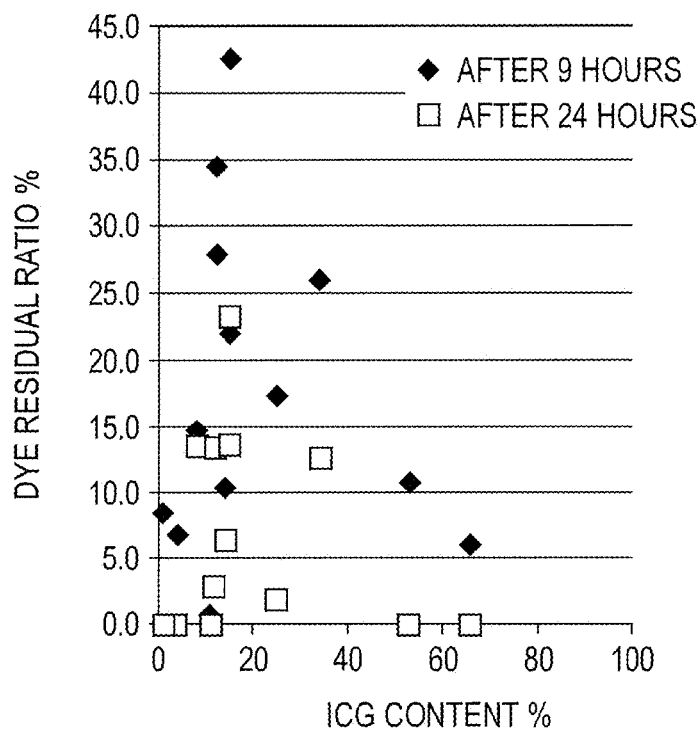
FIG. 8A is a graph showing relationships between the dye residual ratios in blood and the ICG contents of each sample 9 hours and 24 hours after administration.

FIG. 8A shows relationships between the dye residual ratios in blood and the ICG contents of each sample 9 hours and 24 hours after administration. It was found that the residual ratio in blood increased in the ICG content range of 10 to 40%.

Figure 8B:
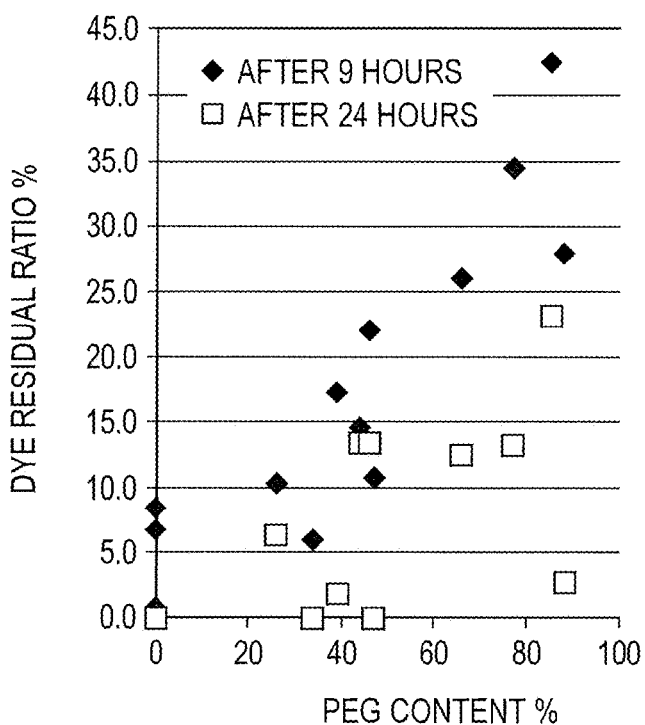
FIG. 8B is a graph showing relationships between the dye residual ratios in blood and the PEG contents of each sample 9 hours and 24 hours after administration.

FIG. 8B shows relationships between the dye residual ratios in blood and the PEG contents of each sample 9 hours and 24 hours after administration. It was found that the residual ratio in blood increased as the PEG content increased.

Example 3: Evaluation for Tumor-Contrasting Ability by Fluorescence Imaging

Figure 9:
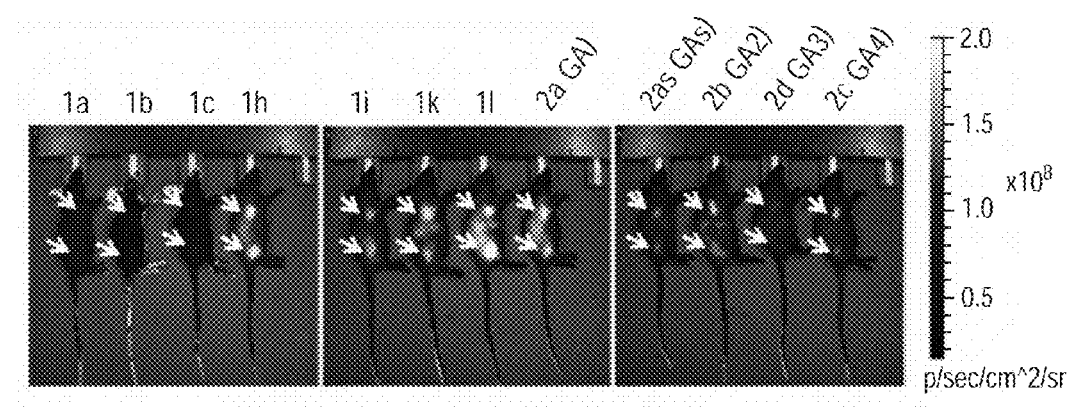
FIG. 9 shows fluorescence images of mice 24 hours after the administration of hyaluronic acid derivatives 1a, 1b, 1c, 1h, 1i, 1k, 1l, 2a(GA), 2as(GAs), 2b(GA2), 2d(GA3), and 2c(GA4).

The compounds obtained in Example 1 described above were evaluated for their tumor-contrasting abilities. The fluorescence imaging of a cancer-bearing mouse to which a hyaluronic acid derivative had been administered was performed for an evaluation for a tumor-contrasting ability. In the fluorescence imaging experiment, female outbred BALB/c Slc-nu/nu mice (6-week old at the time of purchase) (Japan SLC, Inc.) were used. For 1 week before the causing of the mice to bear cancers, the mice were habituated with a normal diet and bed in the animal facility of Kyoto University, Faculty of Medicine (Kyoto Prefecture, Japan) under such an environment that the diet and drinking water were available ad libitum. About 1 week before the imaging experiment, $1 \times 10^6$ colon 26 mouse colon cancer cells (RIKEN) were subcutaneously injected into the shoulders and femurs of the mice. The injected dose was 0.25 nmol per mouse in terms of a dye amount and the dye was injected as 100 µL of a PBS solution into the tail vein of each mouse. With regard to the whole-body fluorescence images of the mice to which the hyaluronic acid derivatives 1a, 1b, 1c, 1h, 1i, 1k, 1l, 2a(GA), 2as(GAs), 2b(GA2), 2d(GA3), and 2c(GA4) had been administered, the bright-field images and fluorescence images of the mice were acquired with an IVIS (trademark) Imaging System 200 Series (XENOGEN) 24 hours after the administration. FIG. 9 shows the fluorescence images of the mice 24 hours after the administration. Fluorescence signals at tumor sites indicated by white arrows in FIG. 9 were observed. The results showed that the hyaluronic acid derivative of the present invention was able to contrast a tumor and showed its effectiveness as a contrast agent for the optical imaging of a tumor.

Figure 10A:
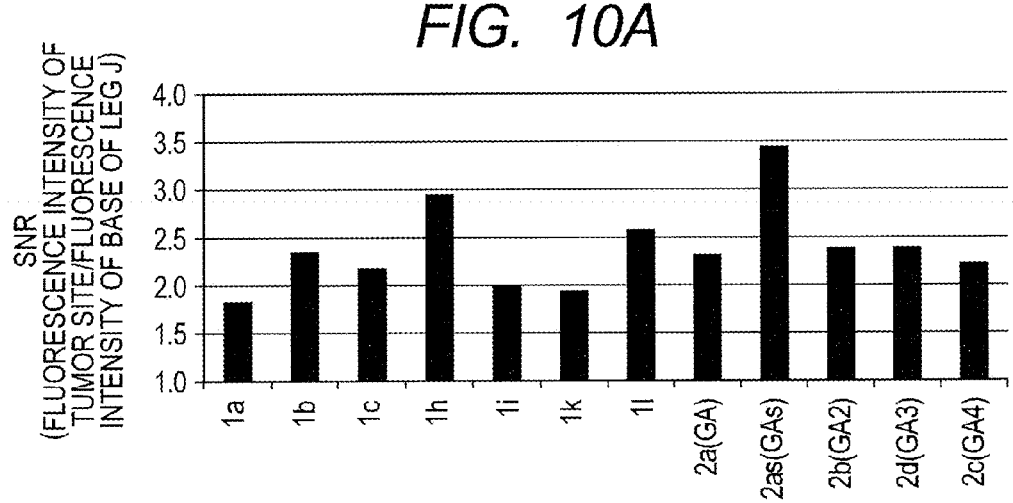
FIG. 10A is a graph showing the SNR of a mouse tumor image 24 hours after administration and FIG. 10B is a graph showing tumor accumulation property.

In FIG. 10A, a ratio between the fluorescence intensity of a tumor site (measured area: 0.5×0.5 cm) and the fluorescence intensity of the base of a leg (selected as a normal site, measured area: 0.5×0.5 cm) is drawn from the fluorescence imaging data shown in FIG. 9, and is then converted into a numerical value as a signal-to-noise ratio (SNR). That is, the SNR is a parameter showing the tumor-visualizing power of each compound and the compound becomes more effective as a contrast agent for the optical imaging of a tumor as the SNR increases. It was found from FIG. 10A that the SNR's of all compounds were 1.5 or more and the derivative 2a(GAs) having a small particle size had the highest SNR.

Example 4: Evaluation for Tumor Accumulation Property

Figure 10B:
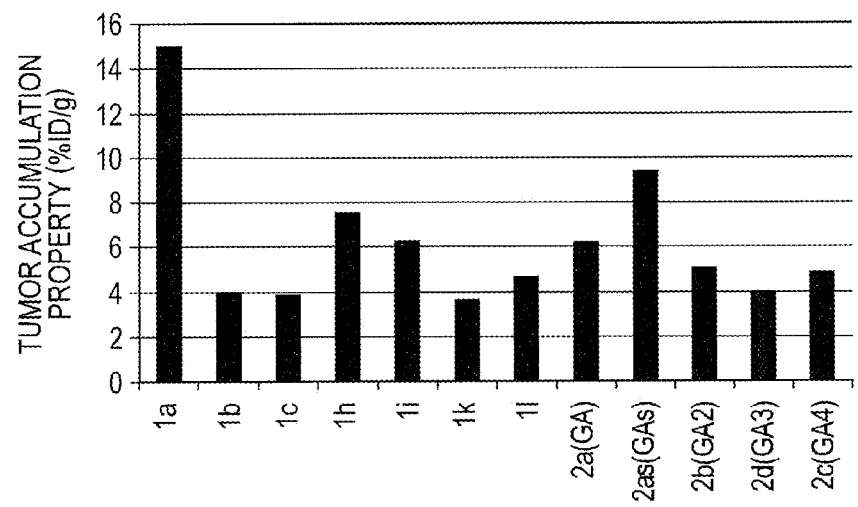
Figure 11:
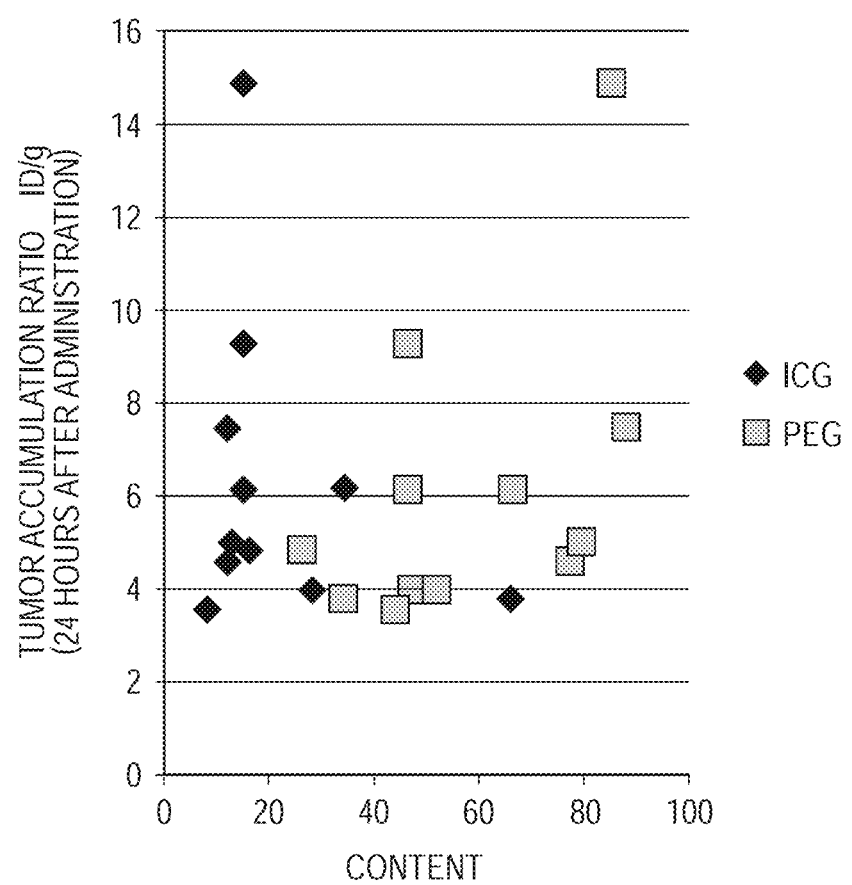
FIG. 11 is a graph showing a relationship among tumor accumulation property, and the ICG content and PEG content of each sample.

The hyaluronic acid derivatives 1a, 1b, 1c, 1h, 1i, 1k, 1l, 2a(GA), 2as(GAs), 2b(GA2), 2d(GA3), and 2c(GA4) were evaluated for their tumor accumulation properties by determining the amount of a dye in the tumor of a mouse of the tumor-contrasting experiment performed in Example 3. The tumor accumulation property was represented as a transfer ratio (% ID/g) to the tumor with respect to the total injected dose per 1 g of the tumor. First, the mouse was euthanized with a carbon dioxide gas 24 hours after the administration, followed by the surgical resection of the tumor. The tumor was transferred to a plastic tube and then a 1% Triton-X100 aqueous solution was added in an amount 1.25 times as large as the weight of the tumor thereto, followed by crushing with a plastic pestle. Next, dimethylformamide (DMF) was added in an amount 20.25 times as large as the weight of the tumor tissue thereto. The amount of the dye in the tumor was determined by measuring the fluorescence intensity of the tumor-crushed solution, which was in a state of being stored in the plastic tube, with an IVIS (trademark) Imaging System 200 Series (XENOGEN). FIG. 10B shows the result. The dye was detected in the tumor to which the hyaluronic acid derivative according to the present invention had been administered, and hence accumulation in the tumor was confirmed. The tumor accumulation properties ranged from 4% to 14% and the derivative 1a showed the highest tumor accumulation property, i.e., 14.8% ID/g. FIG. 11 shows a relationship among tumor accumulation property, and the ICG content and PEG content of each sample. The following tendency was observed: the tumor accumulation property improved as the PEG content increased. Meanwhile, the following tendency was observed: the tumor accumulation property improved at an ICG content of about 15%. No reduction in tumor accumulation property was observed even when the ICG content was set to 20% or more. The result showed that the derivative was a compound capable of maintaining accumulation property in a tumor while having a high ICG content, in other words, enhancing sensitivity.

Example 5: Measurement of Photoacoustic Signal

Figure 16A:
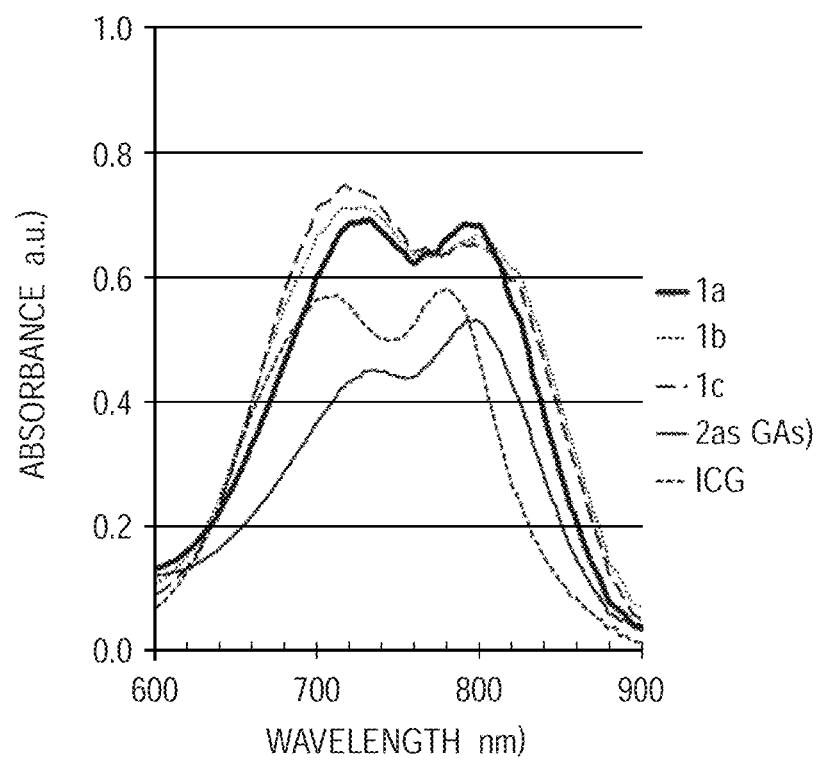
FIG. 16A shows the absorption spectra of the derivatives 1a, 1b, 1c, and 2as(GAs), and ICG for comparison.
Figure 16B:
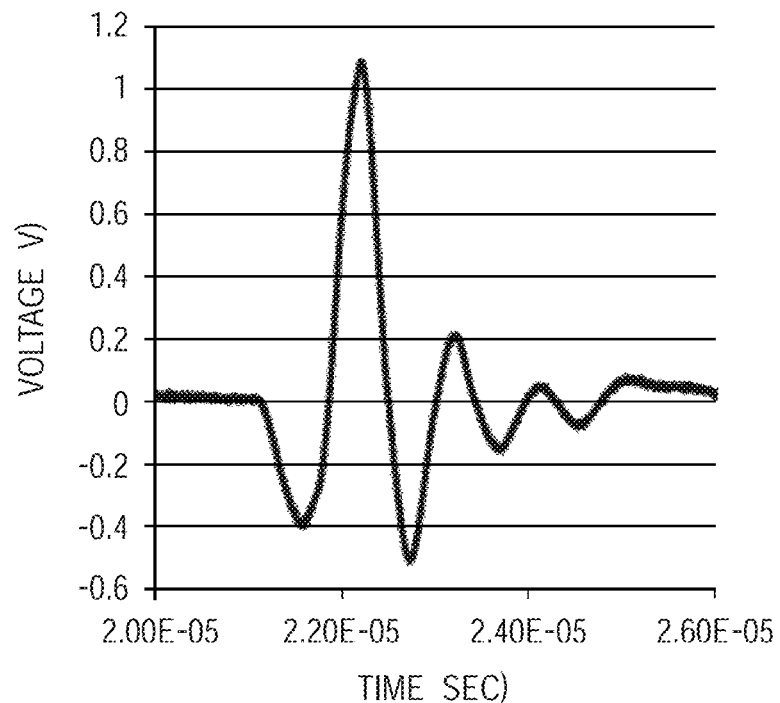
FIG. 16B shows the time change spectrum of the photoacoustic signal (voltage) of the derivative 1a at a laser wavelength of 790 nm.
Figure 17:
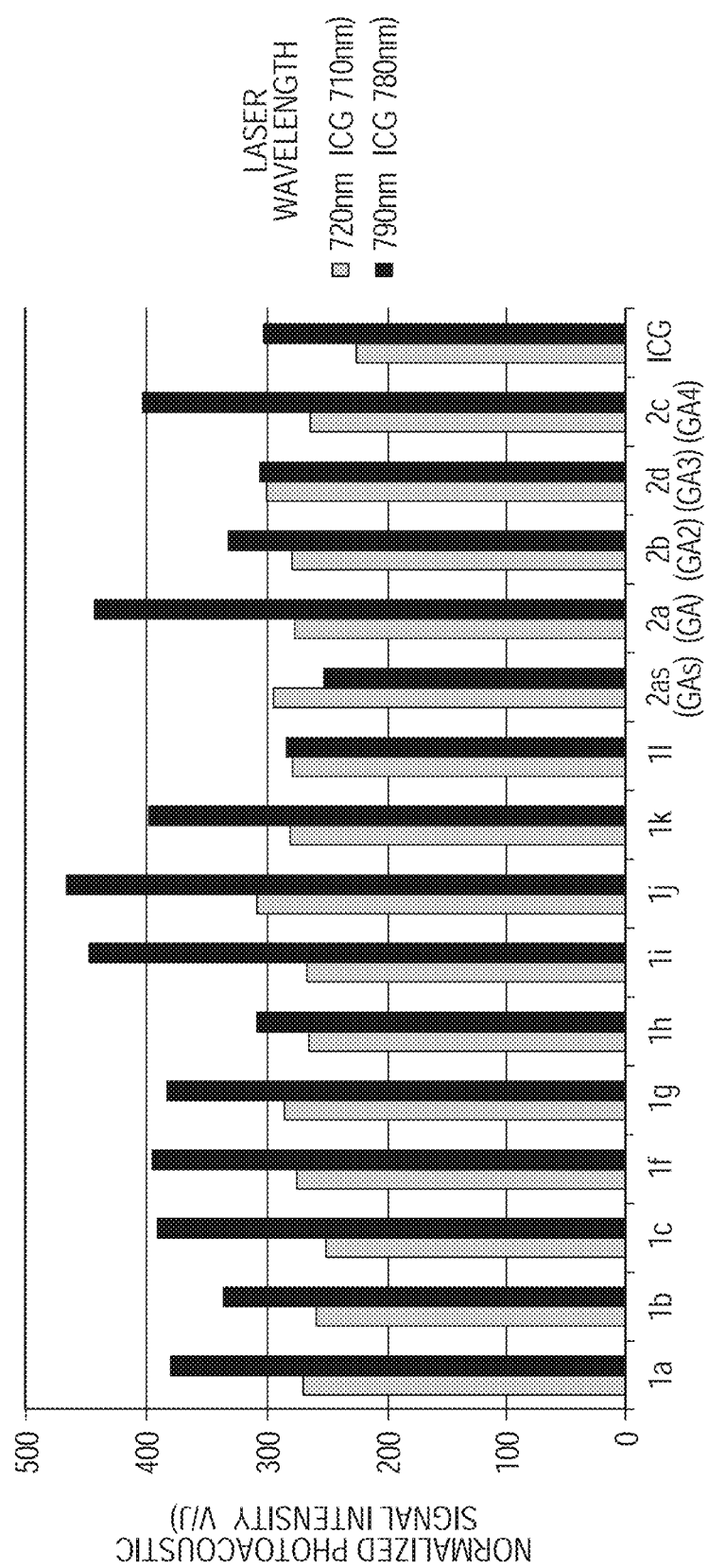
FIG. 17 is a graph showing the intensities of the photoacoustic signals of a compound of the present invention and ICG for comparison normalized by their absorbances.

The photoacoustic signals of the compounds obtained in Example 1 described above were measured. As a comparative example, an aqueous solution of ICG was similarly subjected to the measurement. The measurement of a photoacoustic signal was performed by: irradiating an aqueous solution of a sample with pulse laser light; detecting the photoacoustic signal from the sample with a piezoelectric element; amplifying the signal with a high-speed preamplifier; and acquiring the amplified signal with a digital oscilloscope. Specific conditions for the measurement are as described below. Titanium sapphire laser (manufactured by Lotis Ltd.) was used as a light source. Laser wavelengths were set to 720 nm and 790 nm, and the wavelengths were set to 710 nm and 780 nm for the aqueous solution of ICG for comparison. This is because of the following reason: the aqueous solution of the sample has two absorption bands, and for example, in each of the compounds obtained in Example 1 described above, absorption peaks are observed at 720 nm and 790 nm. FIG. 16A shows the absorption spectra of the typical samples 1a, 1b, 1c, and 2as(GAs), and ICG for comparison. The conditions of an energy density of 12 mJ/cm$^2$, a pulse width of 20 nanoseconds, and a pulse repetition of 10 Hz were adopted. A Model V303 (manufactured by Panametrics-NDT) was used as an ultrasonic transducer. The conditions of a central band of 1 MHz, an element size of ϕ0.5, a measurement distance of 25 mm (non-focus), and an amplification of +30 dB (Ultrasonic Preamplifier Model 5682 manufactured by Olympus Corporation) were adopted. A measurement vessel was a cuvette made of polystyrene, and had an optical path length of 0.1 cm and a sample volume of about 200 µl. Water was used as a solvent. A DPO4104 (manufactured by TEKTRONIX, INC.) was used as a measuring device, and measurement was performed under the conditions of: trigger: detection of photoacoustic light with a photodiode; and data acquisition: 128 times (128 pulses) on average. FIG. 16B shows the time change spectrum of the photoacoustic signal (voltage) of the typical sample 1a at a laser wavelength of 790 nm. In addition, FIG. 17 shows the intensities of the photoacoustic signals of the compound of the present invention and ICG for comparison normalized by their absorbances. The phrase "normalized by their absorbances" as used herein means that an actually obtained voltage value (V) is divided by the intensity (J) of applied laser and the absorbance of the sample at the wavelength of the laser. As is apparent from FIG. 17, all compounds of the present invention were able to emit photoacoustic signals and were able to provide photoacoustic signal intensities comparable to or higher than that of ICG for comparison. A possible reason why the photoacoustic signal intensities become higher than that of ICG is that the compound of the present invention obtained in Example 1 described above uses a hydrophobic ICG derivative and the thermal conversion efficiency of the dye itself is higher than that of ICG. Another possible reason is that the molecules of the dye strongly aggregate by virtue of its hydrophobicity or a heat-trapping effect resulting from the fact that the dye is shielded with hyaluronic acid from water as a medium may have some contribution. The results of this example have confirmed that the compound of the present invention functions as a photoacoustic contrast agent.

FIG. 18 shows the apparent molecular weight of a hyaluronic acid unit, the number of ICG derivatives conjugated to hyaluronic acid, the molecular weight of the entire polymer, and the absorption coefficient of a hyaluronic acid derivative at 790 nm for the compound of the present invention. In the present invention, a large number of ICG derivatives were able to be conjugated to hyaluronic acid and hence a high light-absorbing ability was able to be imparted to hyaluronic acid. As a result, a compound capable of emitting a strong photoacoustic signal was successfully obtained. Further, the hyaluronic acid derivative of the present invention can form a nanoparticle and hence its absorption coefficient as the nanoparticle becomes significantly high. That is, the nanoparticle may contain at least 10 to 1,000 hyaluronic acid derivative molecules and hence the nanoparticle has an absorption coefficient 10 to 1,000 times as high as that of a hyaluronic acid derivative molecule. Specifically, the particle may have an absorption coefficient of the order of $10^6$ to $10^8$ (when the coefficient is calculated on the assumption that the volume of the hyaluronic acid derivative molecule is about 11,000 $nm^3$).

As is apparent from this example, the inventors were the first to find that the ICG content of a hyaluronic acid derivative could be increased by simultaneously conjugating an ICG derivative and PEG to hyaluronic acid, and have succeeded in creating a hyaluronic acid derivative having a high ICG content. Although the ICG content of hyaluronic acid containing a hydrophilic ICG derivative disclosed in Non Patent Literature 1 is as low as about 12%, the ICG content of the hyaluronic acid derivative of the present invention can be made higher than 13%. Meanwhile, the maximum of the content was 78%. Therefore, the ICG content of the hyaluronic acid derivative of the present invention preferably ranges from more than 13% to 78% or less.

Figure 21A:
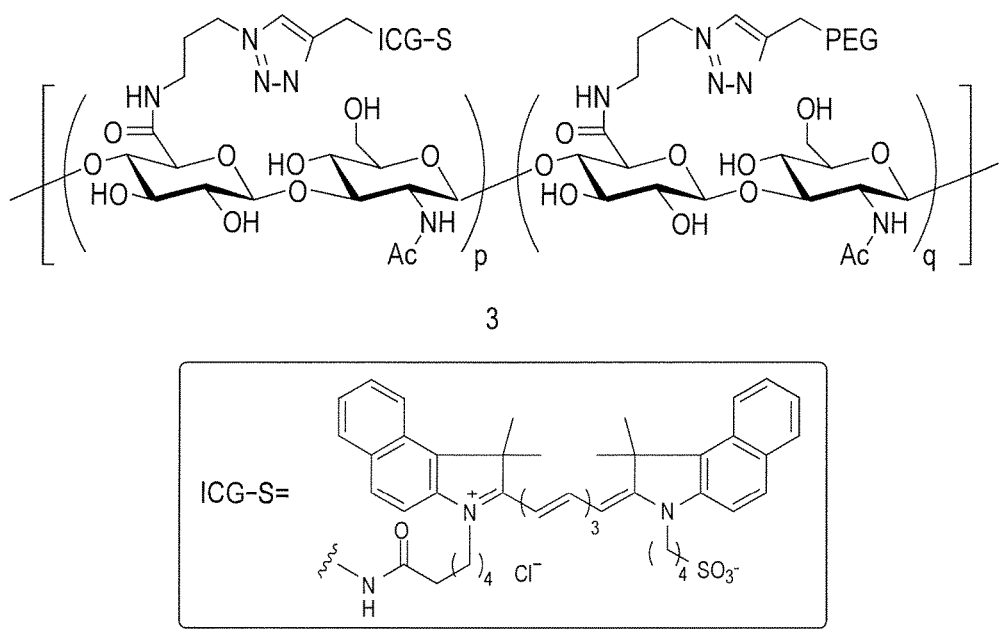
FIG. 21A illustrates a structural formula for a hyaluronic acid derivative 4 containing a near-infrared dye having a sulfonyl group.

Example 6: Synthesis of Near-Infrared Dye-Containing Hyaluronic Acid Derivative 4 Having Sulfonyl Group A near-infrared dye-containing hyaluronic acid derivative 4 having a sulfonyl group was synthesized according to the same scheme as that of Example 1 except that a near-infrared dye ICG-S-alkyne having a sulfonyl group was used. FIG. 21A illustrates a structural formula for the derivative. An HA-Na having a molecular weight of 5K was used as a starting material.

Example 6(1): Synthesis of Near-Infrared Dye ICG-S-Alkyne

Figure 21B:
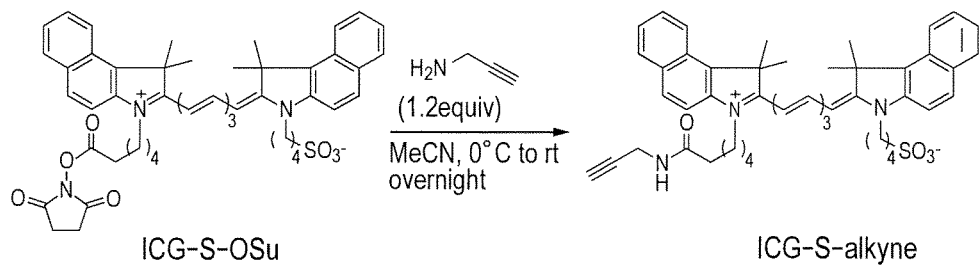
FIG. 21B illustrates a synthesis scheme for a near-infrared dye ICG-S-alkyne.
Figure 21C:
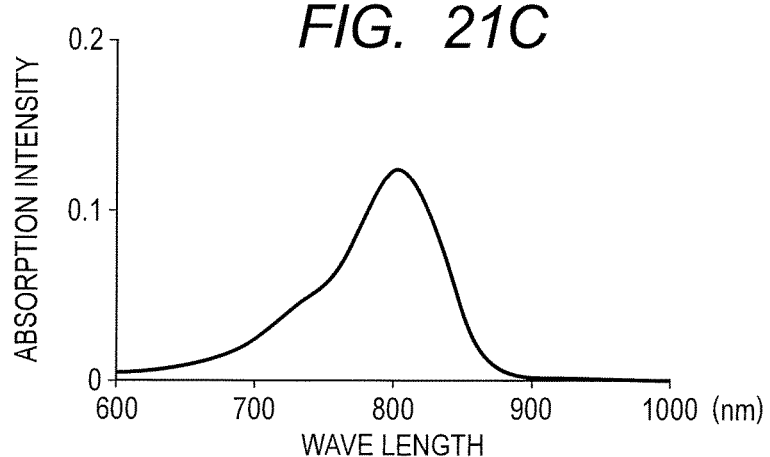
FIG. 21C shows the UV-visible-near-infrared absorption spectrum of ICG-S-alkyne.

FIG. 21B illustrates the synthesis of the near-infrared dye ICG-S-alkyne. First, 0.62 g (0.75 mmol) of an indocyanine green derivative ICG-S-OSu disclosed in Japanese Patent Application Laid-Open No. 1997-124599 was loaded into a 50-ml one-necked round-bottom flask and then dissolved in 2 ml of acetonitrile. Propargylamine (58 µL, 0.90 mmol) was added to the solution at 0° C. and then the mixture was stirred for 2 hours. 10 Milliliters of 0.1 N hydrochloric acid were added to the solution and then the aqueous layer was extracted with $CH_2Cl_2$. The organic layer was washed with a saturated saline solution and then dried with magnesium sulfate. The solvent was removed by evaporation under reduced pressure and then the resultant dark green solid was purified by centrifugal sedimentation ($CH_2Cl_2/Et_2O$). The dark green solid was washed with a small amount of ethyl acetate and then dried under reduced pressure. After that, 0.63 g (93%) of ICG-S-alkyne was obtained as a dark green solid. The results were as follows: $^1$H-NMR (400 MHz, $CD_3OD$, 25° C., TMS) δ/ppm; 1.51 (t, J=6.4 Hz, 2H), 1.71 (t, J=7.3 Hz, 2H), 1.86 (t, J=6.4 Hz, 2H), 1.91-2.15 (m, 2H), 2.00 (s, 12H), 2.22 (t, J=7.2 Hz, 2H), 2.67 (s, 1H), 2.91 (t, J=6.0 Hz, 2H), 3.40-3.57 (m, 2H), 3.90 (d, J=2.3 Hz, 2H), 4.10-4.32 (m, 4H), 6.21-6.36 (m, 1H), 6.36-6.49 (m, 1H), 6.53-6.76 (m, 2H), 7.39-7.51 (m, 2H), 7.54 (d, J=8.7 Hz, 1H), 7.57-7.78 (m, 3H), 7.88-8.13 (m, 6H), 8.13-8.38 (m, 2H); FAB-HRMS m/e 767.3757 $[M]^+$. The light absorption spectrum of ICG-S-alkyne in a near-infrared region is as shown in FIG. 21C (in chloroform, dye concentration: $1.0\times10^{-6}$ M). The compound has an absorption maximum at 804 nm. The compound had a molar absorption coefficient at the maximum absorption wavelength of $1.2\times10^5$ ($M^{-1}\times cm^{-1}$).

Figure 22:
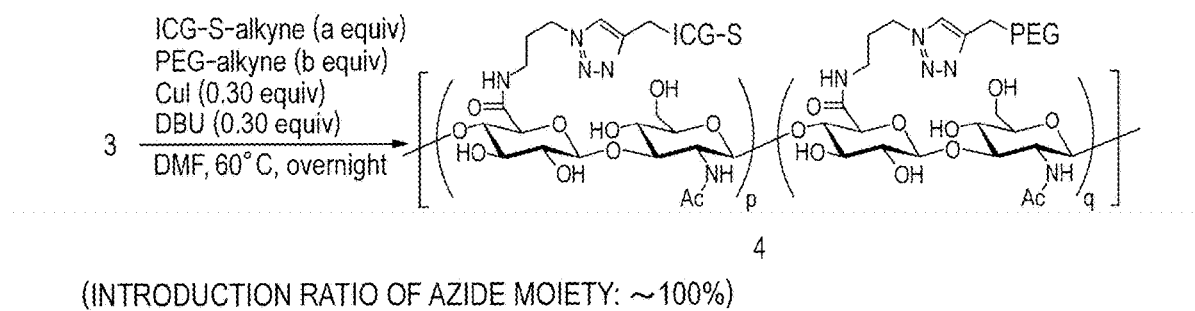
FIG. 22 illustrates a synthesis scheme for the hyaluronic acid derivative 4 having ICG-S and PEG.

Example 6(2): Synthesis of Hyaluronic Acid Derivative 4 Having ICG-S and PEG The various hyaluronic acid derivatives 4 each having ICG-S and PEG can each be obtained by simultaneously conjugating ICG-S-alkyne and PEG-alkyne to the hyaluronic acid derivative 3 having an azide group (FIG. 22 and Table 5). A typical synthetic example is described below. Under $N_2$ atmosphere, 23 mg of the derivative 3 (MW(HA-Na)=5K, 50 µmol in terms of minimum unit, azidation efficiency: >99%) were loaded into a 25-ml Schlenk flask and then dissolved in 2 ml of anhydrous DMF. After 38 mg (50 µmol) of ICG-S-alkyne and 0.10 g (50 µmol) of PEG-alkyne had been added to the solution, 2.9 mg (15 µmol) of CuI and 2.3 mg (15 µmol) of DBU were added to the mixture, and then the whole was stirred at 60° C. overnight. 2 Milliliters of water were added to the solution and then the mixture was dialyzed with a dialysis membrane having a molecular weight cut-off of 25K for 24 hours against water. The resultant aqueous solution was filtered with a filter (pore diameter: 0.45 µm) and then freeze-dried to provide 83 mg (79%) of a hyaluronic acid derivative 4b having ICG-S and PEG as a deep green solid. Its identification was performed by $^1$H-NMR ($^1$H-NMR (400 MHz, $D_2O$, 25° C.) δ/ppm; 1.80-2.16 (m, 3H), 3.10-4.01 (m, 633H), 4.25-4.60 (m, 1H), 7.93 (br s, 0.98H)).

It should be noted that the conversion ratio of a cyclization reaction was calculated based on the reduction ratio of 2H (1.67 ppm) at the 2-position of 3-azido-1-propylamine by $^1$H-NMR. The introduction ratio of an ICG moiety was determined as follows: the UV spectrum of a DMF solution of a hyaluronic acid derivative having ICG-S and PEG was measured and then the ratio was determined based on an absorbance at its maximum absorption wavelength (around 790 nm) by using ICG-S-alkyne as a standard substance. The introduction ratio of a PEG moiety was calculated from the conversion ratio of azide groups and the introduction ratio of an ICG-S moiety. In addition, a yield was determined with a molecular weight calculated based on the introduction ratios of ICG-S and PEG moieties. The cac's of the hyaluronic acid derivatives 4a, 4b, and 4c were 2.6, 3.0, and 3.9 (×10⁻⁴ g/L), respectively.

TABLE 5

Synthesis of hyaluronic acid derivative 4 having ICG-S and PEG

| Polymer No. | a/b | Yield (%)[a] | p:q[b] | $D_{DLS}$ (nm) |
|---|---|---|---|---|
| 4a | 0.75/1.25 | 84 | 24:76 | 83 ± 25[c] |
| 4b | 1.00/1.00 | 79 | 30:70 | 130 ± 31[c] |
| 4c | 1.25/0.75 | 54 | 54:46 | 14 ± 3[d,e]  92 ± 36[d,e] |

[a]Calculated from a molecular weight based on the introduction ratios of ICG-S and PEG moieties.
[b]Calculated from the integrated value of ¹H-NMR and an absorbance in UV-vis measurement.
[c]Determined by dynamic light scattering after dissolving a polymer in water.
[d]Determined by dynamic light scattering after: dissolving a polymer in DMF; mixing the solution with the same amount of water; and removing DMF by dialysis.
[e]A scattering intensity ratio between the two kinds of particles was 1:4.

Figure 23A:
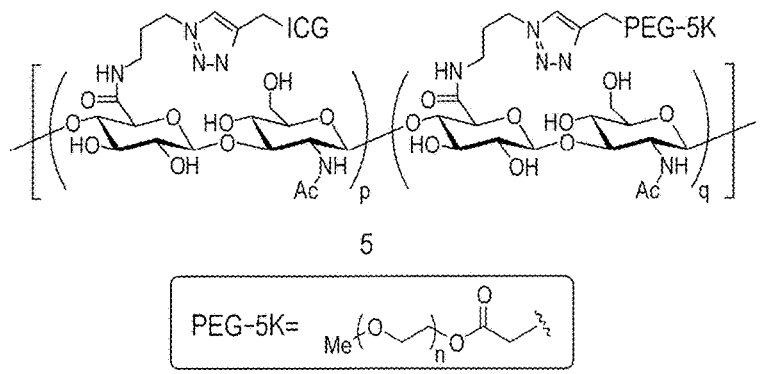
FIG. 23A illustrates a structural formula for a near-infrared dye-containing hyaluronic acid derivative 5 having PEG-5K and FIG. 23B illustrates a synthesis scheme for PEG-5K-alkyne.

Example 7: Synthesis of Near-Infrared Dye-Containing Hyaluronic Acid Derivative 5 Having PEG Having Molecular Weight of 5K A hyaluronic acid derivative 5 having PEG having a molecular weight of 5K (FIG. 23A) was synthesized according to the same scheme as that of Example 1(5) except that PEG-5K-alkyne as a derivative of PEG having a molecular weight of 5K was used. An HA-Na having a molecular weight of 5K was used as a starting material.

Example 7(1): Synthesis of PEG-5K-Alkyne

Figure 23B:
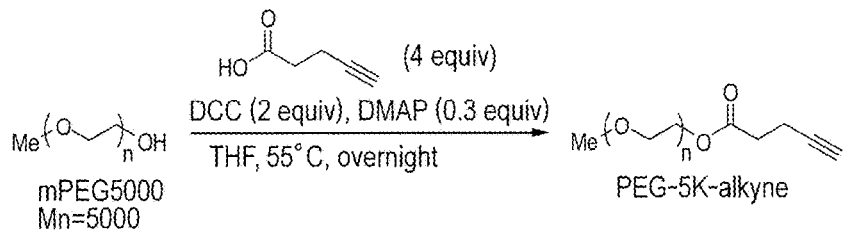

The synthesis of PEG-5K-alkyne is described below (FIG. 23B). 10 Grams (2.0 mmol) of a commercial mPEG5000 were loaded into a 200-ml two-necked round-bottom flask and then dried at 100° C. overnight under reduced pressure. The dried product was left standing to cool to 55° C. and then dissolved in 80 ml of THF. After 4-pentynoic acid (0.79 g, 8.0 mmol) had been added to the solution, 0.83 g (4.0 mmol) of DCC and 73 mg (0.6 mmol) of DMAP were added to the mixture, and then the whole was stirred at 55° C. overnight. After the resultant had been left standing to cool to room temperature, an insoluble solid was removed with a glass filter. The addition of an excessive amount of diethyl ether to the filtrate provided a white solid. The solid was separated from the filtrate with a glass filter and then washed with diethyl ether to provide 8.1 g (81%) of PEG-5K-alkyne as a white solid. Its identification was performed by ¹H-NMR. The results were as follows: (¹H-NMR (400 MHz, CDCl₃, 25° C., TMS) δ/ppm; 1.97-2.01 (m, 1H), 2.47-2.55 (m, 2H), 2.55-2.64 (m, 2H), 3.40-3.92 (m, 591H), 4.26 (t, J=5.0 Hz, 2H)).

Figure 24A:
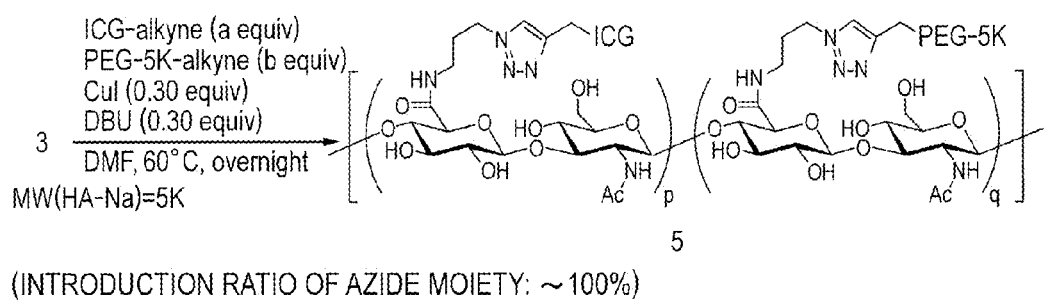
FIG. 24A illustrates a synthesis scheme for the hyaluronic acid derivative 5 having ICG and PEG-5K.

Example 7(2): Synthesis of Hyaluronic Acid Derivative 5 Having ICG and PEG-5K The various hyaluronic acid derivatives 5 each having ICG and PEG-5K can each be obtained by simultaneously conjugating ICG-alkyne and PEG-5K-alkyne to the hyaluronic acid analog 3 having an azide group (FIG. 24A and Table 6). A typical synthesis example is described below. Under a nitrogen atmosphere, 23 mg of the derivative 3 (MW(HA-Na)=5K, 50 µmol in terms of minimum unit, azidation efficiency: >99%) were loaded into a 25-ml Schlenk flask and then dissolved in 2 ml of anhydrous DMF. After 26 mg (38 µmol) of ICG-alkyne and 0.31 g (63 µmol) of PEG-5K-alkyne had been added to the solution, 2.9 mg (15 µmol) of CuI and 2.3 mg (15 µmol) of DBU were added to the mixture, and then the whole was stirred at 60° C. overnight. 2 Milliliters of water were added to the solution and then the mixture was dialyzed with a dialysis membrane having a molecular weight cut-off of 25K for 24 hours against water. The resultant aqueous solution was filtered with a filter (pore diameter: 0.45 µm) and then freeze-dried to provide 0.27 g (63%) of a hyaluronic acid derivative 5 having ICG and PEG-5K as a deep green solid. Its identification was performed by ¹H-NMR (¹H-NMR (400 MHz, D₂O, 25° C.) δ/ppm; 1.65-2.10 (m, 3H), 2.54 (br s, 0.6H), 2.82-3.05 (m, 1.3H), 3.15-4.00 (m, 395H), 4.25-4.50 (m, 2H), 7.72 (s, 0.65H), 7.93 (br s, 0.15H). It should be noted that the conversion ratio of a cyclization reaction was calculated based on the reduction ratio of 2H (1.67 ppm) at the 2-position of 3-azido-1-propylamine by ¹H-NMR. The introduction ratio of an ICG moiety was determined as follows: the UV spectrum of a DMF solution of a hyaluronic acid derivative having ICG and PEG-5K was measured and then the ratio was determined based on an absorbance at its maximum absorption wavelength (around 790 nm) by using ICG-S-alkyne as a standard substance. The chemical shift (7.72 ppm) of a proton of a triazole ring to which PEG-5K had been conjugated was observed to differ from the chemical shift (7.93 ppm) of a proton of a triazole ring having ICG. Although the introduction ratio of a PEG moiety can be calculated from the conversion ratio of azide groups and the introduction ratio of an ICG moiety, the ratio can also be calculated based on the ratio of an azide group transformed into a triazole ring having PEG-5K to the reacted azide groups and the conversion ratio of the azide groups by utilizing the foregoing. In addition, a yield was determined with a molecular weight calculated based on the introduction ratios of ICG and PEG-5K moieties.

The cac's of the hyaluronic acid derivatives 5a and 5b were 2.1 and 3.8 (×10⁻⁴ q/L), respectively.

TABLE 6

Synthesis of hyaluronic acid derivative 5 having ICG and PEG-5K

| Polymer No. | a/b | Yield (%)[a] | p:q[b] | $D_{DLS}$ (nm)[c] |
|---|---|---|---|---|
| 5a | 0.75/1.25 | 63 | 28:72 | 84 ± 28 |
| 5b | 1.00/1.00 | 63 | 45:55 | 84 ± 27 |

[a]Calculated from a molecular weight based on the introduction ratios of ICG and PEG-5K moieties.
[b]Calculated from the integrated value of ¹H-NMR and an absorbance in UV-vis measurement.
[c]Determined by dynamic light scattering after dissolving a polymer in water.

Figure 24B:
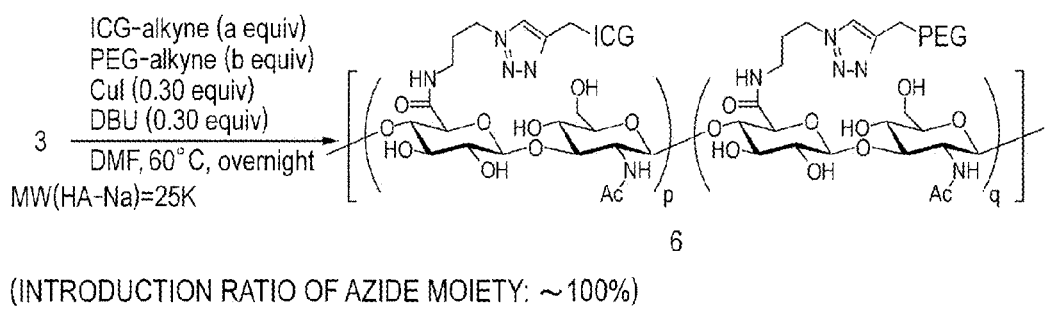
FIG. 24B illustrates a synthesis scheme for a high-molecular weight hyaluronic acid derivative 6 having a near-infrared dye.

Example 8: Synthesis of High-Molecular Weight Hyaluronic Acid Derivative 6 Having Near-Infrared Dye A hyaluronic acid derivative 6 having a near-infrared dye was synthesized according to the same scheme as that of Example 1 except that an HA-Na having a molecular weight of 25K was used as a starting material. A high-molecular weight hyaluronic acid derivatives 6 each having ICG and PEG can each be obtained by simultaneously conjugating ICG-alkyne and PEG-alkyne to the hyaluronic acid analog 3 having an azide group (FIG. 24B and Table 7). A typical synthesis example is described below. Under a nitrogen atmosphere, 23 mg of the derivative 3 (MW(HA-Na)=25K, 50 µmol in terms of minimum unit, azidation efficiency: >99%) were loaded into a 25-ml Schlenk flask and then dissolved in 2 ml of anhydrous DMF. After 17 mg (25 µmol)

of ICG-alkyne and 0.15 g (75 µmol) of PEG-alkyne had been added to the solution, 2.9 mg (15 µmol) of CuI and 2.3 mg (15 µmol) of DBU were added to the mixture, and then the whole was stirred at 60° C. overnight. 2 Milliliters of water were added to the solution and then the mixture was dialyzed with a dialysis membrane having a molecular weight cut-off of 25K for 24 hours against water. The resultant aqueous solution was filtered with a filter (pore diameter: 0.45 µm) and then freeze-dried to provide 42 mg (35%) of a hyaluronic acid derivative 6 having ICG and PEG as a deep green solid. Its identification was performed by $^1$H-NMR ($^1$H-NMR (400 MHz, $D_2O$, 25° C.) δ/ppm; 1.71-2.13 (m, 3H), 3.22-4.00 (m, 390H), 4.30-4.53 (m, 2H), 7.93 (br s, 0.99H)). The reaction is poor in reproducibility. In addition, a low introduction amount with respect to the amount of ICG to be used is characteristic.

It should be noted that the conversion ratio of a cyclization reaction was calculated based on the reduction ratio of 2H (1.67 ppm) at the 2-position of 3-azido-1-propylamine by $^1$H-NMR. The introduction ratio of an ICG moiety was determined as follows: the UV spectrum of a DMF solution of a hyaluronic acid derivative having ICG and PEG was measured and then the ratio was determined based on an absorbance at its maximum absorption wavelength (around 790 nm) by using ICG-alkyne as a standard substance. The introduction ratio of a PEG moiety was calculated from the conversion ratio of azide groups and the introduction ratio of an ICG moiety. In addition, a yield was determined with a molecular weight calculated based on the introduction ratios of ICG and PEG moieties. The cac's of the hyaluronic acid derivatives 6a and 6b were 14 and 18 ($\times 10^{-4}$ g/L), respectively.

TABLE 7

Synthesis of high-molecular weight hyaluronic acid derivative 6 having near-infrared dye

| Polymer No. | a/b | Yield (%)[a] | p:q[b] | | $D_{DLS}$ (nm) |
|---|---|---|---|---|---|
| 6a | 0.50/1.50 | 35 | 4:96 | 26 ± 6[c,d] | 150 ± 77[c,d] |
| 6b | 0.75/1.25 | 34 | 16:84 | | 111 ± 45[e] |

[a]Calculated from a molecular weight based on the introduction ratios of ICG and PEG moieties.
[b]Calculated from the integrated value of $^1$H-NMR and an absorbance in UV-vis measurement.
[c]Determined by dynamic light scattering after dissolving a polymer in water.
[d]A scattering intensity ratio between the two kinds of particles was 1:2.
[e]Determined by dynamic light scattering after: dissolving a polymer in DMF; mixing the solution with the same amount of water; and removing DMF by dialysis.

Example 9: Evaluation for Tumor-Contrasting Ability by Fluorescence Imaging

Figure 25A:
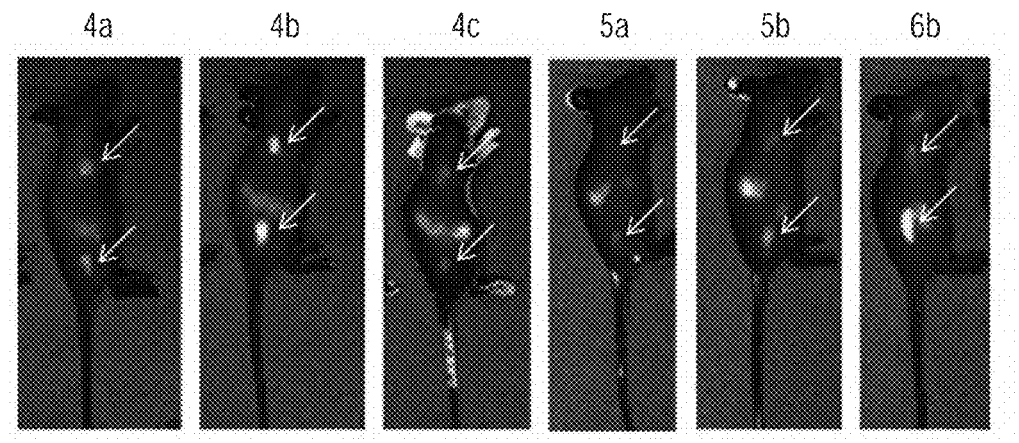
FIG. 25A shows fluorescence images of mice to which hyaluronic acid derivatives 4a, 4b, 4c, 5a, 5b, and 6b have been administered 24 hours after the administration.

The compounds obtained in Examples 6 to 8 described above were evaluated for their tumor-contrasting abilities by the same method as that of Example 3 described above. With regard to the whole-body fluorescence images of mice to which the hyaluronic acid derivatives 4a, 4b, 4c, 5a, 5b, and 6b had been administered, the bright-field images and fluorescence images of the mice were acquired with an IVIS (trademark) Imaging System 200 Series (XENOGEN) 24 hours after the administration. The injected dose was 50 nmol per mouse in terms of a dye amount and the dye was injected as 100 µL of a PBS solution into the tail vein of each mouse. FIG. 25A shows the fluorescence images of the mice 24 hours after the administration. Fluorescence signals at tumor sites indicated by white arrows in FIG. 25A were observed in all samples. The results showed that the hyaluronic acid derivative of the present invention was able to contrast a tumor and showed its effectiveness as a contrast agent for the optical imaging of a tumor.

Figure 25B:
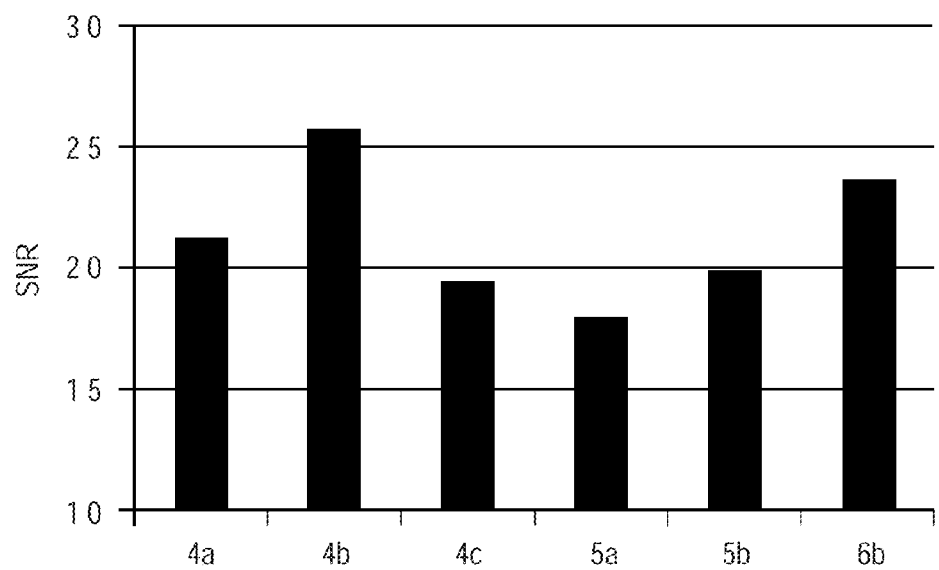
FIG. 25B is a graph showing the SNR's of mouse tumor images of the mice to which the hyaluronic acid derivatives 4a, 4b, 4c, 5a, 5b, and 6b have been administered 24 hours after the administration.

In FIG. 25B, a ratio between the fluorescence intensity of a tumor site (measured area: 0.5×0.5 cm) and the fluorescence intensity of the base of a leg (selected as a normal site, measured area: 0.5×0.5 cm) is drawn from the fluorescence imaging data shown in FIG. 25A, and is then converted into a numerical value as a signal-to-noise ratio (SNR). That is, the SNR is a parameter showing the tumor-visualizing power of each compound and the compound becomes more effective as a contrast agent for the optical imaging of a tumor as the SNR increases. It was shown from FIG. 25B that the SNR's of all compounds were 1.5 or more, and the derivatives 4b and 6b were compounds having excellent tumor-contrasting abilities because of their particularly high SNR's.

Figure 26A:
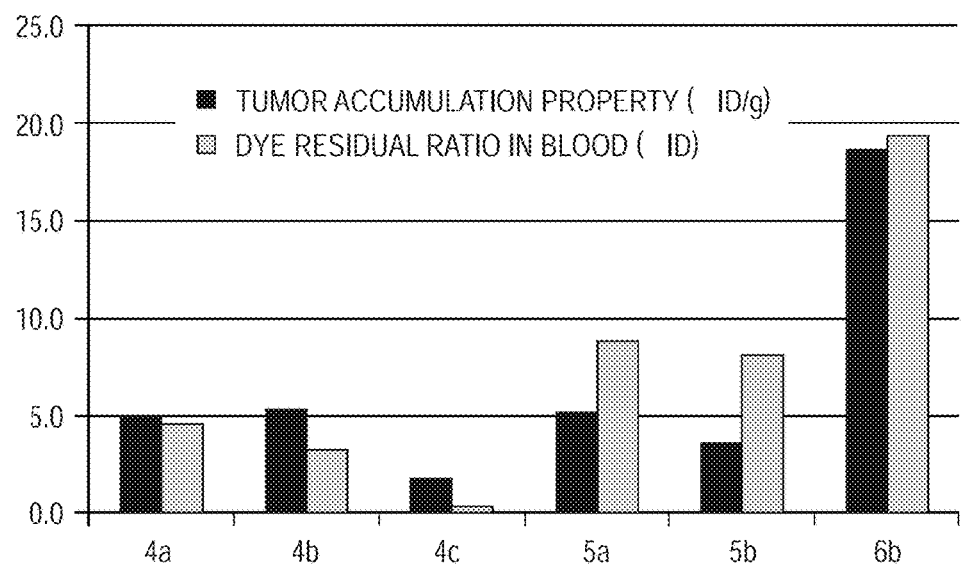
FIG. 26A is a graph showing the tumor accumulation properties and dye residual ratios in blood of the hyaluronic acid derivatives 4a, 4b, 4c, 5a, 5b, and 6b.

Example 10: Evaluations for Tumor Accumulation Property and Dye Residual Ratio in Blood The hyaluronic acid derivatives 4a, 4b, 4c, 5a, 5b, and 6b were evaluated for their tumor accumulation properties and dye residual ratios in blood by determining the amount of a dye in the tumor of a mouse of the tumor-contrasting experiment performed in Example 9 and the amount of the dye in the blood thereof. The tumor accumulation property was evaluated by the same method as that of Example 4. The dye residual ratio in blood was evaluated by the same method as that of Example 2. FIG. 26A shows the results. The dye was detected in the tumor to which the hyaluronic acid derivative according to the present invention had been administered, and hence accumulation in the tumor was confirmed. The tumor accumulation properties ranged from 1.7% to 18.5% and the derivative 6b showed the highest tumor accumulation property, i.e., 18.5% ID/g. The hyaluronic acid derivative 4 having ICG-S and PEG was found to be a compound having high tumor selectivity because its tumor accumulation property was relatively high despite the fact that its dye residual ratio in blood was low. The following tendency was observed: the tumor accumulation property reduced as the ICG content increased. In the hyaluronic acid derivative 5 having ICG and PEG-5K, the tumor accumulation property reduced as compared to that of a compound having a PEG molecular weight of 2K (such as the derivative 1i) while the dye residual ratio in blood increased. The tumor accumulation property and concentration in blood of the high-molecular weight hyaluronic acid derivative 6 having a near-infrared dye were high. The tumor accumulation property improved probably because of its extremely high retentivity in blood.

Example 11: Measurement of Photoacoustic Signal

Figure 26B:
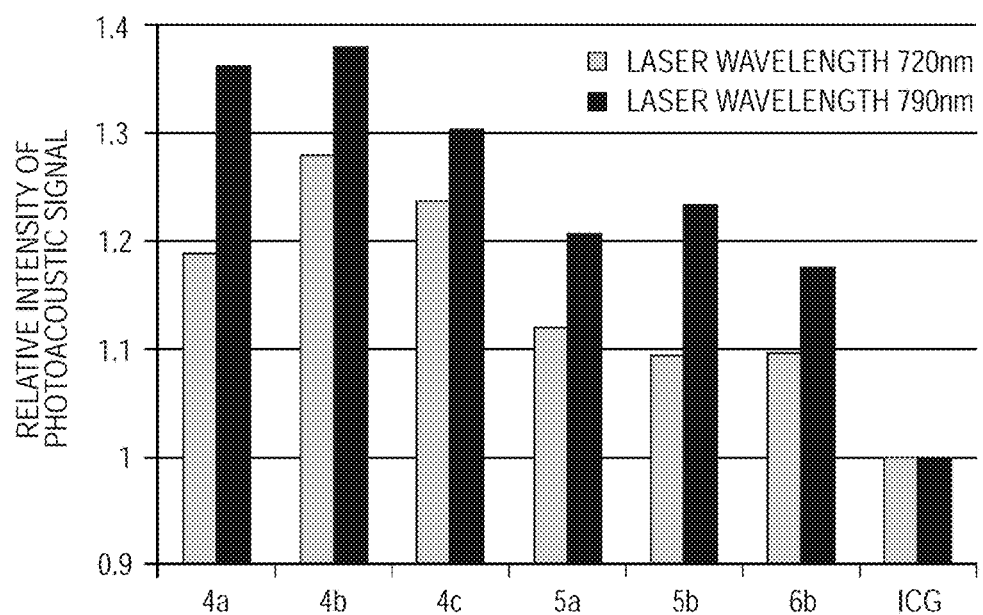
FIG. 26B is a graph showing the relative intensities of the photoacoustic signals of the hyaluronic acid derivatives 4a, 4b, 4c, 5a, 5b, and 6b.

The photoacoustic signals of the hyaluronic acid derivatives 4a, 4b, 4c, 5a, 5b, and 6b were measured in the same manner as in Example 5. As a comparative example, an aqueous solution of ICG was similarly subjected to the measurement. FIG. 26B shows the photoacoustic signal intensity of the compound of the present invention relative to the photoacoustic signal intensity of ICG. As is apparent from FIG. 26B, the derivatives 4a, 4b, 4c, 5a, 5b, and 6b were able to emit photoacoustic signals and were able to provide photoacoustic signal intensities higher than that of ICG. In particular, the hyaluronic acid derivative 4 having ICG-S and PEG showed an increase in photoacoustic signal intensity by a factor of 1.3 to 1.4 as compared to that of ICG.

A possible mechanism for the increase in signal intensity is, for example, that the thermal conversion efficiency of the dye itself is higher than that of ICG, or that the molecules of the dye strongly aggregate and the dye is shielded from water as a medium, and hence heat is trapped. The results of this example have confirmed that the compound of the present invention functions as a photoacoustic contrast agent.

Example 12: Measurement of Intensity of Photoacoustic Signal from Tumor Site of Cancer-Bearing Mouse The intensity of a photoacoustic signal from the tumor site of a cancer-bearing mouse was measured as described below. A commercial photoacoustic imaging apparatus (Nexus 128 manufactured by Endra Inc.) was used. The wavelength of laser was set to 790 nm. Photoacoustic signals from the tumor site were measured before the administration of the compound of the present invention and 24 hours after the administration, followed by the acquisition of three-dimensional reconstruction data on each of the signals. A photoacoustic intensity of the entire measurement region (2 cm×2 cm×2 cm) as a region of interest (ROI) was measured with the resultant three-dimensional reconstruction data and a software (GEHC MICROVIEW, GE Healthcare). The mouse described in Example 3 was used as the cancer-bearing mouse. The compounds 1a, 1c, 1i, 2c, 2g, 4a, and 4b according to Examples of the present invention and physiological saline as a control were administered. For the injected dose of each of the compounds, 50 nmol of ICG were administered to the mouse.

Table 8 shows ratios between the photoacoustic signals from the tumor site before the administration and 24 hours after the administration. In all the compounds, it was found that the photoacoustic signals increased after the administration as compared to the control. The results have shown that the compound of the present invention enables the photoacoustic imaging of a tumor.

TABLE 8

Ratio between intensities of photoacoustic signals from tumor site before and after administration of compound

| Compound | Ratio between intensities of photoacoustic signals (after administration/before administration) | | | | |
|---|---|---|---|---|---|
| | Experiment 1 | Experiment 2 | Experiment 3 | Average value of three experiments | Standard deviation of average value |
| 1a | 3.9 | 4.2 | 3.4 | 3.8 | 0.4 |
| 1c | 4.7 | 6.6 | 10.9 | 7.4 | 3.2 |
| 1i | 3.5 | 6.6 | 7.1 | 5.7 | 1.9 |
| 2c | 4.1 | 3.6 | 3.5 | 3.8 | 0.3 |
| 2g | 2.5 | 8.2 | 2.8 | 4.5 | 3.2 |
| 4a | 1.0 | 2.3 | 3.2 | 2.2 | 1.1 |
| 4b | 5.2 | 1.1 | 1.2 | 2.5 | 2.4 |
| Control (physiological saline) | 0.7 | None | None | 0.7 | Unable to calculate |

Figure 27:
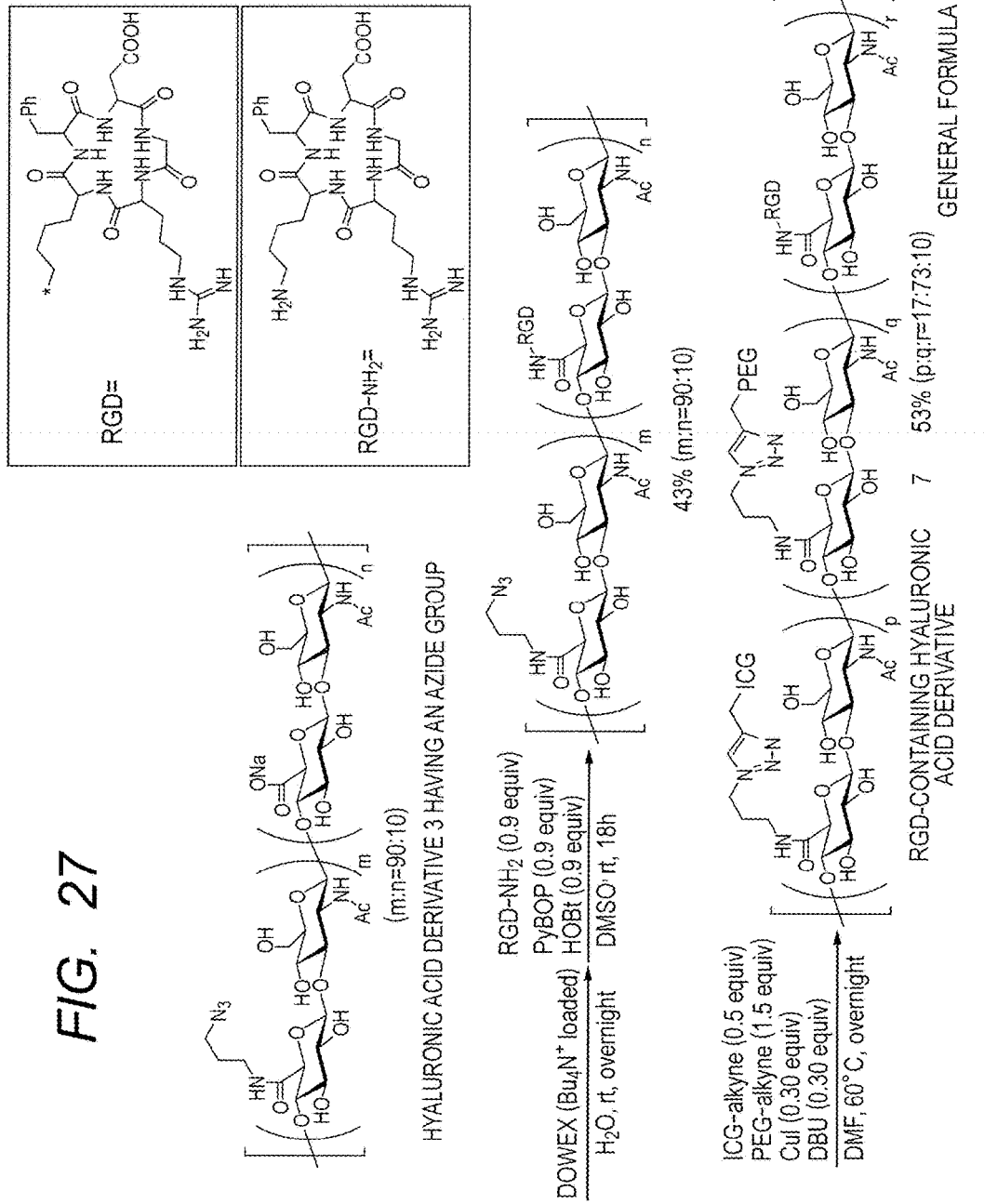
FIG. 27 illustrates a synthesis scheme for a hyaluronic acid derivative 7 (general formula (31)) having ICG, PEG, and RGD.

Example 13: Synthesis of Hyaluronic Acid Derivative 7 Having ICG, PEG, and RGD A hyaluronic acid derivative having an azide group and RGD was synthesized by introducing a cyclic RGD peptide to a carboxyl group moiety of unreacted HA with respect to the hyaluronic acid derivative 3 (table 1, entry No. 3), in which 3-azido-1-propylamine had been partially introduced into HA, obtained in Example 1(4), and then the conjugation of ICG and PEG to the derivative was performed (FIG. 27). A specific example is described below.

Cation exchange was performed by subjecting 12 mg of the hyaluronic acid derivative, to 90% of the groups of which 3-azido-1-propylamine had been conjugated, obtained under the conditions of the entry No. 3 of Table 1 (MW(HA-Na)=8K, 30 μmol in terms of minimum unit) to the reaction described in Example 1(2). Subsequently, under a nitrogen atmosphere, 9.7 mg of the resultant white solid (20 μmol in terms of minimum unit) were loaded into a 25-mL Schlenk flask and then dissolved in 0.50 ml of anhydrous DMSO. 9.5 Milligrams (18 μmol) of PyBOP and 2.4 mg (18 μmol) of HOBt were added to the solution. After that, 1.1 ml of a DMSO solution of 11 mg (18 μmol) of a cyclic RGD peptide (RGD-NH$_2$) were added to the mixture, and then the whole was stirred at room temperature for 18 hours. Water was added to the solution, the aqueous layer was washed with CH$_2$Cl$_2$, and the aqueous layer was dialyzed with a dialysis membrane having a molecular weight cut-off of 3.5K for 24 hours. The resultant was freeze-dried to provide 6.5 mg (43%) of a hyaluronic acid derivative in which the introduction efficiency of an azide group and that of RGD were 90% and 10%, respectively as a white solid in two stages. Its identification was performed by $^1$H-NMR. It should be noted that the introduction efficiency of RGD was calculated from a ratio between 3H (1.87 ppm) of an N-acetyl (Ac) group in the hyaluronic acid and 5H (7.05-7.28 ppm) of a phenyl (Ph) group in phenylalanine of RGD. The results were as follows: $^1$H-NMR (400 MHz, D$_2$O, 25° C.) δ/ppm; 1.69 (s, 1.8H), 1.88 (s, 3H), 3.00-3.85 (m, 14H), 4.39 (m, 2H), 7.05-7.28 (m, 0.50H).

Next, ICG-alkyne and PEG-alkyne were caused to act on the hyaluronic acid derivative having an azide group and RGD obtained in the foregoing under the same reaction conditions as those of Example 1(5) to provide a hyaluronic acid derivative 7 having ICG, PEG, and RGD in a yield of 53% (FIG. 27). An introduction ratio among ICG, PEG, and RGD was 17:73:10. Its identification was performed by $^1$H-NMR ($^1$H-NMR (400 MHz, D$_2$O, 25° C.) δ/ppm; 1.70-2.15 (m, 3H), 3.10-4.00 (m, 261H), 4.25-4.50 (m, 2H), 7.94 (br s, 0.89H)). It should be noted that the conversion ratio of a cyclization reaction was determined by the approach described in [0079] of the description of the present application. A self-assembly formed by the resultant compound in water had a particle diameter of 94±68 nm and a critical aggregation concentration of $4.0 \times 10^{-4}$ g/l.

Advantageous Effects of Invention

The inventors were the first to find that the ICG content of a hyaluronic acid derivative could be increased by simultaneously conjugating an ICG derivative and PEG to hyaluronic acid, and have succeeded in creating a hyaluronic acid derivative having a high ICG content. As compared to the case where ICG is administered alone to a living body, the hyaluronic acid derivative according to the present invention has high retentivity in blood or high accumulation property in a tumor, and the intensity of a photoacoustic signal emitted from the blood or tumor is large. In addition, the intensity of a photoacoustic signal per hyaluronic acid is large because of the high ICG content.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-033633, filed Feb. 22, 2013, which is hereby incorporated by reference herein in its entirety.

The invention claimed is:

1. A polymer formed of units each represented by general formula (1):

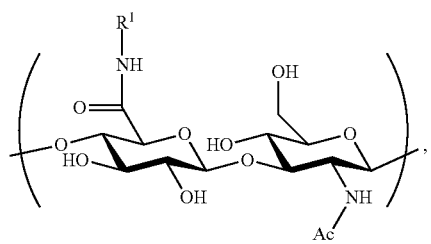

wherein:
R$^1$'s are independent of each other from unit to unit in the general formula (1); and
the polymer contains at least one unit in which R$^1$ is selected from the group consisting of general formula (2) and general formula (25), and at least one unit in which R$^1$ is general formula (3):

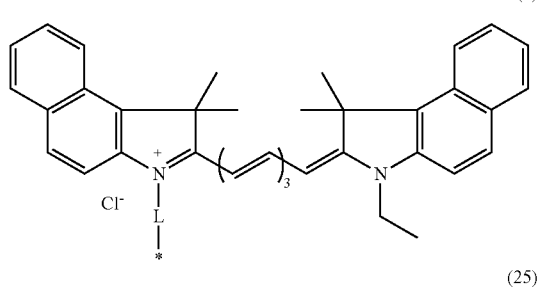

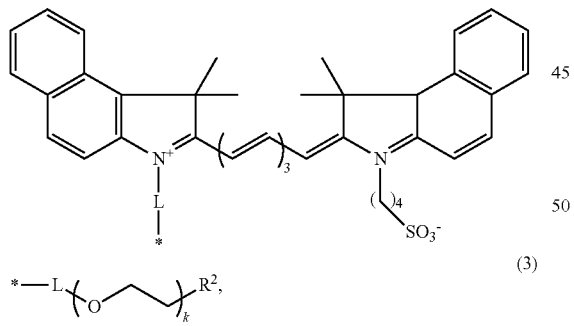

provided that: in the general formula (2), the general formula (3), and the general formula (25), L's represent linkers independent of each other from unit to unit, and * represents a binding site with N in the general formula (1); and in the general formula (3), R$^2$ represents any one of H, OH, OMe, NH$_2$, and COOH, and k represents an integer of 20 or more and 200 or less, wherein 0.13<x/N≤0.78,
where:
x is a number of units in the polymer in which R$^1$ is the general formula (2) or the general formula (25) and N is a number of all units in the polymer.

2. A polymer formed of units each represented by general formula (1):

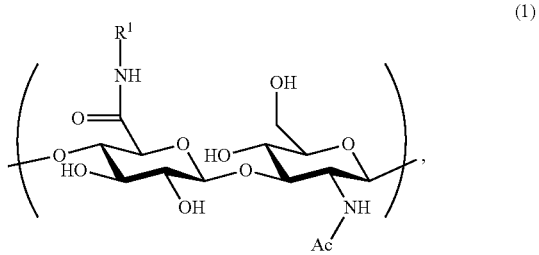

wherein:
R$^1$'s are independent of each other from unit to unit in the general formula (1);
R$^1$ is selected from the group consisting of general formulae (2) to (5), general formula (25), and general formula (29); and
the polymer contains at least one unit in which R$^1$ is selected from the group consisting of the general formula (2) and the general formula (25), and at least one unit in which R$^1$ is the general formula (3):

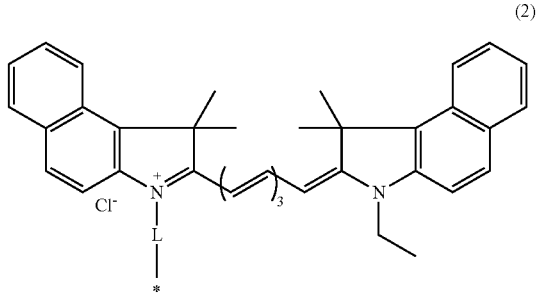

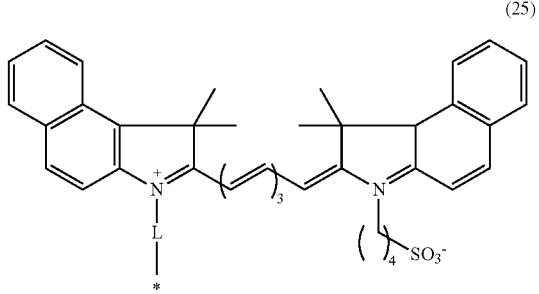

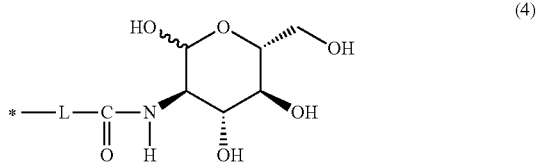

(29)

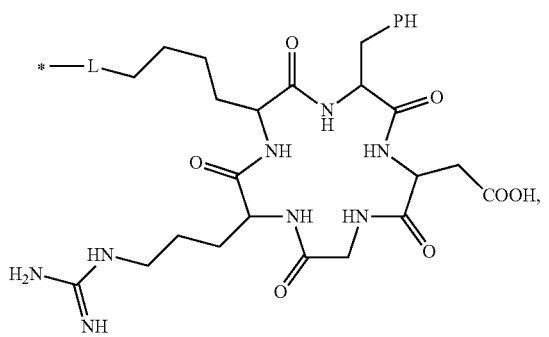

provided that: in the general formulae (2) to (5), the general formula (25), and the general formula (29), L's represent linkers independent of each other from unit to unit, and * represents a binding site with N in the general formula (1); in the general formula (3), $R^2$ represents any one of H, OH, OMe, $NH_2$, and COOH, and k represents an integer of 20 or more and 200 or less; and in the general formula (5), $R^3$ represents any one of $N_3$, H, $CH_3$, $NH_2$, SH, and COOH, wherein $0.13<x/(x+y+z)\le 0.78$, where:

x is a number of units in the polymer in which $R^1$ is the general formula (2) or the general formula (25), y is a number of units in the polymer in which $R^1$ is the general formula (3), and z is a number of units in the polymer in which $R^1$ is the general formula (4) or the general formula (29).

3. The polymer according to claim 2, wherein the polymer contains at least one unit in which $R^1$ is selected from the group consisting of the general formula (4) and the general formula (29).

4. A polymer formed of units each represented by any one of general formulae (6) to (9), general formula (28), and general formula (30), wherein the polymer contains at least one unit selected from the group consisting of the general formula (6) and the general formula (28), and at least one unit represented by the general formula (7):

(6)

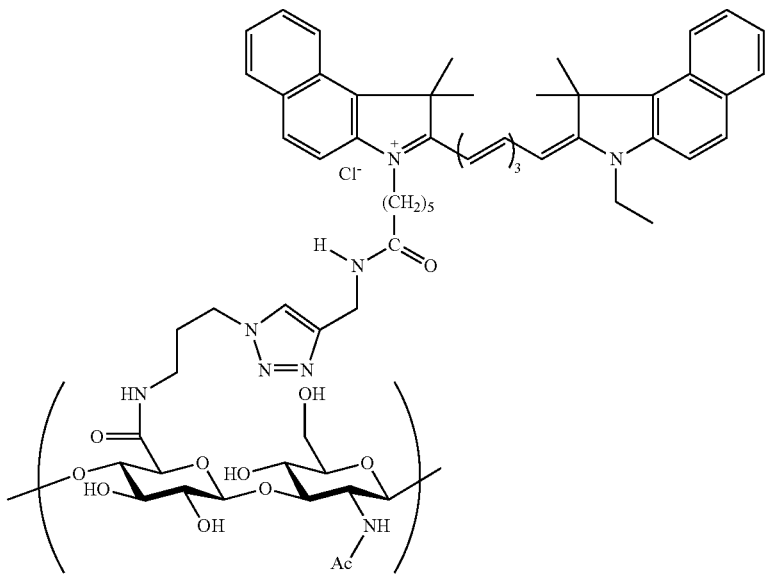

(28)

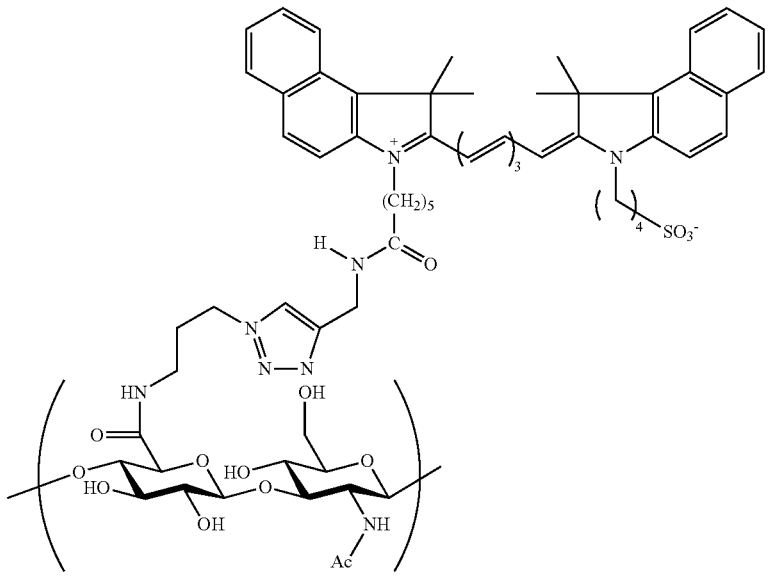

-continued
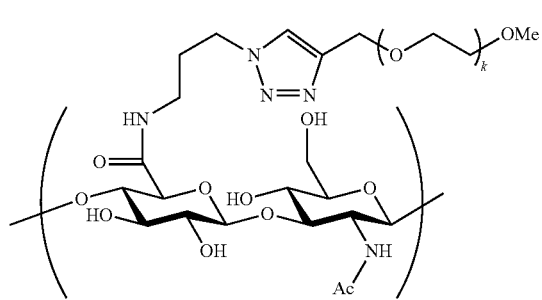
(7)
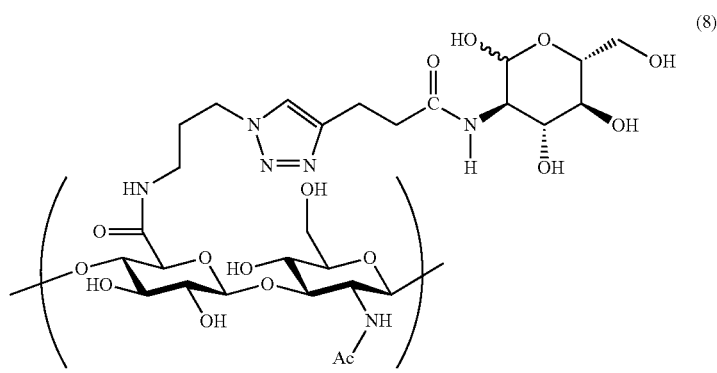
(8)
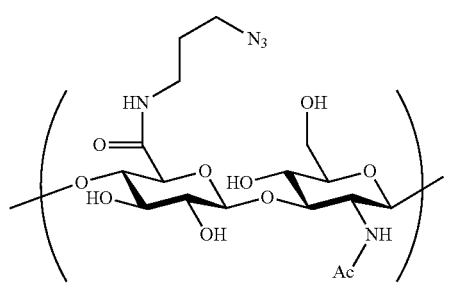
(9)
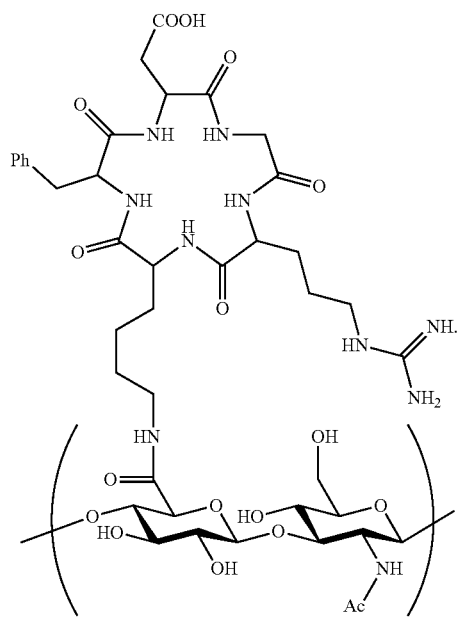
(30)

5. The polymer according to claim 4,
wherein $0.13 < x/(x+y+z) \leq 0.78$,
where:
x is a number of units in the polymer each represented by the general formula (6) or the general formula (28);
y is a number of units in the polymer each represented by the general formula (7); and
z is a number of units in the polymer each represented by the general formula (8), (9), or (30).

6. A particle, comprising the polymer according to claim 1.

7. A contrast agent for photoacoustic imaging, comprising:
the polymer according to claim 1; and
a dispersion medium.

8. The particle according to claim 6, wherein the particle has an average particle diameter of 10 nm to 180 nm.

9. A contrast agent for photoacoustic imaging, comprising:
the particle according to claim 6; and
a dispersion medium for the particle.

* * * * *